United States Patent [19]

Watanabe et al.

[11] Patent Number: 4,731,370
[45] Date of Patent: * Mar. 15, 1988

[54] PYRIDYL ESTER CONTAINING 1,4-DIHYDROPYRIDINE DERIVATIVES AND SALTS THEREOF AND PHARMACEUTICAL COMPOSITION CONTAINING THE SAME

[75] Inventors: Isao Watanabe, Toyama; Kaishu Momonoi, Shinminato; Toru Hiraiwa, Toyama; Satoshi Ono, Toyama; Joji Nakano, Toyama; Katsuyuki Nagumo, Kawasaki; Hiroyasu Takagi, Toyama, all of Japan

[73] Assignee: Toyama Chemical Co., Ltd., Tokyo, Japan

[*] Notice: The portion of the term of this patent subsequent to Dec. 15, 2004 has been disclaimed.

[21] Appl. No.: 872,408

[22] Filed: Jun. 10, 1986

Related U.S. Application Data

[63] Continuation-in-part of Ser. No. 747,305, Jun. 21, 1985.

[30] Foreign Application Priority Data

Jun. 25, 1984 [JP] Japan .................................. 59-130645
Jan. 7, 1985 [JP] Japan .................................. 60-497
Feb. 26, 1985 [JP] Japan .................................. 60-37130
Dec. 20, 1985 [JP] Japan .................................. 60-287000

[51] Int. Cl.$^4$ .................. C07D 401/12; A61K 31/455
[52] U.S. Cl. .................................. 514/332; 514/335; 546/113; 546/118; 546/122; 546/135; 546/138; 546/141; 546/143; 546/147; 546/256; 546/261; 546/263; 546/271; 546/272; 546/273; 546/278; 546/279; 546/281; 544/237; 544/238; 544/264; 544/265; 544/316; 544/319; 544/328; 544/331; 544/405

[58] Field of Search .............. 546/281, 261, 278, 273, 546/279, 256, 263, 141, 143, 122, 272, 271, 138, 135, 147, 113, 118; 544/405, 316, 331, 238, 319, 328, 264, 265, 237; 514/248, 252, 259, 260, 262, 265, 269, 275, 256, 333, 338, 332, 335, 303, 300, 306, 309, 310, 307, 312, 313, 314, 339, 341, 343

[56] References Cited

U.S. PATENT DOCUMENTS 4,532,248 7/1985 Frauckowiak et al. .............. 514/63

OTHER PUBLICATIONS

Bossert, F. et al., Angew Chem Int. Ed. Engl, 20, pp. 762–769 (1981).

Primary Examiner—Henry R. Jiles
Assistant Examiner—Dale A. Bjorkman
Attorney, Agent, or Firm—Oblon, Fisher, Spivak, McClelland & Maier

[57] ABSTRACT

This invention relates to a novel 1,4-dihydropyridine derivative of the formula

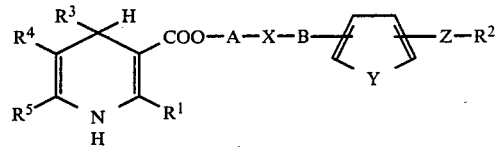

wherein R2 is pyridyl, or a salt thereof. These compounds have a vasodilating activity and a platelet aggregation inhibiting activity. Also disclosed are pharmaceutical compositions containing the same.

6 Claims, No Drawings

PYRIDYL ESTER CONTAINING 1,4-DIHYDROPYRIDINE DERIVATIVES AND SALTS THEREOF AND PHARMACEUTICAL COMPOSITION CONTAINING THE SAME

CROSS-REFERENCES TO RELATED APPLICATIONS

This application is a continuation-in-part of application Ser. No. 747,305, filed June 21, 1985.

BACKGROUND OF THE INVENTION

1. Field of the Invention

This invention relates to a novel 1,4-dihydropyridine derivative and a salt thereof which have a vasodilating activity and a platelet aggregation inhibiting activity and a pharmaceutical composition containing the same.

2. Description of the Prior Art

It has heretofore been known that dimethyl 2,6-dimethyl-4-(2-nitrophenyl)-1,4-dihydropyridine-3,5-dicarboxylate [generic name: nifedipine (U.S. Pat. No. 3,644,627)] and 3-[2-(N-benzyl-N-methylamino)ethyl]-5-methyl 2,6-dimethyl-4-(3-nitrophenyl)-1,4-dihydropyridine-3,5-dicarboxylate hydrochloride [generic name: nicardipine (Japanese Patent Publication No. 45,075/80)] and the like are useful as medicines for curing cerebral circulation disturbance and cardiac circulation disturbance.

However, it cannot be said that all of them are sufficient in activity to thrombosis which is one of the factors of the cerebral circulation disturbance and cardiac circulation disturbance though they have a strong vasodilating activity.

Accordingly, there has been desired the development of compounds having a platelet aggregation inhibiting activity as well as a vasodilating activity.

SUMMARY OF THE INVENTION

Under such circumstances, the present inventors have made extensive research and have consequently found that compounds obtained by introducing into the carboxyl group of a known 1,4-dihydropyridine derivative a group represented by the general formula:

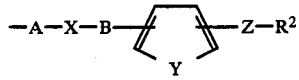

wherein $R^2$, A, B, X, Y and Z are as defined hereinafter, namely, a novel 1,4-dihydropyridine derivative and a salt thereof having the general formula (I) which is shown hereinafter, have not only a vasodilating activity but also an excellent platelet aggregation inhibiting activity and are very useful as a drug for curing circulation disturbance.

An object of this invention is to provide a novel 1,4-dihydropyridine derivative and a salt thereof.

Another object of this invention is to provide a pharmaceutical composition containing the novel 1,4-dihydropyridine derivative or a salt thereof.

The compounds of this invention are explained below.

According to this invention, there is provided a novel 1,4-dihydropyridine derivative represented by the general formula (I) or a salt thereof:

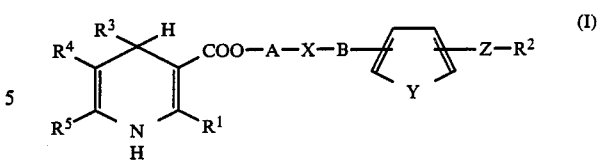

wherein $R^1$ and $R^5$, which may be the same or different, represent lower alkyl groups; $R^2$ represents a nitrogen-containing heterocyclic group; $R^3$ represents a substituted or unsubstituted aryl or aromatic heterocyclic group; $R^4$ represents an esterified carboxyl group; A represents an alkylene, alkyleneoxyalkylene or alkylenethioalkylene group; B represents an alkylene or alkenylene group or a linkage; X represents an oxygen or sulfur atom or a group of the formula

in which $R^6$ represents a hydrogen atom or a lower alkyl, aryl or aralkyl group; Y represents an oxygen or sulfur atom or a vinylene group; and Z represents an oxygen or sulfur atom or an alkylene group.

DETAILED DESCRIPTION OF THE INVENTION

In the present specification, unless otherwise specified, the lower alkyl group means $C_{1-4}$ alkyl groups such as methyl, ethyl, n-propyl, isopropyl, n-butyl, isobutyl, sec-butyl, tert-butyl and the like; the lower alkoxy group means $C_{1-4}$ alkoxy groups such as methoxy, ethoxy, n-propoxy, isopropoxy, n-butoxy, isobutoxy, sec-butoxy, tert-butoxy and the like; the aryl group includes, for example, phenyl, naphthyl and the like; the aralkyl group means substituted or unsubstituted aryl-lower alkyl groups such as benzyl, phenethyl, methylbenzyl, chlorobenzyl, methoxybenzyl and the like; the alkylene group means $C_{1-6}$ alkylene groups such as methylene, ethylene, propylene, trimethylene, tetramethylene, pentamethylene, hexamethylene, 1-methyltrimethylene, 2-methyltrimethylene, 2,2-dimethyltrimethylene, 1,3-dimethyltrimethylene and the like; the alkyleneoxyalkylene group means $C_{1-6}$ alkyleneoxy-$C_{1-6}$ alkylene groups such as methyleneoxyethylene, ethyleneoxyethylene, propyleneoxyethylene and the like; the alkylenethioalkylene group means $C_{1-6}$ alkylenethio-$C_{1-6}$ alkylene groups such as methylenethioethylene, ethylenethioethylene, propylenethioethylene and the like; the alkenylene group means $C_{2-4}$ alkenylene groups such as propenylene, methylpropenylene and the like; and the halogen atom includes, for example, fluorine, chlorine, bromine, iodine and the like.

The nitrogen-containing heterocyclic group for $R^2$ includes 5- and 6-membered and fused heterocyclic groups containing nitrogen such as pyrrolyl, imidazolyl, pyrazolyl, pyridyl, pyrazinyl, pyrimidinyl, pyridazinyl, indolyl, indolinyl, isoindolyl, indazolyl, quinolizinyl, quinolyl, isoquinolyl, purinyl, phthalazinyl, naphthyridinyl, benzimidazolyl, pyrrolopyridyl, imidazopyridyl, imidazopiperidinyl and the like.

The substituted or unsubstituted aryl or aromatic heterocyclic group for $R^3$ includes those which are conventionally known in the art. The aromatic heterocyclic group includes 5- and 6-membered heterocyclic groups such as thienyl, furyl, pyrrolyl, pyridyl and the like. The substituent on the aryl or aromatic heterocyclic group for $R^3$ includes, for example, halogen atoms; a nitro group; a cyano group; an azido group; lower alkyl groups; lower alkoxy groups; trihalo-lower alkyl groups such as trifluoromethyl and the like; lower alkanesulfonyl groups such as methanesulfonyl, ethanesulfonyl, propanesulfonyl and the like; aralkyl groups; aryl groups; aralkoxy groups such as benzyloxy, phenethyloxy, p-chlorobenzyloxy, p-methoxybenzyloxy and the like; aryloxy groups such as phenoxy, naphthoxy, p-methylphenoxy and the like; lower alkylthio groups such as methylthio, ethylthio, propylthio, butylthio and the like; arylthio groups such as phenylthio, naphthylthio, p-methylphenylthio and the like; aralkylthio groups such as benzylthio, phenethylthio, p-chlorobenzylthio, p-methoxybenzylthio and the like; and lower alkoxycarbonyl groups such as methoxycarbonyl, ethoxycarbonyl, propoxycarbonyl and the like. The aryl or aromatic heterocyclic group for $R^3$ may be substituted by at least one of the above substituents.

The ester-forming group in the esterfied carboxyl group for $R^4$ includes those ester-forming groups which are conventionally known in the art, for example, lower alkyl groups; lower alkoxy-lower alkyl groups such as methoxyethyl, methoxypropyl, ethoxyethyl, propoxyethyl, butoxyethyl and the like; lower alkylthio-lower alkyl groups such as methylthioethyl, ethylthioethyl, propylthioethyl, butylthioethyl and the like; N,N-di(-lower alkyl)amino-lower alkyl groups such as N,N-dimethylaminoethyl, N,N-diethylaminoethyl, N,N-dipropylaminoethyl and the like; N-aralkyl-N-lower alkylamino-lower alkyl groups such as N-benzyl-N-methylaminoethyl, N-(4-chlorobenzyl)-N-methylaminoethyl, N-benzyl-N-methylaminopropyl and the like; N-aryl-N-lower alkylamino-lower alkyl groups such as N-phenyl-N-methylaminoethyl and the like; N,N-diaralkylamino-lower alkyl groups such as N,N-dibenzylaminoethyl and the like; etc.

As the salts of the 1,4-dihydropyridine derivative represented by the general formula (I), there may be exemplified pharmaceutically acceptable salts, and they include salts with inorganic and organic acids, for example, salts with mineral acids such as hydrochloric acid, hydrobromic acid, sulfuric acid, phosphoric acid and the like; salts with organic carboxylic acids such as formic acid, acetic acid, fumaric acid, maleic acid, malic acid, tartaric acid, aspartic acid and the like; salts with sulfonic acids such as methanesulfonic acid, benzenesulfonic acid, toluenesulfonic acid, hydroxybenzenesulfonic acid, dihydroxybenzenesulfonic acid, naphthalenesulfonic acid and the like.

The compounds of this invention include optical isomers, geometrical isomers and tautomers, and also include all hydrates and crystal forms.

The 1,4-dihydropyridine derivative represented by the general formula (I) or a salt thereof can be produced by a method known per se, for example, one of the following methods:

Production Method 1

$R^3$—CHO + $R^5$—C=CH—$R^4$ +
                    |
                    $NH_2$ (II)        (III)
            or a salt thereof Production Method 1

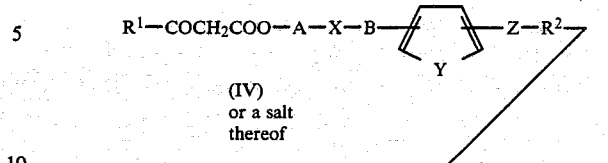

(IV)
or a salt
thereof

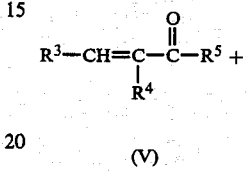

(I) or its salt

Production Method 2

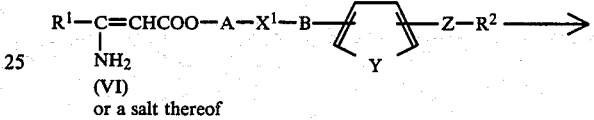

(V)

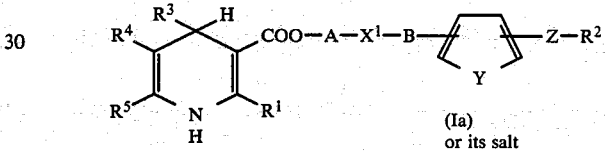

(VI)
or a salt thereof

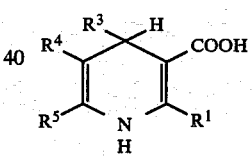

(Ia)
or its salt

Production Method 3

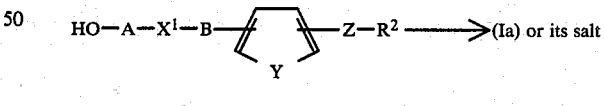

(VII) or a salt thereof
or a reactive derivative
in the carboxyl
group thereof

 → (Ia) or its salt (VIIIa)
or a salt thereof

Production Method 4

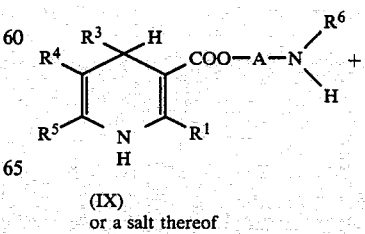

(IX)
or a salt thereof

Production Method 4

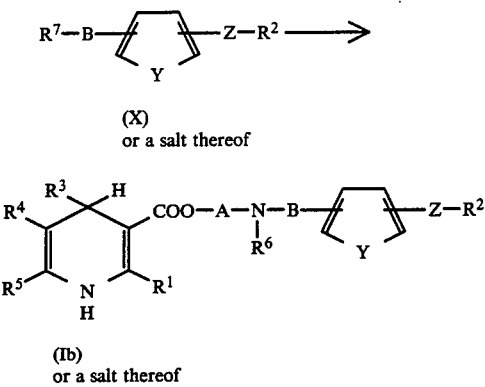

(X) or a salt thereof (Ib) or a salt thereof

Production Method 5

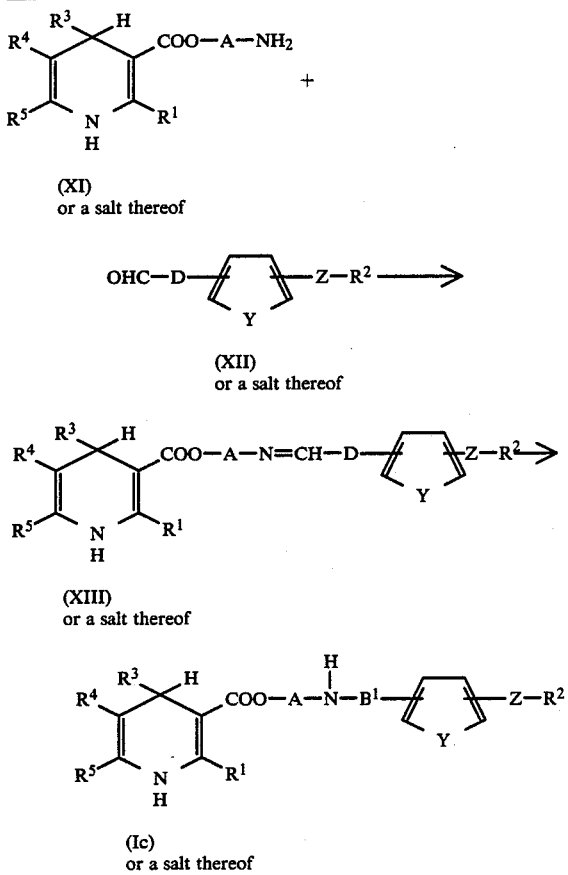

(XI) or a salt thereof (XII) or a salt thereof (XIII) or a salt thereof (Ic) or a salt thereof In the above formulas, $R^7$ represents a halogen atom or an alkanesulfonyloxy or arenesulfonyloxy group, $B^1$ and D represent alkylene or alkenylene groups, $X^1$ represents an oxygen or sulfur atom, or a group of the formula $$-\underset{\underset{R^{6a}}{|}}{N}-$$

in which $R^{6a}$ represents the same lower alkyl, aryl or aralkyl group as $R^6$, and $R^1$, $R^2$, $R^3$, $R^4$, $R^5$, $R^6$, A, B, X, Y and Z have the same meanings as defined above.

The salts of the compounds represented by the general formulas (III), (IV), (VI), (VII), (VIIIa), (IX), (X), (XI), (XII) and (XIII) include conventional salts at basic groups and acidic groups. The salts at basic groups include, for example, salts with mineral acids such as hydrochloric acid, sulfuric acid and the like; salts with organic carboxylic acids such as oxalic acid, formic acid, trichloroacetic acid, trifluoroacetic acid and the like; salts with sulfonic acids such as methane sulfonic acid, p-toluenesulfonic acid, naphthalenesulfonic acid and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as procaine, dibenzylamine, N-benzyl-β-phenethylamine, 1-ephenamine, N,N-dibenzylethylenediamine, triethylamine, trimethylamine, tributylamine, pyridine, N,N-dimethylaniline, N-methylpiperidine, N-methylmorpholine, diethylamine, dicyclohexylamine and the like.

Production Methods 1 and 2

The compound of the general formula (I) or a salt thereof can be obtained by subjecting the compound of the general formula (II), the compound of the general formula (III) or a salt thereof, and the compound of the general formula (IV) or a salt thereof to reaction or the compound of the general formula (V) and the compound of the general formula (VI) or a salt thereof to reaction, in the presence or absence of a solvent. The solvent used may be any solvent which does not adversely affect the reaction, and includes, for example, alcohols such as methanol, ethanol, 2-propanol, butanol, ethylene glycol, 2-methoxyethanol and the like; aromatic hydrocarbons such as benzene, toluene and the like; halogenated hydrocarbons such as methylene chloride, chloroform, 1,2-dichloroethane and the like; ethers such as tetrahydrofuran, dioxane, 1,2-dimethoxyethane and the like; esters such as ethyl acetate, butyl acetate and the like; nitriles such as acetonitrile and the like; carboxylic acids such as acetic acid, propionic acid, dichloroacetic acid and the like; amides such as N,N-dimethylformamide, water; etc. These solvents may be used alone or in admixture of two or more.

In the above reaction, the amount of each of the compound of the general formula (II) and the compound of the general formula (III) or a salt thereof is preferably 0.5 to 2.0 moles per mole of the compound of the general formula (IV), and the amount of the compound of the general formula (V) is preferably 0.5 to 2.0 moles per mole of the compound of the general formula (VI) or a salt thereof. The above reaction may be conducted at a temperature of 30° to 150° C. for a period of 1 to 24 hours.

Production Method 3

The compound of the general formula (Ia) or a salt thereof can be produced by reacting the compound of the general formula (VII) or a salt thereof with the compound of the general formula (VIIIa) or a salt thereof in the presence of a condensing agent or by reacting a reactive derivative in the carboxyl group of the compound of the general formula (VII) or a salt thereof with the compound of the general formula (VIIIa) or a salt thereof in the presence or absence of an acid-binding agent, both reactions being carried out in the same manner as in the esterification of conventional carboxylic acids, for example, in the presence or absence of a solvent which does not adversely affect the reaction. The solvent used in these reactions includes water and organic solvents, for example, aromatic hydrocarbons such as benzene, toluene and the like; halogenated hydrocarbons such as methylene chloride, chloroform, carbon tetrachloride, 1,2-dichloroethane and the like; ethers such as diethyl ether, tetrahydrofuran, dioxane and the like; ketones such as acetone, methyl ethyl ketone and the like; esters such as ethyl acetate, butyl acetate and the like; nitriles such as acetonitrile and the like; amides such as N,N-dimethylformamide, N,N-dimethylacetamide and the like; and these solvents may be used alone or in admixture of two or more. The condensing agent used in the above reaction includes dehydrating agents, for example, N,N'-di-substituted carbodiimides such as N,N'-dicyclohexylcarbodiimide and the like; N-ethoxycarbonyl-2-ethoxy-1,2-dihydroquinoline; and the like. The reactive derivative in the carboxyl group of the compound of the general formula (VII) includes, for example, acid halides such as acid chloride, acid bromide and the like; acid anhydrides such as symmetric acid anhydrides between two molecules of the compound of the general formula (VII) and the like; mixed acid anhydrides such as mixed acid anhydride with monoethyl carbonate and the like; active esters such as dinitrophenyl ester, cyanomethyl ester, succinimido ester and the like; active acid amides such as acid amides with imidazole and the like; etc. The acid-binding agent used includes, for example, triethylamine, N,N-dimethylaniline, pyridine, alkali hydroxides and the like.

In the above reactions, the amount of the compound of the general formula (VII) or the reactive derivative in the carboxyl group thereof or a salt thereof is preferably about 0.2 to about 1 mole per mole of the compound of the general formula (VIIIa) or a salt thereof. The acid-binding agent may be used as the solvent. The above reaction is preferably conducted at a temperature of −20° C. to 50° C. for a period of 5 minutes to 5 hours.

Production Method 4

The compound of the general formula (Ib) or a salt thereof can be produced by reacting the compound of the general formula (IX) or a salt thereof with the compound of the general formula (X) or a salt thereof in the presence or absence of an acid-binding agent and a solvent. The acid-binding agent used includes, for example, amines such as triethylamine, diisopropylamine, pyridine, 4-dimethylaminopyridine, N,N-dimethylaniline and the like, and the solvent may be any solvent which does not adversely affect the reaction, and includes, for example, the same solvents as mentioned in Production Method 1.

In the above reaction, the amount of the compound of the general formula (X) or a salt thereof used is preferably 0.5 to 1.0 mole per mole of the compound of the general formula (IX) or a salt thereof, and the amount of the acid-binding agent used may be at least equimolar to the compound of the general formula (X) or a salt thereof; however, when it is used in excess it can also serve as the solvent. The above reaction may be conducted at a temperature of 30° to 120° C. for a period of 10 minutes to 20 hours.

Production Method 5

The compounds of the general formula (Ib) or a salt thereof wherein $R^6$ is a hydrogen atom, namely, the compounds of the general formula (Ic) or a salt thereof, can also be produced by reducing the compound of the general formula (XIII) or a salt thereof obtained by subjecting the compound of the general formula (XI) or a salt thereof and the compound of the general formula (XII) or a salt thereof to dehydration-condensation reaction.

The dehydration-condensation reaction is effected in a solvent, for example, an aromatic hydrocarbon such as benzene, toluene or the like; an alcohol such as ethanol, 2-propanol or the like; a halogenated hydrocarbon such as methylene chloride, 1,2-dichloroethane or the like and, if necessary, in the presence of an acid catalyst such as p-toluenesulfonic acid, methanesulfonic acid, hydrochloric acid, sulfuric acid or the like and/or a dehydrating agent such as Molecular Sieves or the like. In the above reaction, the compound of the general formula (XII) or a salt thereof used is preferably 1.0 to 1.5 moles per mole of the compound of the general formula (XI) or a salt thereof. The above reaction may be effected at a temperature of 30° to 120° C. for a period of 1 to 12 hours. The compound of the general formula (XIII) or a salt thereof thus obtained may be used without isolation in the subsequent reaction.

The above reduction reaction is effected by using a reducing agent such as sodium boron hydride, sodium boron cyanohydride or the like in a solvent such as methanol, ethanol or the like. In this reaction, the amount of the reducing agent used is preferably 0.25 to 1.0 mole per mole of the compound of the general formula (XIII) or a salt thereof. This reaction may be conducted at a temperature of 0° to 30° C. for a period of 0.5 to 5 hours.

The thus obtained compound of the general formula (I) can be isolated and purified by a conventional procedure such as extraction, crystallization, column chromatography or the like. Also, the salt of the compound of the general formula (I) can be obtained by a procedure known per se.

Moreover, the compounds of the general formulas (III), (IV), (V), (VI), (VIIIa), (X) and (XII) which are the starting compounds for producing the compound of the present invention can be produced by, for example, the following method, a method known per se or a combination thereof:

(1) Production of the compound of the general formula (III)

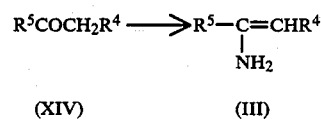

(XIV)    (III)

wherein $R^4$ and $R^5$ have the same meanings as defined above.

The compound of the general formula (III) can be produced by reacting the compound of the general formula (XIV) with ammonia according to the method described in, for example, J. Am. Chem. Soc. 67, 1019 (1945) or the like.

(2) Production of the compound of the general formula (V)

The compound of the general formula (V) can be produced by reacting the compound of the general formula (XIV) with the compound of the general formula (II) under the conditions described in, for example, Tetrahedron, Vol. 28, 663 (1972).

(3) Production of the compound of the general formula (VI)

The compound of the general formula (VI) can be produced by reacting the compound of the general formula (IV) with ammonia in the same manner as in (1) above.

(4) Production of the compounds of the general formulas (IV), (VIIIa) and (X) or salts thereof The compounds of the general formulas (IV), (VIIIa) and (X) or salts thereof can be produced by, for example, the following methods:

an alkanesulfonyl halide, for example, methanesulfonyl chloride, methanesulfonyl bromide or the like; an arenesulfonyl halide, for example, benzenesulfonyl chloride, p-toluenesulfonyl chloride or the like; or the like.

The compound of the general formula (XVII) can be produced by reacting the compound of the general formula (XVI) or (XVIa) with an alkylating agent such as an alkyl ester of halogenated fatty acid, for example, ethyl bromoacetate or the like; an alkyl ester of diazotized fatty acid, for example, ethyl diazoacetate or the like; or the like.

The compound of the general formula (VIII) or a salt thereof can be produced by subjecting the compound of the general formula (X) thus obtained to reaction with the compound of the general formula (XVIII) or sub-

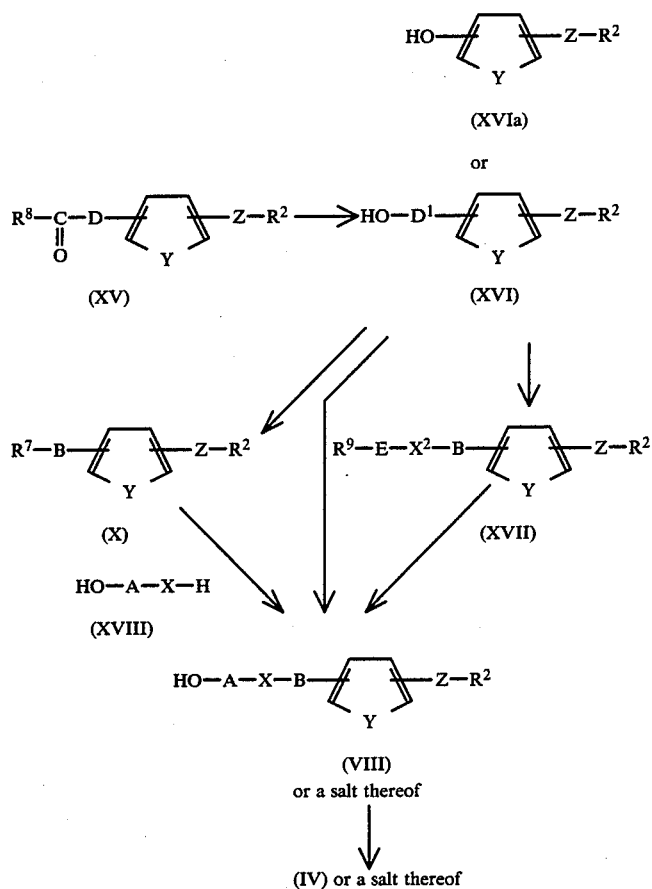

In the above formulas, $R^8$ represents a hydrogen atom or an alkoxy group; $R^9$ represents an alkoxycarbonyl group; $D^1$ represent the same alkylene or alkenylene groups as B; $X^2$ represents an oxygen atom; E represents an alkylene group; and $R^2$, $R^7$, A, B, D, X, Y and Z have the same meanings as defined above.

The compound of the general formula (XVI) can be produced by subjecting the compound of the general formula (XV) to conventional reduction reaction with a reducing agent, for example, lithium aluminum hydride, sodium boron hydride or the like.

The compound of the general formula (X) can be produced by reacting the compound of the general formula (XVI) or (XVIa) with a halogenating agent such as thionyl chloride, thionyl bromide, phosphorus tribromide or the like or with a sulfonyl halide such as jecting the compound of the general formula (XVII) to conventional reduction reaction with a reducing agent, for example, lithium aluminum hydride, sodium boron hydride or the like.

Furthermore, the compound of the general formula (VIII) or a salt thereof can be produced by reacting the compound of the general formula (XVI) with an epoxide such as ethylene oxide, propylene oxide, or the like. The compound of the general formula (IV) can be produced by reacting the compound of the general formula (VIII) with diketene or the like under the conditions described in, for example, J. Chem. Soc., 97, 1978 (1910) or the like.

Also, the compound of the general formula (VIII) in which Z is a methylene group, or a salt thereof can be produced by, for example, the following method:

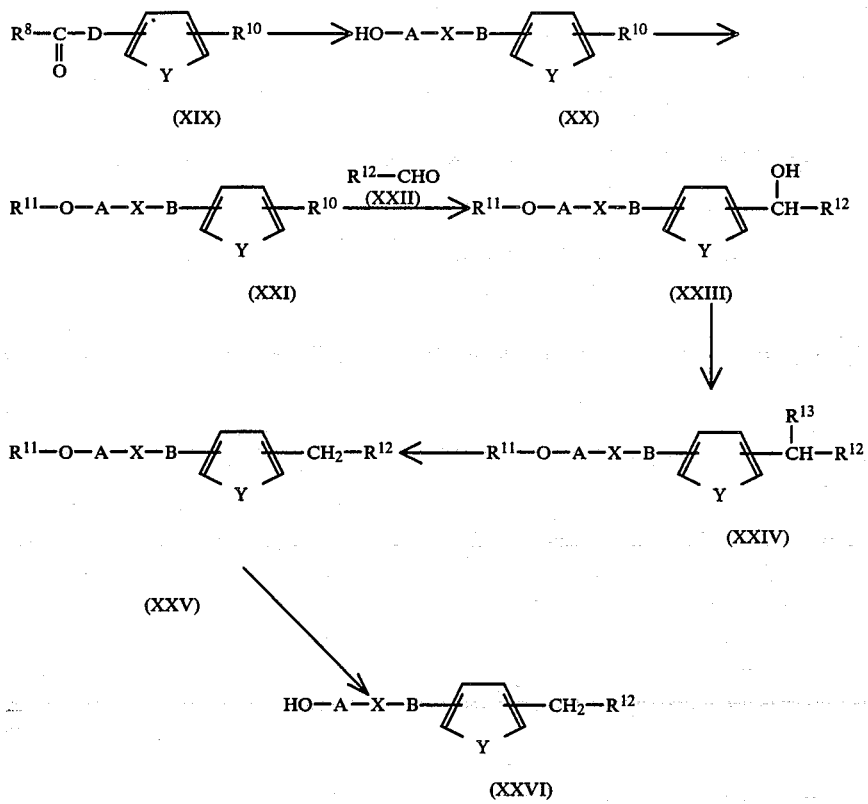

In the above formulas, $R^{10}$ represents a halogen atom, $R^{11}$ represents a hydroxyl-protecting group, $R^{12}$ represents a nitrogen-containing heterocyclic group bonded through one of the carbon atoms in the ring to the adjacent carbon atom, $R^{13}$ represents a halogen atom or an acetoxy group, and $R^8$, A, B, D, X and Y have the same meanings as defined above.

The compound of the general formula (XXIII) is produced from the compound of the general formula (XIX) in the same manner as in the above-mentioned production of the compound of the general formula (VIII) or a salt thereof from the compound of the general formula (XV).

The compound of the general formula (XXI) is obtained by subjecting the compound of the general formula (XX) to a conventional protecting group-forming reaction. The hydroxyl-protecting group includes those which are conventionally known as protecting groups for hydroxyl group, for example, tetrahydropyranyl group, tert-butyldimethylsilyl group, benzyl group and the like.

The compound of the general formula (XXIII) is produced by subjecting the compound of the general formula (XXI) and the compound of the general formula (XXII) to condensation reaction in the presence of, for example, n-butyllithium.

The compound of the general formula (XXIV) is produced by subjecting the compound of the general formula (XXIII) to halogenation reaction with a halogenating agent, for example, thionyl chloride or the like or to acetylation reaction with an acetylating agent, for example, acetic anhydride or the like.

The compound of the general formula (XXV) is produced by subjecting the compound of the general formula (XXIV) to reduction reaction, for example, with zinc powder in acetic acid.

By subjecting the thus obtained compound of the general formula (XXV) to a conventional hydroxyl-protecting group-removing reaction, a compound of the general formula (XXVI) is produced.

The above-mentioned protecting group-forming reaction, condensation reaction, halogenation reaction, acetylation reaction, reduction reaction and the protecting group-removing reaction are effected by the methods described in, for example, Protective Groups in Organic Synthesis (John Wiley & Sons), the second chapter; J. Med. Chem., 24, 1149 (1981); and the like.

Also, the compound of the general formula (VIIIb) which is the starting compound of the compound of this invention can be produced by the following method:

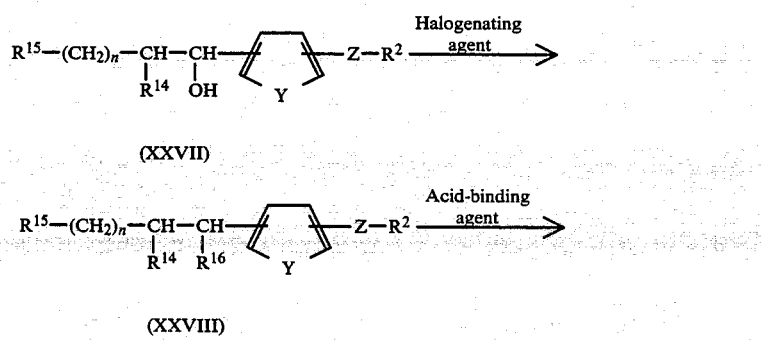

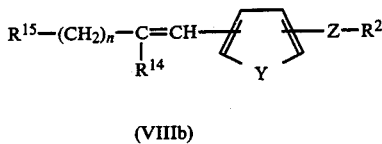

(VIIIb)

In the above formulas, $R^2$, Y and Z have the same meanings as defined above; $R^{14}$ represents a hydrogen atom or a lower alkyl group; $R^{15}$ represents a group of the formula $-OR^{17}$ in which $R^{17}$ represents a hydrogen atom or a hydroxyl-protecting group, or a group of the formula $-O-A^1-OR^{18}$ in which $R^{18}$ represents a hydrogen atom or a hydroxyl-protecting group; $A^1$ represents the same alkylene group as A; $R^{16}$ represents a halogen atom; and n is 1 or 2.

The above reaction can be carried out by the method known per se for producing olefins, for example, the method described in, for example, Compendium of Organic Synthetic Methods (John Wiley & Sons), Section 198 and Section 205. For example, the following method is used:

The reaction of the compound of the general formula (XXVII) with a halogenating agent to produce the compound of the general formula (XXVIII) may be carried out using the halogenating agent in an amount at least equimolar to the compound of the general formula (XXVII) at a temperature of $-20°$ to $120°$ C. for a period of several minutes to several tens of hours. Also, the above reaction may be effected in the presence or absence of a solvent, and the solvent used may be any solvent which does not adversely affect the reaction, and includes, for example, halogenated hydrocarbons such as methylene chloride, chloroform, carbon tetrachloride, 1,2-dichloroethane and the like; aromatic hydrocarbons such as benzene, toluene and the like; ethers such as diethyl ether, tetrahydrofuran, dioxane, 1,2-dimethoxyethane and the like; nitriles such as acetonitrile and the like; ketones such as acetone, methyl ethyl ketone, methyl isobutyl ketone and the like; esters such as methyl acetate, ethyl acetate, butyl acetate and the like; carboxylic acids such as acetic acid, dichloroacetic acid, trifluoroacetic acid and the like; alcohols such as methanol, ethanol, propanol, isopropanol, butanol, isobutanol and the like; amides such as N,N-dimethylformamide, N,N-dimethylacetamide, N-methylpyrrolidone and the like; amines such as pyridine, picoline, lutidine, N,N-dimethylaniline and the like; water; and the like. These solvents may be used alone or in admixture of two or more.

Also, the halogenating agent includes, for example, thionyl chloride, thionyl bromide, phosphorus oxychloride, phosphorus tribromide, phosphorus trichloride, oxalyl chloride, phosgene, carbon tetrachloride-triphenyl phosphine, bromine-triphenyl phosphine, hydrogen chloride, hydrogen bromide and the like.

The subsequent reaction of the compound of the general formula (XXVIII) with the acid-binding agent to produce the compound of the general formula (VIIIb) may be carried out using the acid-binding agent in an amount of 1 to 10 moles per mole of the compound of the general formula (XXVIII) at a temperature of room temperature to $200°$ C. for a period of several minutes to several tens of hours. The above reaction may be effected in the presence or absence of a solvent. The solvent used may be any solvent which does not adversely affect the reaction, and includes, for example, aromatic hydrocarbons such as benzene, toluene, xylene and the like; ethers such as tetrahydrofuran, dioxane, 1,2-dimethoxyethane and the like; nitriles such as acetonitrile and the like; ketones such as acetone, methyl ethyl ketone, methyl isobutyl ketone and the like; esters such as methyl acetate, ethyl acetate, butyl acetate and the like; carboxylic acids such as acetic acid and the like; alcohols such as methanol, ethanol, propanol, 2-propanol, butanol, isobutanol, tert-butanol and the like; amides such as N,N-dimethylformamide, N,N-dimethylacetamide, N-methylpyrrolidone and the like; sulfoxides such as dimethylsulfoxide and the like; hexamethylenephosphoramide; water; and the like. These solvents may be used alone or in admixture of two or more.

Moreover, the acid-binding agent includes, for example, organic bases such as 1,8-diazabicyclo[5,4,0]undec-7-ene (DBU), 1,5-diazabicyclo[4,3,0]non-5-ene (DBN), 1,4-diazabicyclo[2,2,2]octane (Dabco), triethylamine, pyridine, N,N-dimethylaniline and the like; alkali metal alkoxides such as sodium methoxide, sodium ethoxide, potassium tert-butoxide and the like; and inorganic bases such as sodium hydroxide, potassium hydroxide, sodium carbonate, sodium hydrogencarbonate and the like.

In a series of the reactions for producing the compound of the general formula (VIIIb) from the compound of the general formula (XXVII) through the compound of the general formula (XXVIII), the subsequent reaction may be carried out without isolating the compound of the general formula (XXVIII).

In addition, when in the compound of the general formula (VIIb) or (XXVIII), for example, $R^{17}$ and $R^{18}$ are hydroxyl-protecting groups $R^{15}$ can be converted into a hydroxyl group or a group of the formula $-O-A^1-OH$ in which $A^1$ has the same meaning as defined above, respectively, by subjecting the compound to the removal reaction of the hydroxyl-protecting group, or reversely, when $R^{15}$ is a hydroxyl group or a group of the formula $-O-A^1-OH$ in which $A^1$ has the same meaning as defined above, $R^{17}$ or $R^{18}$ can be converted into a hydroxyl-protecting group by subjecting the compound to the formation of a protecting group for the hydroxyl group. Incidentally, the removal reaction of the hydroxyl-protecting group and the formation of a protecting group for the hydroxyl group can be carried out by a known method, for example, by the method described in Protective Group in Organic Synthesis (John Wiley & Sons), the second chapter.

The removal of the protecting group, if the protecting group is, for example, a methyl group, can be effected by allowing aluminum chloride or iodotrimethylsilane to act thereon; if the protecting group is a benzyl, diphenylmethyl or triphenylmethyl group, the removal can be effected by allowing iodotrimethylsilane, acetic acid, trifluoroacetic acid or hydrochloric acid to act thereon or by subjecting the compound to hydrogenation; if the protecting group is a 1-ethoxyethyl or tetrahydropyranyl group the removal can be effected by allowing hydrochloric acid or p-toluenesulfonic acid to act thereon; if the protecting group is a formyl or acetyl group, the removal can be effected by allowing potassium hydrogencarbonate, sodium methoxide or hydrochloric acid to act thereon; and if the protecting group is a trimethylsilyl, or tert-butyldimethylsilyl group, the removal can be effected by allowing hydrochloric acid or tetrabutylammonium fluoride to act thereon.

The compound of the general formula (XXVII) can be produced by the following reactions:

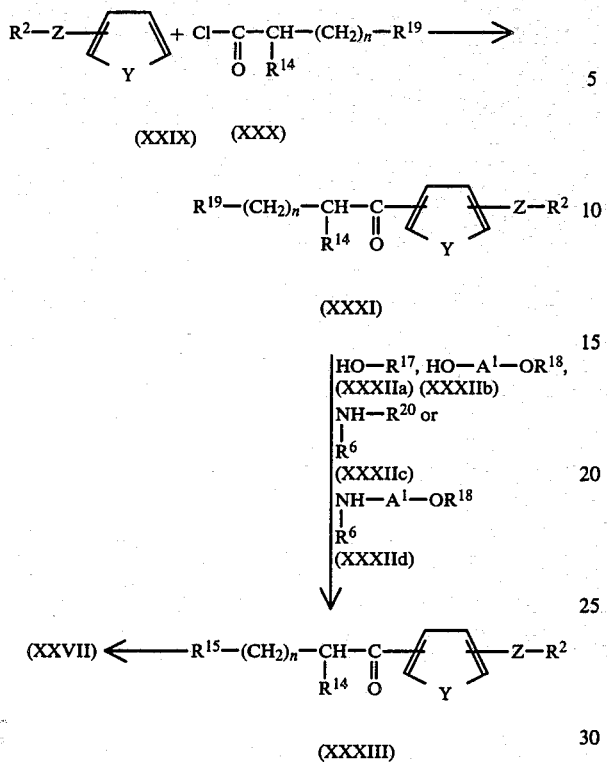

In the above formulas, $R^{19}$ represents a halogen atom; $R^{20}$ represents a hydrogen atom or amino-protecting group; $A^1$ represents the same alkylene group as A; and $R^2$, $R^6$, $R^{14}$, $R^{15}$, $R^{17}$, $R^{18}$, Y, Z and n have the same meanings as defined above.

That is, the compound of the general formula (XXVII) can be produced by subjecting the compound of the general formula (XXIX) and the compound of the general formula (XXX) to conventional Friedel-Crafts reaction, reacting the resulting compound of the general formula (XXXI) with the compound of the general formula (XXXIIa), (XXXIIb), (XXXIIc) or (XXXIId) under the conditions which are usually applied to a halogen atom-substitution reaction, and thereafter, reducing the reaction product thus obtained with a reducing agent such as sodium boron hydride, sodium boron cyanohydride or the like in the conventional manner. The Friedel-Crafts reaction is effected in the presence of a catalyst which is usually used in the Friedel-Crafts reaction such as aluminum chloride, boron trifluoride, zinc chloride, stannic chloride, trifluoromethanesulfonic acid or the like.

Next, the pharmacological activities of typical compounds of this invention are described below.

Compounds to be tested 1. 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate
2. 3-[2-[N-methyl-N-[(E)-3-[4-(pyridin-3-ylmethyl)phenyl]-2-methylallyl]amino]ethyl]5-methyl, 2,6-dimethyl-4-(3-nitrophenyl)-1,4-dihydropyridine-3,5-dicarboxylate
3. 3-[2-[N-methyl-[(E)-3-[4-(pyridin-3-ylmethyl)phenyl]-2-methylallyl]amino]ethyl]5-(2-methoxy)ethyl 2,6-dimethyl-4-(3-nitrophenyl)-1,4-dihydropyridine-3,5-dicarboxylate
4. 3-[2-[N-methyl-N-[(E)-3-[4-(pyridin-3-ylmethyl)phenyl]-2-methylallyl]amino]ethyl]5-ethyl 2,6-dimethyl-4-(3-nitrophenyl)-1,4-dihydropyridine-3,5-dicarboxylate
5. 3-[2-[N-methyl-N-[(E)-3-[4-(pyridin-3-ylmethyl)phenyl]-2-methylallyl]amino]ethyl]5-isopropyl 2,6-dimethyl-4-(2,3-dichlorophenyl)-1,4-dihydropyridine-3,5-dicarboxylate
6. 3-[2-[N-methyl-N-[(E)-3-[4-(pyridin-3-ylmethyl)phenyl]-2-methylallyl]amino]ethyl]5-isopropyl 2,6-dimethyl-4-(2-trifluoromethylphenyl)-1,4-dihydropyridine-3,5-dicarboxylate
7. 3-[2-[N-methyl-N-[(E)-3-[4-(pyridin-3-ylmethyl)phenyl]allyl]amino]ethyl]5-isopropyl 2,6-dimethyl-4-(3-nitrophenyl)-1,4-dihydropyridine-3,5-dicarboxylate
8. 3-[2-[N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate
9. 3-[2-[N-methyl-N-[3-[4-(imidazol-1-ylmethyl)phenyl]allyl]amino]ethyl]5-isopropyl 2,6-dimethyl-4-(3-nitrophenyl)-1,4-dihydropyridine-3,5-dicarboxylate
10. 3-[2-[N-methyl-N-[(E)-3-[4-(pyridin-3-yloxy)phenyl]-2-methylallyl]amino]ethyl]5-ethyl 2,6-dimethyl-4-(3-nitrophenyl)-1,4-dihydropyridine-3,5-dicarboxylate
11. 3-[2-[3-[4-(Imidazol-1-ylmethyl)phenyl]propyloxy]ethyl]5-ethyl 2,6-dimethyl-4-(3-nitrophenyl)-1,4-dihydropyridine-3,5-dicarboxylate
12. 3-[2-[(E)-3-[4-(pyridin-3-ylmethyl)phenyl]-2-methylallyloxy]ethyl]5-ethyl 2,6-dimethyl-4-(3-nitrophenyl)-1,4-dihydropyridine-3,5-dicarboxylate
13. 3-[2-[(E)-3-[4-(imidazol-1-ylmethyl)phenyl]allyloxy]ethyl]5-ethyl 2,6-dimethyl-4-(3-nitrophenyl)-1,4-dihydropyridine-3,5-dicarboxylate
14. 3-[2-[4-(Imidazol-1-ylmethyl)benzyloxy]ethyl]5-ethyl 2,6-dimethyl-4-(3-nitrophenyl)-1,4-dihydropyridine-3,5-dicarboxylate
15. 3-[2-[4-(Pyridin-3-ylmethyl)benzyloxy]ethyl]5-ethyl 2,6-dimethyl-4-(3-nitrophenyl)-1,4-dihydropyridine-3,5-dicarboxylate
16. 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate
17. 3-[2-[(E)-3-[4-(pyridin-3-ylmethyl)phenyl]-2-methylallyloxy]ethyl]5-methyl 2,6-dimethyl-4-(3-nitrophenyl)-1,4-dihydropyridine-3,5-dicarboxylate
18. 3-[2-[3-[4-(Pyridin-3-ylmethyl)phenyl]propyloxy]ethyl]5-ethyl 2,6-dimethyl-4-(3-nitrophenyl)-1,4-dihydropyridine-3,5-dicarboxylate
19. 3-[2-[(E)-3-[4-(pyridin-3-yloxy)phenyl]-2-methylallyloxy]ethyl]5-ethyl 2,6-dimethyl-4-(3-nitrophenyl)-1,4-dihydropyridine-3,5-dicarboxylate
20. 3-[2-[3-[4-(Pyridin-3-yloxy)phenyl]propyloxy]ethyl]-5-ethyl 2,6-dimethyl-4-(3-nitrophenyl)-1,4-dihydropyridine-3,5-dicarboxylate
21. 3-[2-[(E)-3-[5-(pyridin-3-ylmethyl)thiophen-2-yl]-2-methylallyloxy]ethyl]5-ethyl 2,6-dimethyl-4-(3-nitrophenyl)-1,4-dihydropyridine-3,5-dicarboxylate
22. 3-[2-[(E)-3-[4-(pyridin-3-ylmethyl)phenyl]allyloxy]ethyl]5-methyl 2,6-dimethyl-4-(3-nitrophenyl)-1,4-dihydropyridine-3,5-dicarboxylate
23. 3-[2-[(E)-3-[4-(pyridin-3-ylmethyl)phenyl]allyloxy]ethyl]5-[2-(N-benzyl-N-methylamino)ethyl] 2,6- dimethyl-4-(3-nitrophenyl)-1,4-dihydropyridine-3,5-dicarboxylate
24. 3-[2-[(E)-3-[4-(pyridin-3-ylmethyl)phenyl]allyloxy]ethyl]5-isopropyl 2,6-dimethyl-4-(3-nitrophenyl)-1,4-dihydropyridine-3,5-dicarboxylate
25. 3-[2-[(E)-3-[4-(pyridin-3-ylmethyl)phenyl]allyloxy]ethyl]5-methyl 2,6-dimethyl-4-(2,3-dichlorophenyl)-1,4-dihydropyridine-3,5-dicarboxylate
26. 3-[2-[(E)-3-[4-(pyridin-3-ylmethyl)phenyl]allyloxy]ethyl]5-methyl 2,6-dimethyl-4-(2-trifluoromethylphenyl)-1,4-dihydropyridine-3,5-dicarboxylate
27. 3-[2-[2-[4-(Pyridin-3-ylmethyl)phenyl]ethyloxy]ethyl]5-ethyl 2,6-dimethyl-4-(3-nitrophenyl)-1,4-dihydropyridine-3,5-dicarboxylate
28. 3-[2-[(E)-3-[4-(pyridin-3-ylmethyl)phenyl]allylthio]ethyl]5-ethyl 2,6-dimethyl-4-(3-nitrophenyl)-1,4-dihydropyridine-3,5-dicarboxylate
29. 3-[2-[(E)-3-[4-(pyridin-3-ylmethyl)phenyl]-2-methylallyloxy]ethyl]5-isopropyl 2,6-dimethyl-4-(3-nitrophenyl)-1,4-dihydropyridine-3,5-dicarboxylate
30. 3-[4-[(E)-3-[4-(pyridin-3-ylmethyl)phenyl]-2-methylallyloxy]butyl]5-ethyl 2,6-dimethyl-4-(3-nitrophenyl)-1,4-dihydropyridine-3,5-dicarboxylate
31. 3-[3-[(E)-3-[4-(pyridin-3-ylmethyl)phenyl]-2-methylallyloxy]-2-methylpropyl]5-ethyl 2,6-dimethyl-4-(3-nitrophenyl)-1,4-dihydropyridine-3,5-dicarboxylate
32. 3-[3-[(E)-3-[4-(pyridin-3-ylmethyl)phenyl]-2-methylallyloxy]-2,2-dimethylpropyl]5-methyl-2,6-dimethyl-4-(3-nitrophenyl)-1,4-dihydropyridine-3,5-dicarboxylate
33. 3-[3-[(E)-3-[4-(pyridin-3-ylmethyl)phenyl]-2-methylallyloxy]-2,2-dimethylpropyl]5-ethyl 2,6-dimethyl-4-(3-nitrophenyl)-1,4-dihydropyridine-3,5-dicarboxylate Nicardipine: 3-[2-(N-benzyl-N-methylamino)ethyl]5-methyl 2,6-dimethyl-4-(3-nitrophenyl)-1,4-dihydropyridine-3,5-dicarboxylate hydrochloride OKY-1581: Sodium (E)-3-[4-(pyridin-3-ylmethyl)phenyl]-2-methylpropenoate The compounds of this invention to be tested were used in the form of a hydrochloride.

1. Coronary vasodilating activity

The heart of a guinea pig (Hartley strain, male, 500–700 g, 3 heads per group) was isolated and set in the Landendorff perfusing apparatus. About 0.5% defibrinated blood was fed to the apparatus, and the Krebs bicarbonate solution, into which a mixed gas consisting of 95% of $O_2$ and 5% of $CO_2$ had been bubbled was perfused over the heart, after which a 1 mg/ml solution of the test compound in an aqueous solution containing 10% by volume of dimethylsulfoxide and 10% of polyoxyethylfatty acid glyceride [Cremophor EL manufactured by Sigma] was prepared, diluted with a saline solution to the desired concentration, and then administered into the heart in an amount of 0.1 ml through the rubber tube attached to the cannula inserted retrogressively into the aorta. The vasodilating activity was determined by measuring the amount of the solution effluent from the coronary vessel after passing through the aorta by means of an electric drop counter (universal drop counter manufactured by Natsume Seisakusho) and indicated as $ED_{50}$ value which is the amount necessary for the amount of the effluent solution to increase 50% as compared with those before addition of the test compound.

The results obtained are shown in Table 1.

TABLE 1

| Test compounds | $ED_{50}$ (μg/i.c.) |
|---|---|
| 12 | 0.026 |
| 13 | 0.036 |
| 14 | 0.023 |
| 15 | 0.0092 |
| 16 | 0.0105 |
| 17 | 0.012 |
| 18 | 0.026 |
| 19 | 0.017 |
| 20 | 0.024 |
| 22 | 0.016 |
| 23 | 0.019 |
| 29 | 0.019 |
| Nicardipine | 0.042 |

2. Vertebral Artery Blood Flow Increasing Activity

The vertebral artery blood flow of a dog (mongrel, 12–22 kg, 2–3 heads per group) anesthetized with pentobarbital sodium (30 mg/kg, i.v.) was measured by means of an electromagnetic flow meter (MFV-2100 manufactured by Nihon Kohden Kogyo). The amount of the test compound necessary to exhibit the same activity as 1 mg/kg (i.v.) of papaverine hydrochloride was determined, and the ratio thereof to the amount of papaverine hydrochloride (1 mg/kg) was calculated and indicated as the effect ratio.

The test compounds 1, 3 and 10 were adjusted to a concentration of 1 mg/ml with distilled water, and then diluted with a saline solution to the desired concentrations, after which the thus diluted solutions were intravenously administered, and the test compounds 12, 15, 18, 19, 20, 24, 29, 30, 32 and 33 were formed into solutions in the same manner as in Item 1 above and then intravenously administered.

The results obtained are shown in Table 2.

TABLE 2

| Test Compound | Effect ratio |
|---|---|
| 1 | 238 |
| 3 | 385 |
| 10 | 641 |
| 12 | 345 |
| 15 | 238 |
| 18 | 233 |
| 19 | 550 |
| 20 | 535 |
| 24 | 286 |
| 29 | 426 |
| 30 | 397 |
| 32 | 417 |
| 33 | 333 |
| Nicardipine | 220 |

3. Thromboxane-Synthesizing Enzyme-Inhibitory Activity

To a rat (Wistar strain, male, 300–350 g, 4 heads per group) which had been starved overnight was orally administered a test compound solution, and blood was collected from the abdominal aorta using citric acid after one hour. Two milliliters of a $1 \times 10^9$/ml platelet-rich plasma (PRP) was preincubated at 37° C. for 2 minutes. Subsequently, 0.1 ml of 10 mM sodium archidonate was added, and the resulting mixture was subjected to reaction for 6 minutes, after which indomethacin was added thereto to terminate the reaction. The reaction mixture was subjected to deproteinization treatment and reacted with thiobarbituric acid (TBA) reagent, after which the reaction mixture was subjected to extraction with 3 ml of n-butanol. The resulting extract was subjected to colorimetry (λ=532 nm) to determine the amount of malondialdehyde (MDA) produced. As to the platelet-poor plasma (PPP) obtained from the same rat as above, the same procedure as above was repeated to determine the amount of MDA produced, and the difference between the two is indicated as MDA value. Comparing with the MDA values of the control group, the MDA production-inhibition (%) was determined.

The test compounds 1-9 were adjusted to the desired concentrations with water and the test compounds 11-33 and nicardipine were adjusted to a concentration of 5 mg/ml with an aqueous solution containing 10% of each of dimethyl sulfoxide and Cremophor and then diluted with water to the desired concentrations.

The results obtained are shown in Table 3.

TABLE 3

| Test Compound | Dosage (mg/kg) | MDA production-inhibition (%) |
|---|---|---|
| 1 | 3 | 59.4 |
| 2 | 3 | 63.2 |
| 3 | 3 | 65.8 |
| 4 | 3 | 53.6 |
| 5 | 3 | 57.9 |
| 6 | 3 | 60.6 |
| 7 | 3 | 52.8 |
| 8 | 3 | 64.9 |
| 9 | 3 | 47.2 |
| 11 | 3 | 37.8 |
| 12 | 3 | 48.1 |
| 13 | 3 | 47.2 |
| 16 | 3 | 31.6 |
| 17 | 3 | 58.6 |
| 18 | 3 | 40.9 |
| 27 | 3 | 35.7 |
| 28 | 3 | 31.2 |
| 29 | 3 | 56.8 |
| 31 | 3 | 50.5 |
| 33 | 3 | 41.5 |
| Nicardipine | 3 | 2.7 |

4. Antithrombosis activity (activity against mouse pulmonary infraction model)

According to the G. DiMinno and M. J. Silver method [J. Pharmacol. Exp. Therap., 225 (1) 57-60 (1983)], a solution of the compound to be tested was orally administered to a mouse (ICR strain, male, 4 weeks old), and 0.15 ml of a mixed solution of epinephrine (100 μM) and collagen (150 μg/ml) was intravenously administered to the mouse after one hour, after which the paralytic time was measured. Comparing the paralytic time of the control group, the paralytic time-shortening percentage due to the compound to be tested was determined. The results obtained are shown in Table 4, in which the case where the paralytic time was 15 minutes was calculated as death.

Moreover, the same experiment was repeated, except that 0.10 ml of a mixed solution of epinephrine (100 μM) and collagen (150 μg/ml) was intravenously administered to the mouse and the effect of preventing the appearance of death and a case where the paralytic time was 10 minutes or more was checked and the results thereof are shown in Table 5.

The test compounds shown in Table 4 were adjusted to the desired concentrations with water, and the test compounds shown in Table 5 were adjusted to a concentration of 5 mg/ml with an aqueous solution containing 10% by volume of each of dimethyl sulfoxide and Cremophor, and then diluted with water to the desired concentrations.

TABLE 4

| Test compound | Number of mice tested | Dosage (mg/kg) | Paralytic time-shortening percentage (%) |
|---|---|---|---|
| 1 | 10 | 10 | 52.3 |
| 2 | 10 | 10 | 84.1 |
| 4 | 10 | 10 | 38.6 |
| 5 | 10 | 10 | 93.9 |
| 6 | 10 | 10 | 87.9 |
| 7 | 10 | 10 | 36.4 |
| 8 | 10 | 10 | 47.9 |
| 10 | 10 | 10 | 79.2 |
| Nicardipine | 10 | 10 | 6.3 |
| OKY-1581 | 10 | 300 | 9.5 |

TABLE 5

| Test compound | Number of mice tested | Dosage (mg/kg) | Preventive percentage of death + paralysis for 10 minutes or more (%) |
|---|---|---|---|
| Control | 35 | — | 25.7 |
| 12 | 18 | 10 | 77.8 |
| 17 | 8 | 10 | 100.0 |
| 19 | 9 | 10 | 77.8 |
| 20 | 10 | 10 | 70.0 |
| 21 | 10 | 10 | 80.0 |
| 24 | 10 | 10 | 90.0 |
| 26 | 10 | 10 | 90.0 |
| 27 | 9 | 10 | 77.8 |
| 29 | 10 | 10 | 90.0 |
| Nicardipine | 10 | 10 | 0 |
| OKY-1581 | 10 | 30 | 10.0 |

Acute Toxicity

The $LD_{50}$ values obtained by intravenous administration of the test compounds numbered as 2, 7, 8, 9 and 10 to mice (ICR strain, male, 4 weeks old, 5 heads per group) were at least 30 mg/kg, the $LD_{50}$ value obtained by intravenous administration of the test compound numbered as 30 was at least 50 mg/kg, and the $LD_{50}$ values obtained by intravenous administration of the test compounds numbered as 12, 16, 17, 19 and 21 were at least 75 mg/kg.

From the above results, it can easily be understood that the compounds of this invention have an excellent vasodilating activity and a platelet aggregation inhibiting activity based on thromboxane-synthesizing enzyme-inhibitory activity, namely an antithrombosis activity, and have a low toxicity.

Accordingly, the compound of this invention is a compound useful as a drug for curing circulation disturbance.

When the compound of this invention is used as a medicine, the compound can be orally or parenterally administered as it is or in admixture with an additive such as a pharmaceutically acceptable excipient, carrier or diluent in the form of tablets, capsules, granules, patches, sublingnal tablets, external preparations, powder or injection. The dosage of the compound, when administered orally, is usually about 10 to 600 mg per adult a day, and this amount is administered at one time or in several portions, and may be varied depending upon the age, weight and symptom of a patient.

DESCRIPTION OF THE PREFERRED EMBODIMENTS

This invention is explained in more detail below referring to Examples and Preparation Examples; however, this invention is not limited thereto.

Example 1

In 200 ml of anhydrous diethyl ether was dissolved 24.0 g of ethyl (E)-3-[4-(pyridin-3-ylmethyl)phenyl]acrylate, and thereto was added in small portions 2.4 g of lithium aluminum hydride with ice-cooling over one hour. The resulting mixture was subjected to reaction for one hour with ice-cooling and then for a further one hour at room temperature, after which 91 ml of hydrous tetrahyrofuran (water content: 10% by volume) was added in small portions. Insolubles were removed by filtration and the solvent was removed by distillation under reduced pressure. The resulting oily product was dissolved in 200 ml of chloroform, and 40 ml of water was added to the resulting solution, after which the pH thereof was adjusted to 7 with 2N hydrochloric acid. The organic layer was separated, washed successively with 50 ml of water and 50 ml of a saturated aqueous sodium chloride solution, and then dried over anhydrous sodium sulfate, after which the solvent was removed by distillation under reduced pressure. The residue thus obtained was purified by a column chromatography [Wako Silica Gel C-200, eluant: benzene:ethyl acetate (1:1 by volume)] to obtain 10.5 g (yield 52.0%) of colorless, oily (E)-3-[4-(pyridin-3-ylmethyl)phenyl]allyl alcohol. This was crystallized from a mixed solvent of chloroform and diethyl ether to obtain colorless needle crystals having a melting point of 81°-82° C.

IR (KBr) cm$^{-1}$: 3240.

NMR (CDCl$_3$) δ values: 3.85 (2H, s), 4.23 (1H, s), 4.27 (2H, d, J=4.5 Hz), 6.28 (1H, dt, J=16 Hz, 4.5 Hz), 6.50 (1H, d, J=16 Hz), 6.85-7.55 (6H, m), 8.20-8.51 (2H, m).

In the same manner as above, the following compounds were obtained:

(E)-3-[4-(pyridin-3-ylmethyl)phenyl]-2-methylallyl alcohol (colorless and oily)

IR (film) cm$^{-1}$: 3350-3230.

NMR (CDCl$_3$) δ values: 1.92 (3H, bs), 3.98 (2H, s), 4.25 (3H, bs), 6.63 (1H, bs), 6.90-7.68 (6H, m), 8.40-8.70 (2H, m).

(E)-3-[5-(pyridin-3-ylmethyl)thiophen-2-yl]-2-methylallyl alcohol (colorless needle crystals)

Melting point: 79°-80° C.

IR (KBr) cm$^{-1}$: 3275.

NMR (CDCl$_3$) δ values: 1.88 (3H, s), 4.01 (2H, s), 4.11 (2H, bs), 4.59 (1H, bs), 6.42-7.57 (5H, m), 8.21-8.42 (2H, m).

(E)-3-[4-(pyridin-3-yloxy)phenyl]-2-methylallyl alcohol (colorless and oily)

IR (film) cm$^{-1}$: 3500-3100, 1600.

NMR (CDCl$_3$) δ values: 1.89 (3H, s), 3.50 (1H, bs), 4.16 (2H, s), 6.46 (1H, s), 6.82-7.36 (6H, m), 8.20-8.42 (2H, m).

4-(Imidazol-1-ylmethyl)benzyl alcohol (colorless needle crystals)

Melting point: 72°-73° C.

IR(KBr) cm$^{-1}$: 3100.

NMR (CDCl$_3$) δ values: 4.69 (2H, s), 5.04 (2H, s), 5.97 (1H, s), 6.85-7.47 (7H, m).

3-[4-(Imidazol-1-ylmethyl)phenyl]propanol (colorless and oily)

IR (film) cm$^{-1}$: 3300.

NMR (CDCl$_3$) δ values: 1.57-2.12 (2H, m), 2.58-2.82 (2H, m), 3.50-3.70 (2H, m), 4.35 (1H, s), 4.95 (2H, s), 6.70-7.50 (7H, m).

2-[4-(Pyridin-3-ylmethyl)phenyl]ethanol (colorless and oily)

IR (film) cm$^{-1}$: 3270.

NMR (CDCl$_3$) δ values: 2.85 (2H, t, J=7 Hz), 3.88 (2H, t, J=7 Hz), 3.95 (2H, s), 4.36 (1H, s), 6.52-7.82 (6H, m), 8.22-8.63 (2H, m).

(E)-3-[4-(pyridin-4-ylmethyl)phenyl]allyl alcohol

Melting point: 66°-69° C.

IR (KBr) cm$^{-1}$: 3200, 1595.

NMR (CDCl$_3$) δ values: 3.83 (2H, s), 4.24 (2H, d, J=4.5 Hz), 4.30 (1H, s), 6.28 (1H, dt, J=16 Hz, 4.5 Hz), 6.50 (1H, d, J=16 Hz), 6.80-7.35 (6H, m), 8.20-8.50 (2H, m).

Example 2

In 36 ml of anhydrous diethyl ether was dissolved 1.6 g of anhydrous aluminum chloride, and to the resulting solution was added 1.3 g of lithium aluminum hydride in small portions with ice-cooling over 10 minutes. The resulting mixture was stirred at room temperature for 30 minutes, and to the solution thus obtained was added dropwise a solution of 5.9 g of ethyl (E)-3-[4-(imidazol-1-ylmethyl)phenyl]acrylate in 48 ml of anhydrous tetrahydrofuran with ice-cooling over 30 minutes, after which the resulting mixture was subjected to reaction at room temperature for one hour. Subsequently, 50 ml of hydrous tetrahydrofuran (water content: 10% by volume) was added thereto with ice-cooling, and insolubles were removed by filtration and then washed with five 20-ml portions of methanol. The washings were combined with the filtrate, and the solvent was removed by distillation under reduced pressure. To the resulting oily product were added 100 ml of chloroform and 50 ml of water to form a solution. The organic layer was separated, washed successively with 50 ml of water and 50 ml of a saturated aqueous sodium chloride solution, and thereafter dried over anhydrous sodium sulfate. The solvent was removed by distillation under reduced pressure, and the residue thus obtained was purified by a column chromatography [Wako Silica Gel C-200, eluant: chloroform:ethanol (20:1 by volume)] to obtain 4.0 g (yield 81.3%) of colorless, oily (E)-3-[4-(imidazol-1-ylmethyl)phenyl]allyl alcohol. This was crystallized from a mixed solvent of methylene chloride and diisopropyl ether to obtain colorless needle crystals having a melting point of 97°-99° C.

IR (KBr) cm$^{-1}$: 3170.

NMR (CDCl$_3$) δ values: 4.29 (2H, d, J=4.5 Hz), 4.50 (1H, s), 5.01 (2H, s), 6.08-7.46 (9H, m).

Example 3

In 10 ml of ethanol was dissolved 500 mg of (E)-3-[4-(pyridin-3-ylmethyl)phenyl]allyl alcohol, and to the resulting solution was added 100 mg of 5% palladium-carbon, and the resulting mixture was stirred at room temperature in a hydrogen atmosphere for 2.5 hours. The reaction mixture thus obtained was filtered and the filtrate thus obtained was concentrated under reduced pressure to obtain 500 mg (yield 99.1%) of colorless, oily 3-[4-(pyridin-3-ylmethyl)phenyl]propanol.

IR (film) cm$^{-1}$: 3300.

NMR (CDCl$_3$) δ values: 1.62-2.14 (2H, m), 2.51-2.84 (2H, m), 3.50-3.97 (4H, m), 5.51 (1H, bs), 6.82-7.55 (6H, m), 8.16-8.60 (2H, m).

Example 4

(1) In 100 ml of methylene chloride was dissolved 10.5 g of (E)-3-[4-(pyridin-3-ylmethyl)phenyl]allyl alcohol, and 17 ml of thionyl chloride was added dropwise to the resulting solution with ice-cooling, after which the resulting mixture was subjected to reaction under reflux for 30 minutes. The solvent and the excessive thionyl chloride were removed by distillation under reduced pressure, to obtain (E)-3-[4-(pyridin-3-ylmethyl)phenyl]allyl chloride hydrochloride as the residue. This residue was dissolved in 40 ml of dimethyl sulfoxide.

(2) To 100 ml of ethylene glycol was added 25 g of potassium tert-butoxide in portions at room temperature with stirring. To this solution was dropwise added the dimethyl sulfoxide solution obtained in (1) above at the same temperature, and the resulting mixture was then subjected to reaction at 50° C. for one hour. Subsequently, 400 ml of water was added to the reaction mixture with ice-cooling, and the pH thereof was adjusted to 7 with 6N hydrochloric acid, after which the mixture was subjected to extraction with 200 ml of ethyl acetate. The extract was washed successively with 200 ml of water and 100 ml of a saturated aqueous sodium chloride solution, and dried over anhydrous magnesium sulfate. The solvent was removed by distillation under reduced pressure, and the residue thus obtained was purified by a column chromatography [Wako Silica Gel C-200, eluant: benzene:ethyl acetate (1:2 by volume)], to obtain 5.4 g (yield 43.2%) of colorless, oily 2-[(E)-3-[4-(pyridin-3-ylmethyl)phenyl]allyloxy]ethanol.

IR (film) cm$^{-1}$: 3270.

NMR (CDCl$_3$) δ values: 3.45–4.00 (7H, m), 4.15 (2H, d, J=5 Hz), 6.25 (1H, dt, J=16 Hz, 5 Hz), 6.54 (1H, d, J=16 Hz), 6.95–7.60 (6H, m), 8.30–8.60 (2H, m).

In the same manner as above, the following compounds were obtained:

2-[(E)-3-[4-(pyridin-3-ylmethyl)phenyl]-2-methylallyloxy]ethanol (colorless and oily)
IR (film) cm$^{-1}$: 3350.
NMR (CDCl$_3$) δ values:

| 1.93 (3H, bs), 3.33–4.20 (m) 3.98 (s) 4.14 (s) | (8H), |
|---|---|

4.35 (1H, s), 6.59 (1H, bs), 6.95–7.83 (6H, m), 8.35–8.75 (2H, m)

2-[(E)-3-[5-(pyridin-3-ylmethyl)thiophen-2-yl]-2-methylallyloxy]ethanol (colorless and oily)
IR (CHCl$_3$) cm$^{-1}$: 3350–3200.
NMR (CDCl$_3$) δ values: 1.92 (3H, s), 3.20–3.90 (5H, m), 4.02 (2H, s), 4.09 (2H, s), 6.41–7.62 (5H, m), 8.30–8.54 (2H, m).

2-[(E)-3-[4-(pyridin-3-yloxy)phenyl]-2-methylallyloxy]ethanol (colorless and oily)
IR (film) cm$^{-1}$: 3500–3150.
NMR (CDCl$_3$) δ values: 1.89 (3H, s), 2.80 (1H, s), 3.40–3.90 (4H, m), 4.05 (2H, s), 6.42 (1H, s), 6.82–7.40 (6H, m), 8.15–8.48 (2H, m).

2-[4-(Imidazol-1-ylmethyl)benzyloxy]ethanol (colorless and oily)
IR (film) cm$^{-1}$: 3110.
NMR (CDCl$_3$) δ values: 3.53–3.92 (4H, m), 4.04 (1H, s), 4.63 (2H, s), 5.14 (2H, s), 6.91–7.59 (7H, m).

2-[(E)-3-[4-(imidazol-1-ylmethyl)phenyl]allyloxy]ethanol (colorless crystals)
Melting point: 70°–71° C.
IR (KBr) cm$^{-1}$: 3200–3100.
NMR (CDCl$_3$) δ values: 3.44–3.98 (4H, m), 4.12 (2H, d, J=4 Hz), 4.24 (1H, s), 5.07 (2H, s), 6.04–7.76 (9H, m).

2-[4-(Pyridin-3-ylmethyl)benzyloxy]ethanol (colorless and oily)
IR (film) cm$^{-1}$: 3400–3200.
NMR (CDCl$_3$) δ values:

| 3.28 (1H, bs), 3.38–4.03 (m) 3.90 (s) | (6H), |
|---|---|

4.51 (2H, s), 6.80–7.78 (6H, m), 8.20–8.63 (2H, m).

2-[(E)-3-[4-(pyridin-4-ylmethyl)phenyl]allyloxy]ethanol
Melting point: 71°–72° C.
IR (KBr) cm$^{-1}$: 3200, 1595.
NMR (CDCl$_3$) δ values: 3.33–3.96 (7H, m), 4.13 (2H, d, J=5 Hz), 6.28 (1H, dt, J=16 Hz, 5 Hz), 6.50 (1H, d, J=16 Hz), 6.75–7.36 (6H, m), 8.14–8.48 (2H, m).

(3) The same procedure as in (2) above was repeated, except that trimethylene glycol, diethylene glycol or propylene glycol was substituted for the ethylene glycol to obtain the following compounds:

3-[(E)-3-[4-(pyridin-3-ylmethyl)phenyl]allyloxy]propanol (colorless and oily)
IR (film) cm$^{-1}$: 3420–3360.
NMR (CDCl$_3$) δ values: 1.82 (2H, dt, J=12 Hz, 6 Hz), 2.81 (1H, bs),

| 3.43–3.99 (m) 3.90 (s) | (6H), |
|---|---|

4.08 (2H, d, J=5 Hz), 6.13 (1H, dt, J=16 Hz, 5 Hz), 6.56 (1H, d, J=16 Hz), 6.90–7.53 (6H, m), 8.23–8.53 (2H, m).

2-[2-[(E)-3-[4-(pyridin-3-ylmethyl)phenyl]allyloxy]ethyloxy]ethanol (colorless and oily)
IR (film) cm$^{-1}$: 3410–3340.
NMR (CDCl$_3$) δ values: 3.36 (1H, bs), 3.44–3.81 (8H, m), 3.91 (2H, s), 4.14 (2H, d, J=5 Hz), 6.14 (1H, dt, J=16 Hz, 5 Hz), 6.57 (1H, d, J=16 Hz), 6.86–7.56 (6H, m), 8.24–8.51 (2H, m).

2-[(E)-3-[4-(pyridin-3-ylmethyl)phenyl]allyloxy]-1-methylethanol (colorless and oily)
IR (film) cm$^{-1}$: 3420–3370.
NMR (CDCl$_3$) δ values: 1.15 (3H, d, J=6 Hz), 2.86 (1H, bs), 3.19–3.60 (3H, m), 3.92 (2H, s), 4.14 (2H, d, J=5 Hz), 6.14 (1H, dt, J=16 Hz, 5 Hz), 6.57 (1H, d, J=16 Hz), 6.54–6.89 (6H, m), 8.27–8.52 (2H, m).

(4) The same procedure as in (2) above was repeated, except that sodium hydride was used in place of the potassium tert.-butoxide to obtain the following compounds:

3-[(E)-3-[4-(pyridin-3-ylmethyl)phenyl]-2-methylallyloxy]-2,2-dimethylpropanol (colorless and oily)
IR (film) cm$^{-1}$: 3350.
NMR (CDCl$_3$) δ values: 0.95 (6H, s), 1.85 (3H, bs), 3.26 (2H, s), 3.45 (2H, s), 3.71 (1H, bs), 3.92 (2H, s), 3.96 (2H, s), 6.40 (1H, bs), 6.95–7.55 (6H, m), 8.26–8.50 (2H, m).

5-[(E)-3-[4-(pyridin-3-ylmethyl)phenyl]-2-methylallyloxy]pentanol (colorless and oily)
IR (film) cm$^{-1}$: 3500–3100.

NMR (CDCl₃) δ values: 1.26–1.80 (6H, m), 1.86 (3H, bs), 3.36 (1H, s), 3.40–3.78 (4H, m), 3.97 (4H, bs), 6.44 (1H, bs), 7.00–7.60 (6H, m), 8.30–8.50 (2H, m).

3-[(E)-3-[4-(pyridin-3-ylmethyl)phenyl]-2-methylal-lyloxy]-1-methylpropanol

IR (KBr) cm⁻¹: 3350.
NMR (CDCl₃) δ values:

| 1.21 (3H, d, J=6 Hz), 1.40–2.00 (m) 1.87 (bs) | } (5H), |
| --- | --- |

2.90 (1H, s), 3.64 (1H, t, J=6 Hz),

| 3.80–4.40 (m) 3.95 (s) 4.00 (s) | } (5H), |
| --- | --- |

6.45 (1H, bs), 6.80–7.60 (6H, m), 8.20–8.60 (2H, m).

3-[(E)-3-[4-(pyridin-3-ylmethyl)phenyl]-2-methylal-lyloxy]-2-methylpropanol

IR (KBr) cm⁻¹: 3350.
NMR (CDCl₃) δ values:

| 0.91 (3H, d, J=7 Hz) 1.70–2.40 (m) 1.88 (bs) | } (4H), |
| --- | --- |

3.07 (1H, s), 3.20–3.80 (4H, m), 3.96 (2H, s), 4.00 (2H, s), 6.45 (1H, bs), 6.88–7.62 (6H, m), 8.30–8.60 (2H, m).

3-[(E)-3-[4-(pyridin-3-ylmethyl)phenyl]-2-methylal-lyloxy]butanol

IR (film) cm⁻¹: 3350.
NMR (CDCl₃) δ values:

| 1.33–1.96 (m) 1.87 (bs) | } (7H), | 3.32–4.12 (m) 3.88 (s) 3.98 (s) | } (9H), |
| --- | --- | --- | --- |

6.44 (1H, bs), 6.80–7.76 (6H, m), 8.30–8.60 (2H, m).

3-[(E)-3-[4-(pyridin-3-ylmethyl)phenyl]allyloxy]-2,2-dimethylpropanol

IR (film) cm⁻¹: 3300.
NMR (CDCl₃) δ values: 0.96 (6H, s), 3.03 (1H, bs), 3.34 (2H, s), 3.48 (2H, s), 3.95 (2H, s), 4.12 (2H, d, J=5 Hz), 6.17 (1H, dt, J=16 Hz, 5 Hz), 6.61 (1H, d, J=16 Hz), 7.00–7.55 (6H, m), 8.38–8.55 (2H, m).

3-[(E)-3-[4-(pyridin-3-ylmethyl)phenyl]-2-methylal-lyloxy]-1,3-dimethylpropanol (colorless and oily)

IR (film) cm⁻¹: 3400–3320.
NMR (CDCl₃) δ values:

| 0.90–1.34 (6H, m), 1.34–1.96 (m) 1.88 (bs) | } (5H), |
| --- | --- |
| 2.83 (1H, bs), 3.50–4.12 (m) 3.95 (s) | } (6H), |

6.46 (1H, bs), 6.92–7.60 (6H, m), 8.30–8.60 (2H, m).

6-[(E)-3-[4-(pyridin-3-ylmethyl)phenyl]-2-methylal-lyloxy]hexanol (colorless and oily)

IR (film) cm⁻¹: 3600–3000.
NMR (CDCl₃) δ values:

| 1.10–2.02 (m) 1.86 (bs) | } (11H), 3.18 (1H, s), |
| --- | --- |

3.27–3.80 (4H, m), 3.97 (4H, bs), 6.46 (1H, bs), 6.92–7.62 (6H, m), 8.23–8.52 (2H, m).

3-[(E)-3-[4-(pyridin-3-yloxy)phenyl]-2-methylallyloxy]-2,2-dimethylpropanol (colorless and oily)

IR (film) cm⁻¹: 3380–3260.
NMR (CDCl₃) δ values: 0.96 (6H, s), 1.87 (3H, bs), 3.06 (1H, bs), 3.29 (2H, s), 3.44 (2H, s), 3.98 (2H, bs), 6.39 (1H, bs), 6.71–7.50 (6H, m), 8.17–8.50 (2H, m).

Example 5

(1) In 10 ml of methylene chloride was dissolved 500 mg of 3-[4-(pyridin-3-ylmethyl)phenyl]propanol, and 0.80 ml of thionyl chloride was added to the resulting solution with ice-cooling, after which the resulting mixture was subjected to reaction under reflux for one hour. The solvent and the excessive thionyl chloride were removed by distillation under reduced pressure, to obtain 3-[4-(pyridin-3-ylmethyl)phenyl]propyl chloride hydrochloride as the residue. This residue was dissolved in 4 ml of dimethyl sulfoxide.

(2) To 5 ml of ethylene glycol was added 1.2 g of potassium tert-butoxide in portions at room temperature with stirring. To the resulting solution was dropwise added the dimethyl sulfoxide solution obtained in (1) above at the same temperature, after which the resulting mixture was subjected to reaction at 90° C. for one hour. Subsequently, 40 ml of water was added thereto with ice-cooling, and the pH thereof was adjusted to 7 with 2N hydrochloric acid, after which the mixture was subjected to extraction with 20 ml of ethyl acetate. The extract was washed successively with 20 ml of water and 10 ml of a saturated aqueous sodium chloride solution and dried over anhydrous magnesium sulfate. The solvent was removed by distillation under reduced pressure, and the residue thus obtained was purified by a column chromatography [Wako Silica Gel C-200, eluant: benzene:ethyl acetate (3:1 by volume)] to obtain 420 mg (yield 60.0%) of colorless, oily 2-[3-[4-(pyridin-3-ylmethyl)phenyl]propyloxy]ethanol.

IR (film) cm⁻¹: 3300.
NMR (CDCl₃) δ values: 1.68–2.10 (2H, m), 2.52–2.78 (2H, m), 3.30–3.95 (9H, m), 6.87–7.55 (6H, m), 8.20–8.50 (2H, m).

In the same manner as above, the following compound was obtained:

2-[3-[4-(Imidazol-1-ylmethyl)phenyl]propyloxy]ethanol (colorless and oily)

IR (film) cm⁻¹: 3250.
NMR (CDCl₃) δ values: 1.62–2.10 (2H, m), 2.57–2.84 (2H, m), 3.36–3.91 (6H, m), 4.94 (1H, s), 5.07 (2H, s), 6.91–7.66 (7H, m).

Example 6

In 10 ml of methylene chloride was dissolved 1.0 g of 2-[4-(pyridin-3-ylmethyl)phenyl]ethanol, and 980 mg of p-toluene sulfonic acid monohydrate was added thereto with ice-cooling. To the resulting solution was added 2.7 g of ethyl diazoacetate with ice-cooling, after which 700 mg of boron trifluoridediethyl ether complex was dropped into the solution. The resulting mixture was subjected to reaction at the same temperature for one hour. Subsequently, 20 ml of water and 20 ml of methylene chloride were added to the reaction mixture, and the pH thereof was adjusted to 8 with 1N aqueous sodium hydroxide solution, after which the organic layer was separated, washed successively with 20 ml of water and 20 ml of a saturated aqueous sodium chloride solution, and then dried over anhydrous sodium sulfate. The solvent was then removed by distillation under reduced pressure. The residue thus obtained was purified by a column chromatography [Wako Silica Gel C-200, eluant: toluene:ethyl acetate (1:1 by volume)], to obtain 220 mg (yield 15.7%) of oily ethyl 2-[4-(pyridin-3-ylmethyl)phenyl]ethyloxyacetate.

IR (film) cm$^{-1}$: 1730.

NMR (CDCl$_3$) δ values: 1.48 (3H, t, j=7 Hz), 3.12 (2H, t, J=7 Hz), 3.64–4.92 (8H, m), 6.72–7.92 (6H, m), 8.44–8.79 (2H, m).

Example 7

In 6 ml of anhydrous tetrahydrofuran was dissolved 370 mg of ethyl 4-(imidazol-1-ylmethyl)phenyloxyacetate, and thereto was added 0.06 g of lithium aluminum hydride with ice-cooling, after which the resulting mixture was subjected to reaction at room temperature for one hour. Subsequently, 2.2 ml of hydrous tetrahydrofuran (water content: 10% by volume) was added thereto in small portions at the same temperature, and insolubles were removed by filtration. The solvent was removed by distillation under reduced pressure, and the residue thus obtained was dissolved in a mixed solvent of 20 ml of methylene chloride and 20 ml of water. The organic layer was separated, washed successively with 20 ml of water and 10 ml of a saturated aqueous sodium chloride solution, and then dried over anhydrous sodium sulfate. The solvent was removed by distillation under reduced pressure, and the residue thus obtained was recrystallized from a mixed solvent of ethanol and diethyl ether, to obtain 250 mg (yield 80.6%) of colorless needle crystals of 2-[4-(imidazol-1-ylmethyl)-phenyloxy]ethanol having a melting point of 81°–82° C.

IR (KBr) cm$^{-1}$: 3160.

NMR (CDCl$_3$) δ values: 3.80–4.30 (4H, m), 4.70 (1H, s), 5.10 (2H, s), 6.80–7.66 (7H, m).

In the same manner as above, the following compounds were obtained:

2-[2-[4-(Pyridin-3-ylmethyl)phenyl]ethyloxy]ethanol (colorless and oily)

IR (film) cm$^{-1}$: 3400–3240.

NMR (CDCl$_3$) δ values:

| 2.86 (2H, t, J=7 Hz), | 3.27–4.01 (m) | (9H), |
|---|---|---|
| | 3.92 (s) | |

6.50–7.71 (6H, m), 8.27–8.58 (2H, m).

2-[4-(Pyridin-3-ylmethyl)phenyloxy]ethanol (colorless crystals)

Melting point: 81°–82° C.

IR (KBr) cm$^{-1}$: 3220.

NMR (CDCl$_3$) δ values: 3.73–4.25 (7H, m), 6.70–7.62 (6H, m), 8.30–8.57 (2H, m).

Example 8

(1) In 6 ml of anhydrous tetrahydrofuran was suspended 700 mg of sodium hydride (purity: 50%), and into the suspension was dropped a mixture of 3.65 g of ethyl diethylphosphonoacetate and 3 ml of anhydrous tetrahydrofuran at a temperature of 30° to 35° C., after which the resulting mixture was subjected to reaction at room temperature for one hour. To the reaction mixture was added dropwise a mixture of 3.0 g of 4-(pyridin-3-yloxy)benzaldehyde and 3 ml of anhydrous tetrahydrofuran at room temperature, and the temperature thereof was gradually elevated. The mixture was subjected to reaction at 60° C. for 15 minutes. Subsequently, the reaction mixture was cooled to room temperature, and 20 ml of water was added to the mixture, after which the resulting mixture was subjected to extraction with 20 ml of ethyl acetate. The extract was washed with 10 ml of a saturated aqueous sodium chloride solution and dried over anhydrous magnesium sulfate, after which the solvent was removed by distillation under reduced pressure. The residue thus obtained was purified by a column chromatography [Wako Silica Gel C-200, eluant: chloroform], to obtain 3.64 g (yield 89.8%) of colorless, oily ethyl (E)-3-[4-(pyridin-3-yloxy)phenyl]acrylate.

IR (film) cm$^{-1}$: 1710.

NMR (CDCl$_3$) δ values: 1.26 (3H, t, J=7 Hz), 4.12 (2H, q, J=7 Hz), 6.18 (1H, d, J=16 Hz), 6.85 (2H, d, J=8 Hz), 7.00–7.80 (5H, m), 7.10–8.40 (2H, m).

(2) In 20 ml of ethanol was dissolved 2.0 g of ethyl (E)-3-[4-(pyridin-3-yloxy)phenyl]acrylate, and to the resulting solution was added 1.0 g of 5% palladium-carbon, after which the resulting mixture was stirred in a hydrogen atmosphere at room temperature for 5 hours. The reaction mixture was filtered and the filtrate thus obtained was concentrated under reduced pressure to obtain 2.0 g (yield 99%) of colorless, oily ethyl 3-[4-(pyridin-3-yloxy)phenyl]propionate.

IR (film) cm$^{-1}$: 1730.

NMR (CDCl$_3$) δ values: 1.24 (3H, t, J=7 Hz), 2.40–3.20 (4H, m), 4.14 (2H, q, J=7 Hz), 6.94 (2H, d, J=9 Hz), 7.10–7.40 (4H, m), 8.20–8.50 (2H, m).

(3) In the same manner as in Example 1, 1.4 g (yield 86.9%) of colorless, oily 3-[4-(pyridin-3-yloxy)phenyl]-propanol was obtained from 1.91 g of ethyl 3-[4-(pyridin-3-yloxy)phenyl]propionate.

IR (film) cm$^{-1}$: 3500–3100.

NMR (CDCl$_3$) δ values: 1.60–2.18 (2H, m), 2.58–2.80 (2H, m), 3.52–3.78 (2H, m), 3.90 (1H, s), 6.72–7.32 (6H, m), 8.12–8.36 (2H, m).

(4) From 1.40 g of 3-[4-(pyridin-3-yloxy)phenyl]-propanol, 0.66 g (yield 40%) of colorless, oily 2-[3-[4-(pyridin-3-yloxy)phenyl]propyloxy]ethanol was obtained in the same manner as in Example 4.

IR (film) cm$^{-1}$: 3550–3150.

NMR (CDCl$_3$) δ values: 1.65–2.12 (2H, m), 2.58–2.84 (2H, m), 2.92 (1H, s), 3.35–4.0 (6H, m), 6.76–7.42 (6H, m), 8.22–8.50 (2H, m).

Example 9

(1) From 5.0 g of ethyl (E)-3-(4-bromophenyl)methacrylate, 3.5 g (yield 83%) of colorless, needle crystals of (E)-3-(4-bromophenyl)-2-methylallyl alcohol having a melting point of 82° C. was obtained in the same manner as in Example 2.

IR (KBr) cm$^{-1}$: 3330, 1655.

NMR (CDCl$_3$) δ values: 1.82 (3H, bs), 2.49 (1H, s), 4.14 (2H, s), 6.41 (1H, bs), 7.06, 7.40 (4H, A$_2'$B$_2'$, J=8 Hz).

(2) From 3.2 g of (E)-3-(4-bromophenyl)-2-methylallyl alcohol, 2.13 g (yield 55.7%) of colorless, oily 2-[(E)-3-(4-bromophenyl)-2-methylallyloxy]ethanol was obtained in the same manner as in Example 4.

IR (film) cm$^{-1}$: 3400, 1660.

NMR (CDCl$_3$) δ values: 1.84 (3H, d, J=2 Hz), 2.93 (1H, s), 3.41–3.93 (4H, m), 4.03 (2H, s), 6.40 (1H, bs), 7.07, 7.43 (4H, A$_2'$B$_2'$, J=8 Hz).

(3) In 20 ml of methylene chloride were dissolved 2.13 g of 2-[(E)-3-(4-bromophenyl)-2-methylallyloxy]ethanol and 1.43 ml of 3,4-dihydro-2H-pyran and 20 mg of p-toluenesulfonic acid monohydrate was added to the resulting solution with ice-cooling, after which the resulting mixture was subjected to reaction at room temperature for 3 hours. Subsequently, 30 ml of methylene chloride and 20 ml of a saturated aqueous sodium hydrogen-carbonate solution were added to the reaction mixture, and the organic layer was separated, washed successively with 20 ml of water and 20 ml of a saturated aqueous sodium chloride solution, and then dried over anhydrous magnesium sulfate, after which the solvent was removed by distillation under reduced pressure. The residue thus obtained was purified by a column chromatography [Wako Silica Gel C-200, eluant: toluene:ethyl acetate (20:1 by volume)] to obtain 2.6 g (yield 93%) of oily tetrahydropyranyl ether of 2-[(E)-3-(4-bromophenyl)-2-methylallyloxy]ethanol.

IR (film) cm$^{-1}$: 1665, 1125, 1070, 1035.

NMR (CDCl$_3$) δ values:

| 1.21–2.11 (m) | | 3.29–4.20 (m) | |
|---|---|---|---|
| 1.88 (bs) | (9H), | 4.05 (s) | (8H), |

4.67 (1H, bs), 6.46 (1H, bs), 7.12, 7.44 (4H, A$_2'$B$_2'$, J=8 Hz).

(4) In 10 ml of anhydrous tetrahydrofuran was dissolved 910 mg of tetrahydropyranyl ether of 2-[(E)-3-(4-bromophenyl)-2-methylallyloxy]ethanol, and 1.9 ml of 1.5M n-butyl lithium hexane solution was dropped into the resulting solution at a temperature of −70° C. to −65° C., after which the resulting mixture was subjected to reaction at the same temperature for one hour. To the reaction mixture was dropwise added 1 ml of anhydrous tetrahydrofuran containing 0.27 ml of nicotinic aldehyde at a temperature of −70° C. to −65° C., and the resulting mixture was subjected to reaction at the same temperature for one hour. Subsequently, the solvent was removed by distillation under reduced pressure, and to the residue thus obtained were added 50 ml of ethyl acetate and 20 ml of a saturated aqueous ammonium chloride solution, after which the organic layer was separated, washed successively with 20 ml of water and 20 ml of a saturated aqueous sodium chloride solution and then dried over anhydrous sodium sulfate. The solvent was then removed by distillation under reduced pressure. The residue thus obtained was purified by a column chromatography [Wako Silica Gel C-200, eluant: toluene:ethyl acetate (1:3 by volume)] to obtain 230 mg (yield 23.4%) of colorless, oily tetrahydropyranyl ether of 2-[(E)-3-[4-(pyridin-3-yl-hydroxymethyl)-phenyl]-2-methylallyloxy]ethanol.

IR (film) cm$^{-1}$: 3400, 1120, 1070, 1030.

NMR (CDCl$_3$) δ values:

| 1.12–2.31 (m) | | 3.23–4.23 (m) | |
|---|---|---|---|
| 1.86 (bs) | (9H), | 4.02 (s) | (8H), |

4.61 (1H, bs), 5.22 (1H, bs), 5.73 (1H, s), 6.44 (1H, bs), 6.92–7.92 (6H, m), 8.04–8.52 (2H, m).

(5) In 5 ml of methylene chloride was dissolved 180 mg of tetrahydropyranyl ether of 2-[(E)-3-[4-(pyridin-3-yl-hydroxymethyl)phenyl]-2-methylallyloxy]ethanol, and 0.08 ml of pyridine was added to the resulting solution, after which 0.12 ml of thionyl chloride was further added thereto. The resulting mixture was subjected to reaction under reflux for 2 hours. The excessive thionyl chloride and the solvent were removed by distillation under reduced pressure, and the residue thus obtained was dissolved in a mixed solvent of 20 ml of ethyl acetate and 20 ml of water, after which the pH of the resulting solution was adjusted to 7.5 with a saturated aqueous sodium hydrogencarbonate solution. Subsequently, the organic layer was separated, washed successively with 20 ml of water and 20 ml of a saturated aqueous sodium chloride solution, and dried over anhydrous sodium sulfate, and the solvent was removed by distillation under reduced pressure, to obtain crude tetrahydropyranyl ether of 2-[(E)-3-[4-pyridin-3-ylchloromethyl)phenyl]-2-methylallyloxy]ethanol. This was dissolved in 2 ml of acetic acid, and 62 mg of zinc powder was added to the resulting solution at room temperature, after which the resulting mixture was subjected to reaction at the same temperature for one hour. Subsequently, 30 ml of ethyl acetate and 20 ml of water were added to the reaction mixture, and the pH thereof was adjusted to 7.5 with sodium hydrogencarbonate, after which the organic layer was separated. This organic layer was successively washed with 20 ml of water and 20 ml of a saturated aqueous sodium chloride solution, and dried over anhydrous sodium sulfate, after which the solvent was removed by distillation under reduced pressure to obtain crude tetrahydropyranyl ether of 2-[(E)-3-[4-(pyridin-3-ylmethyl)phenyl]-2-methylallyloxy]ethanol. This was dissolved in 5 ml of ethanol, and 180 mg of p-toluenesulfonic acid monohydrate was added to the resulting solution at room temperature, after which the resulting mixture was subjected to reaction at the same temperature for one hour. Subsequently, the solvent was removed by distillation under reduced pressure, and 20 ml of ethyl acetate and 20 ml of water were added to the residue thus obtained, after which the pH thereof was adjusted to 7.5 with sodium hydrogencarbonate. The organic layer was then separated, washed successively with 20 ml of water and 20 ml of a saturated aqueous sodium chloride solution, and then dried over anhydrous sodium sulfate, after which the solvent was removed by distillation under reduced pressure. The residue thus obtained was purified by a column chromatography [Wako Silica Gel C-200, eluant: toluene:ethyl acetate (1:1 by volume)] to obtain 50 mg (yield 37.6%) of colorless, oily 2-[(E)-3-[4-(pyridin-3-ylmethyl)phenyl]-2-methylallyloxy]ethanol.

The physical properties of this product was identical with those obtained in Example 4.

In the same manner as above, the following compounds were obtained:

2-[(E)-3-[4-(pyridin-3-ylmethyl)phenyl]allyloxy]ethanol
2-[3-[4-(Pyridin-3-ylmethyl)phenyl]propyloxy]ethanol The physical properties of these compounds were identical with those obtained in Examples 4 and 5.

Example 10

(1) In 5 ml of methylene chloride was dissolved 300 mg of (E)-3-[4-(pyridin-3-ylmethyl)phenyl]allyl alcohol, and 0.58 ml of thionyl chloride was dropped into the resulting solution with ice-cooling, after which the resulting mixture was subjected to reaction under reflux for 30 minutes. The solvent and the excessive thionyl chloride were removed by distillation under reduced pressure, to obtain (E)-3-[4-(pyridin-3-ylmethyl)phenyl]allyl chloride hydrochloride as the residue. This was dissolved in 3 ml of N,N-dimethylformamide.

(2) In 3 ml of ethanol was dissolved 310 mg of potassium hydroxide, and 0.37 ml of mercaptoethanol was added to the resulting solution. To this solution was dropwise added the N,N-dimethylformamide solution obtained in (1) above with ice-cooling, and the resulting mixture was subjected to reaction at room temperature for 30 minutes. Subsequently, 30 ml of ethyl acetate and 20 ml of water were added to the reaction mixture, and the organic layer was separated, washed with three 20-ml portions of water, thereafter washed with 20 ml of a saturated aqueous sodium chloride solution, and then dried over anhydrous magnesium sulfate. The solvent was removed by distillation under reduced pressure to obtain 340 mg (yield 89.5%) of colorless crystals of (E)-2-[3-[4-(pyridin-3-ylmethyl)phenyl]allylthio]ethanol having a melting point of 73°–74° C.

IR (KBr) cm$^{-1}$: 3290–3230.

NMR (CDCl$_3$) δ values: 2.68 (2H, t, J=6 Hz), 3.25 (1H, s), 3.29 (2H, d, J=6 Hz), 3.73 (2H, t, J=6 Hz), 3.92 (2H, s), 6.07 (1H, dt, J=16 Hz, 6 Hz), 6.44 (1H, d, J=16 Hz), 6.84–7.57 (6H, m), 8.23–8.55 (2H, m).

EXAMPLE 11

(1) In 9.25 ml of methylene chloride was dissolved 1.85 g of (E)-3-[4-(pyridin-3-ylmethyl)phenyl]-2-methylallyl alcohol, and 2.80 ml of thionyl chloride was dropped into the resulting solution with ice-cooling, after which the resulting mixture was subjected to reaction under reflux for 30 minutes. The solvent and the excessive thionyl chloride were removed by distillation under reduced pressure to obtain oily (E)-3-[4-(pyridin-3-ylmethyl)phenyl]-2-methylallyl chloride hydrochloride.

Melting point: 118°–120° C. (recrystallization solvent: isopropyl alcohol-ethyl acetate).

IR (KBr) cm$^{-1}$: $\nu_{NH}$ 2550, $\nu_{C=C}$ 1600.

NMR (CDCl$_3$) δ values: 1.98 (3H, d, J=1.5 Hz), 4.18 (2H, s), 4.28 (2H, s), 6.54 (1H, s), 7.22 (4H, bs), 7.84–9.00 (4H, m), 16.55 (1H, bs).

Subsequently, this was dissolved in 9.25 ml of methylene chloride.

(2) The methylene chloride solution obtained in (1) above was dropped into a mixture of 1.86 ml of 2-methylaminoethanol and 9.25 ml of methylene chloride with ice-cooling, and the resulting mixture was subjected to reaction at room temperature overnight. Subsequently, the reaction mixture was washed with three 10-ml portions of water, and 18 ml of water was added to the mixture, after which the pH thereof was adjusted to 1.5 with 2N hydrochloric acid. The aqueous layer was separated and washed with four 9 ml-portions of chloroform, and then 18 ml of ethyl acetate was added to the aqueous layer, after which the pH thereof was adjusted to 8.0 with sodium hydrogencarbonate. The organic layer was separated, washed with 9 ml of water, and then dried over anhydrous magnesium sulfate. The solvent was removed by distillation under reduced pressure, and the residue thus obtained was purified by a column chromatography [Wako Silica Gel C-200, eluant: chloroform:ethanol (20:1 by volume)] to obtain 1.36 g (yield 59.4%) of colorless, oily 2-[N-methyl-N-[(E)-3-[4-(pyridin-3-ylmethyl)phenyl]-2-methylallyl]amino]ethanol.

IR (film) cm$^{-1}$: $\nu_{OH}$ 3400.

NMR (CDCl$_3$) δ values: 1.90 (3H, bs), 2.24 (3H, s), 2.54 (2H, t,

| J=6 Hz), 3.04 (2H, s), | 3.64 (t, J=6 Hz) | (5H), |
|---|---|---|
| | 3.75 (s), 3.89 (s) | |

6.35 (1H, bs), 6.70–7.60 (6H, m), 8.10–8.50 (2H, m).

EXAMPLE 12

(1) In 10 ml of methylene chloride was dissolved 2.04 g of 3-[4-(pyridin-3-ylmethyl)phenyl]propanol, and 3.26 ml of thionyl chloride was added dropwise to the resulting solution with ice-cooling, after which the resulting mixture was subjected to reaction under reflux for one hour. The solvent and the excessive thionyl chloride were removed by distillation under reduced pressure to obtain oily 3-[4-(pyridin-3-ylmethyl)phenyl]propyl chloride hydrochloride.

(2) To the hydrochloride obtained in (1) above was added 7 ml of 2-methylaminoethanol, and the resulting mixture was subjected to reaction at 100° C. for 30 minutes. The excessive 2-methylaminoethanol was removed by distillation under reduced pressure, and 30 ml of methylene chloride and 20 ml of water were added to the residue thus obtained, after which the resulting mixture was stirred at room temperature for 30 minutes. The organic layer was thereafter separated, washed successively with 20 ml of water and 10 ml of a saturated aqueous sodium chloride solution, and then dried over anhydrous magnesium sulfate. The solvent was removed by distillation under reduced pressure to obtain 2.44 g (yield 95.7%) of colorless, oily 2-[N-methyl-N-[3-[4-(pyridin-3-ylmethyl)phenyl]propyl]amino]ethanol.

IR (film) cm$^{-1}$: $\nu_{OH}$ 3350.

NMR (CDCl$_3$) δ values:

| 1.56–2.81 (m) | (11H), |
|---|---|
| 2.23 (s) | |

3.28 (1H, s), 3.56 (2H, t, J=6 Hz), 3.91 (2H, s), 6.82–7.59 (6H, m), 8.29–8.59 (2H, m).

Example 13

(1) In 11 ml of methylene chloride was dissolved 2.11 g of (E)-3-[4-(imidazol-1-ylmethyl)phenyl]allyl alcohol, and 3.57 ml of thionyl chloride was dropped into the resulting solution with ice-cooling, after which the resulting mixture was subjected to reaction under reflux for one hour. The solvent and the excessive thionyl chloride were removed by distillation under reduced pressure to obtain oily (E)-3-[4-(imidazol-1-ylmethyl)phenyl]allyl chloride hydrochloride. This was dissolved in 8 ml of methylene chloride.

(2) The methylene chloride solution obtained in (1) above was dropped into a mixture of 3.94 ml of 2-methylaminoethanol and 6 ml of methylene chloride with ice-cooling, and the resulting mixture was subjected to reaction overnight at room temperature. The reaction mixture was washed successively with two 20-ml portions of water and 10 ml of a saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: chloroform:ethanol (20:1–10:1 by volume)] to obtain 1.7 g (yield 63.7%) of colorless, oily 2-[N-methyl-N-[(E)-3-[4-(imidazol-1-ylmethyl)phenyl]allyl]amino]ethanol.

IR (film) cm$^{-1}$: $\nu_{OH}$ 3200.

NMR (d$_6$-DMSO) δ values: 2.23 (3H, s), 2.48 (2H, t, J=6 Hz), 3.14 (2H, d, J=6 Hz), 3.54 (2H, t, J=6 Hz), 4.15 (1H, s), 5.16 (2H, s), 6.21 (1H, dt, J=16 Hz, 6 Hz), 6.56 (1H, d, J=16 Hz), 6.84–7.81 (7H, m).

In the same manner as above, the following compounds were obtained:

2-[N-methyl-N-[(E)-3-[4-(pyridin-3-ylmethyl)phenyl]allyl]amino]ethanol (colorless and oily)

NMR (CDCl$_3$) δ values: 2.30 (3H, s), 2.58 (2H, t, J=6 Hz), 3.20 (2H, d, J=6 Hz), 3.68 (2H, t, J=6 Hz), 3.92 (3H, s), 6.18 (1H, dt, J=16 Hz, 6 Hz), 6.52 (1H, d, J=16 Hz), 6.80–7.60 (6H, m), 8.28–8.68 (2H, m).

2-[N-benzyl-N-[(E)-3-[4-(pyridin-3-ylmethyl)phenyl]-2-methylallyl]amino]ethanol (colorless and oily)

NMR (CDCl$_3$) δ values: 1.86 (3H, bs), 2.60 (2H, t, J=5 Hz), 2.92 (1H, s),

| 3.12 (2H, s), | 3.36–3.82 (m) | (4H), |
|---|---|---|
| | 3.60 (s) | |

3.90 (2H, s), 6.38 (1H, bs), 6.85–7.55 (11H, m), 8.25–8.60 (2H, m).

EXAMPLE 14

In 5 ml of benzene was dissolved 500 mg of (E)-3-[4-(pyridin-3-ylmethyl)phenyl]-2-methylallyl alcohol, and 1.4 g of nickel peroxide was added to the resulting solution, after which the resulting mixture was subjected to reaction at 50° C. for 12 hours. Subsequently, insolubles were removed by filtration and then washed with 10 ml of benzene. The washings were combined with the filtrate, and the solvent was removed by distillation under reduced pressure, after which the residue thus obtained was purified by a column chromatography [Wako Silica Gel C-200, eluant: benzene:ethyl acetate (5:1 by volume)] to obtain 480 mg (yield 96.0%) of pale yellow, oily (E)-3-[4-(pyridin-3-ylmethyl)phenyl]-2-methylacrylic aldehyde.

IR (film) cm$^{-1}$: $\nu_{C=O}$ 1665.

NMR (CDCl$_3$) δ values: 2.01 (3H, d, J=2 Hz), 3.96 (2H, s), 6.86–7.56 (7H, m), 8.20–8.50 (2H, m), 9.45 (1H, s).

EXAMPLE 15

In 25 ml of methylene chloride was suspended 13.3 g of anhydrous aluminum chloride, and 7.3 g of 3-chloro-2-methylpropionyl chloride was added to the suspension with ice-cooling, after which 8.2 g of 3-benzylpyridine hydrochloride was added in small portions to the suspension. The resulting mixture was subjected to reaction with ice-cooling for 2 hours and then at room temperature for one hour. The reaction mixture was added in small portions to a mixture of 246 ml of iced water and 49 ml of methylene chloride, and the organic layer was separated, while the aqueous layer was extracted with 40 ml of methylene chloride. The organic layers were combined and then 80 ml of water was added thereto after which the resulting mixture was neutralized with sodium hydrogencarbonate. The organic layer was separated, washed with 50 ml of water, and thereafter dried over anhydrous magnesium sulfate. The solvent was removed by distillation under reduced pressure, and the residue thus obtained was purified by a column chromatography [Wako Silica Gel C-200, eluant: chloroform:ethyl acetate (1:1 by volume)] to obtain 10.53 g (yield 96.0%) of colorless, oily 3-[p-(3-chloro-2-methylpropionyl)benzyl]pyridine.

IR (film) cm$^{-1}$: $\nu_{C=O}$ 1675.

NMR (CDCl$_3$) δ values:

| 1.25 (3H, d, J=6 Hz), | 3.38–4.10 (m) | (5H), |
|---|---|---|
| | 4.00 (s) | |

7.00–7.60 (4H, m), 7.85 (2H, d, J=8 Hz), 8.36–8.70 (2H, m).

Example 16

In 50 ml of ethylene glycol was dissolved 5.0 g of potassium tert-butoxide, and a mixed solution of 6 ml of N,N-dimethylformamide and 5.0 g of 3-[p-(3-chloro-2-methylpropionyl)benzyl]pyridine was added in small portions to the above solution with ice-cooling, after which the resulting mixture was subjected to reaction at the same temperature for 2 hours, and then neutralized with 9 ml of 2N hydrochloric acid and diluted with 50 ml of water. The resulting mixture was extracted with two 50-ml portions of methylene chloride. The extracts were combined, washed with water, and then dried over anhydrous magnesium sulfate. The solvent was removed by distillation under reduced pressure, and the residue thus obtained was purified by a column chromatography [Wako Silica Gel C-200, eluant: chloroform:ethyl acetate (1:3 by volume)] to obtain 5.63 g (yield 85.8%) of colorless, oily 3-[p-[3-(2-hydroxyethyl)oxy-2-methylpropionyl]benzyl]pyridine.

IR (film) cm$^{-1}$: $\nu_{C=O}$ 1675.

NMR (CDCl$_3$) δ values:

| 1.15 (3H, d, J=6 Hz), | 3.24–4.12 (m) | (10H), |
|---|---|---|
| | 4.00 (s) | |

7.00–7.56 (4H, m), 7.82 (2H, d, J=8 Hz), 8.20–8.50 (2H, m).

Example 17

(1) In 3 ml of pyridine was dissolved 2.0 g of 3-[p-[3-(2-hydroxyethyl)oxy-2-methylpropionyl]benzyl]pyridine, and 0.76 ml of acetic anhydride was added to the resulting solution with ice-cooling, after which the resulting mixture was subjected to reaction at room temperature for 12 hours. The solvent was removed by distillation under reduced pressure, and the residue thus obtained was dissolved in 16 ml of ethyl acetate. The resulting solution was washed with 5 ml of water, and then dried over anhydrous magnesium sulfate. The solvent was removed by distillation under reduced pressure to obtain crude oily 3-[p-[3-(2-acetoxyethyl)oxy-2-methylpropionyl]benzyl]pyridine. This was dissolved in 17 ml of ethanol.

(2) To the ethanol solution obtained in (1) above was added 0.25 g of sodium boron hydride in small portions with ice-cooling, and the resulting mixture was subjected to reaction at the same temperature for one hour. To the reaction mixture was added 0.38 ml of acetic acid, and the solvent was thereafter removed by distillation under reduced pressure, after which 20 ml of a saturated aqueous sodium chloride solution was added to the residue thus obtained. The resulting mixture was extracted with 20 ml of ethyl acetate, and the organic layer was washed with water and then dried over anhydrous magnesium sulfate. The solvent was removed by distillation under reduced pressure, and the residue thus obtained was purified by a column chromatography [Wako Silica Gel C-200, eluant: chloroform:ethyl acetate (1:1 by volume)] to obtain 2.07 g (yield 90.4%) of colorless, oily 3-[p-[3-(2-acetoxyethyl)oxy-1-hydroxy-2-methylpropyl]benzyl]pyridine.

IR (film) cm$^{-1}$: $\nu_{OH}$ 3400, $\nu_{C=O}$ 1740.

NMR (CDCl$_3$) δ values:

| 0.75 (d, J=6 Hz)<br>0.85 (d, J=6 Hz) } (3H), | 1.80–2.35 (m)<br>2.05 (s) } (4H), |
|---|---|

3.34–3.74 (4H, m), 3.92 (3H, s), 4.10–4.32 (2H, m),

| 4.50 (d, J=8 Hz)<br>4.80 (d, J=4 Hz) } (1H), |
|---|

6.95–7.58 (6H, m), 8.20–8.50 (2H, m).

Example 18

In 22.5 ml of ethanol was dissolved 4.51 g of 3-[p-[3-(2-hydroxyethyl)oxy-2-methylpropionyl]benzyl]pyridine, and 286 mg of sodium boron hydride was added in small portions to the resulting solution with ice-cooling, after which the resulting mixture was subjected to reaction at the same temperature for one hour. The solvent was removed by distillation under reduced pressure, and 22.5 ml of water and 22.5 ml of ethyl acetate were added to the residue thus obtained, after which the pH thereof was adjusted to 7.0 with 2N hydrochloric acid. The organic layer was separated, washed with 10 ml of water, and 22.5 ml of water was added to the organic layer, after which the pH thereof was adjusted to 1.5 with 2N hydrochloric acid. The aqueous layer was separated, and then washed with 10 ml of ethyl acetate, after which 22.5 ml of ethyl acetate was added to the aqueous layer. The resulting mixture was neutralized with sodium hydrogencarbonate. The organic layer was separated, washed with 10 ml of water, and then dried over anhydrous magnesium sulfate. The solvent was removed by distillation under reduced pressure to obtain 4.2 g (yield 92.5%) of colorless, oily 3-[p-[1-hydroxy-3-(2-hydroxyethyl)oxy-2-methylpropyl]benzyl]pyridine.

IR (film) cm$^{-1}$: $\nu_{OH}$ 3300.

NMR (CDCl$_3$) δ values:

| 0.70 (d, J=6 Hz)<br>0.80 (d, J=6 Hz) } (3H), | |
|---|---|
| 1.80–2.35 (1H, m), 3.10–4.10 (m)<br>3.94 (s) } (10H), | |
| 4.52 (d, J=8 Hz)<br>4.82 (d, J=4 Hz) } (1H), | |

6.85–7.60 (6H, m), 8.10–8.60 (2H, m).

Example 19

(1) In 15 ml of methylene chloride was suspended 8.1 g of anhydrous aluminum chloride, and 3.0 ml of 3-chloropropionyl chloride was added to the suspension with ice-cooling, after which 5.0 g of 3-benzylpyridine hydrochloride was added in small portions to the resulting mixture over 30 minutes. The resulting mixture was subjected to reaction at room temperature for one hour, and then the reaction mixture was added to 30 ml of iced water. The crystals thus precipitated were collected by filtration, and suspended in a mixture of 50 ml of ethyl acetate and 30 ml of water, after which the resulting suspension was neutralized with sodium hydrogencarbonate with ice-cooling. Insolubles were removed by filtration, and the organic layer of the filtrate was separated, washed with 10 ml of a saturated aqueous sodium chloride solution, and then dried over anhydrous magnesium sulfate, after which the solvent was removed by distillation under reduced pressure to obtain 5.5 g (yield 86.6%) of pale yellow, oily 3-[p-(3-chloropropionyl)benzyl]pyridine.

IR (film) cm$^{-1}$: $\nu_{C=O}$ 1675.

(2) In a mixture of 3.5 ml of N,N-dimethylformamide and 3.5 ml of ethylene glycol was dissolved 700 mg of the 3-[p-(3-chloropropionyl)benzyl]pyridine obtained in (1) above, and into the resulting solution was dropped a solution of 130 mg of sodium hydride (purity 60%) in 3.5 ml of ethylene glycol with ice-cooling, after which the resulting mixture was subjected to reaction at the same temperature for 20 minutes. Subsequently, the reaction mixture was diluted with 20 ml of water, and the pH thereof was adjusted to 7.0 with 2N hydrochloric acid, after which the mixture was extracted with four 20-ml portions of ethyl acetate. The extracts were combined, washed with 20 ml of water and then dried over anhydrous magnesium sulfate. The solvent was removed by distillation under reduced pressure, and the residue thus obtained was purified by a column chromatography [Wako Silica Gel C-200, eluant: benzene:ethyl acetate (1:1 by volume)] to obtain 630 mg (yield 82.9%) of colorless, oily 3-[p-[3-(2-hydroxyethyl)oxypropionyl]benzyl]pyridine.

IR (film) cm$^{-1}$: $\nu_{OH}$ 3400, $\nu_{C=O}$ 1675.

NMR (CDCl$_3$) δ values:

| 3.03–3.33 (2H, m), 3.40–4.08 (m)<br>3.98 (s) } (9H), |
|---|
| 6.98–8.00 (m)<br>7.18, 7.82 (A$_2$'B$_2$', J=8 Hz) } (6H), |

8.20–8.50 (2H, m).

Example 20

In 30 ml of methylene chloride were dissolved 3.0 g of 3-[p-[3-(2-hydroxyethyl)oxypropionyl]benzyl]pyridine and 1.61 ml of triethylamine, and into the resulting solution was dropped 0.90 ml of acetyl chloride over 30 minutes with ice-cooling. The resulting mixture was subjected to reaction at room temperature for 2 hours, after which 20 ml of water was added to the reaction mixture. The pH of the mixture was adjusted to 7 with sodium hydrogencarbonate, and the organic layer was separated, washed with 10 ml of water, and then dried over anhydrous magnesium sulfate. The solvent was removed by distillation under reduced pressure, and the residue thus obtained was purified by a column chromatography [Wako Silica Gel C-200, eluant: benzene:ethyl acetate (1:1 by volume)] to obtain 2.94 g (yield 85.7%) of pale yellow, oily 3-[p-[3-(2-acetoxyethyl)oxypropionyl]benzyl]pyridine.

IR (film) cm$^{-1}$: $\nu_{C=O}$ 1735, 1675.

NMR (CDCl$_3$) δ values: 2.00 (3H, s), 3.20 (2H, t, J=6 Hz), 3.40–4.30 (8H, m),

| 6.85–8.08 (m) | (6H), |
| 7.22, 7.86 (A$_2$'B$_2$', J=8 Hz) | |

8.20–8.60 (2H, m).

Example 21

In 27 ml of ethanol was dissolved 2.70 g of 3-[p-[3-(2-acetoxyethyl)oxypropionyl]benzyl]pyridine, and to the resulting solution was added 0.34 g of sodium boron hydride in portions with ice-cooling over 30 minutes, after which the resulting mixture was subjected to reaction at the same temperature for one hour. To the reaction mixture were added 30 ml of iced water and 20 ml of ethyl acetate, and then, the pH thereof was adjusted to 2.0 with 2N hydrochloric acid. The aqueous layer was separated, and 30 ml of ethyl acetate was added thereto, after which the pH thereof was adjusted to 7 with sodium hydrogencarbonate. The organic layer was separated, washed with 10 ml of water, and then dried over anhydrous magnesium sulfate. The solvent was removed by distillation to obtain 2.25 g (yield 82.7%) of colorless, oily 3-[p-[3-(2-acetoxyethyl)oxy-1-hydroxypropyl]benzyl]pyridine.

IR (film) cm$^{-1}$: $\nu_{OH}$ 3400, $\nu_{C=O}$ 1735.

NMR (CDCl$_3$) δ values:

| 2.00 (3H, s), 3.20–4.50 (m) | (11H), |
| 3.88 (s) | |

4.80 (1H, t, J=6 Hz), 6.75–7.56 (6H, m), 8.00–8.40 (2H, m).

Example 22

In the same manner as in Example 19 (2), 3-[p-(3-chloropropionyl)benzyl]pyridine was reacted with 2-tert-butoxyethanol to obtain colorless, oily 3-[p-[3-(2-tert-butoxyethyl)oxypropionyl]benzyl]pyridine in a yield of 80.9%.

IR (film) cm$^{-1}$: $\nu_{C=O}$ 1670.

NMR (CDCl$_3$) δ values: 1.19 (9H, s), 3.01–4.10 (10H, m), 7.01–7.99 (6H, m), 8.25–8.57 (2H, m).

Example 23

In the same manner as in Example 21, 3-[p-[3-(2-tert-butoxyethyl)oxypropionyl]benzyl]pyridine was reacted with sodium boron hydride to obtain colorless, oily 3-[p-[3-(2-tert-butoxyethyl)oxy-1-hydroxypropyl]benzyl]pyridine in a yield of 99.6%.

IR (film) cm$^{-1}$: $\nu_{OH}$ 3400.

NMR (CDCl$_3$) δ values: 1.20 (9H, s), 1.94 (2H, q, J=7 Hz), 3.39–3.70 (7H, m), 3.88 (2H, s), 4.82 (1H, t, J=7 Hz), 6.90–7.46 (6H, m), 8.18–8.41 (2H, m).

Example 24

In 17 ml of ethanol was dissolved 2.28 g of 3-[p-(3-chloro-2-methylpropionyl)benzyl]pyridine, and to the resulting solution was added 0.3 g of sodium boron hydride in small portions with ice-cooling, after which the resulting mixture was subjected to reaction at the same temperature for one hour. To the reaction mixture were added successively 0.54 ml of acetic acid and 30 ml of a saturated aqueous sodium chloride solution, and the resulting mixture was extracted with two 20-ml portions of ethyl acetate. The extracts were combined, washed with water, and then dried over anhydrous magnesium sulfate. The solvent was removed by distillation under reduced pressure, and the residue thus obtained was purified by a column chromatography [Wako Silica Gel C-200, eluant: chloroform:ethyl acetate (1:1 by volume)] to obtain 2.29 g (yield 99.0%) of colorless, oily 3-[p-(3-chloro-1-hydroxy-2-methylpropyl)benzyl]pyridine.

IR (film) cm$^{-1}$: $\nu_{OH}$ 3300.

NMR (CDCl$_3$) δ values:

| 0.80 (d, J=6 Hz) | (3H), 1.80–2.32 (1H, m), | |
| 0.98 (d, J=6 Hz) | | |
| 3.02–4.00 (m) | (5H), 4.50 (d, J=8 Hz) | (1H), |
| 3.88 (s) | 4.78 (d, J=4 Hz) | |

6.85–7.52 (6H, m), 8.10–8.42 (2H, m).

Example 25

In 11 ml of N,N-dimethylformamide was dissolved 2.29 g of 3-[p-(3-chloro-1-hydroxy-2-methylpropyl)benzyl]pyridine, and to the resulting solution was added 1.36 g of sodium acetate, after which the resulting mixture was subjected to reaction under reflux for 2 hours. The solvent was removed by distillation under reduced pressure, and to the residue thus obtained were added 20 ml of a saturated aqueous sodium chloride solution and 20 ml of ethyl acetate. The organic layer was separated, washed with 10 ml of water, and then dried over anhydrous magnesium sulfate. The solvent was removed by distillation under reduced pressure, and the residue thus obtained was purified by a column chromatography [Wako Silica Gel C-200, eluant: chloroform] to obtain 910 mg (yield 36.7%) of colorless, oily 3-[p-(3-acetoxy-1-hydroxy-2-methylpropyl)benzyl]pyridine.

IR (film) cm$^{-1}$: $\nu_{C=O}$ 1730.

NMR (CDCl$_3$) δ values:

| 0.78 (d, J=6 Hz) | (3H), | 1.80–2.48 (m) | (4H), |
| 0.90 (d, J=6 Hz) | | 1.98 (s) | |
| 3.40–4.80 (m) | | | |
| 4.45 (d, J=8 Hz) | (6H), 6.85–7.55 (6H, m), | | |
| 4.65 (d, J=4 Hz) | | | |

Example 26

In 8 ml of 2-propanol was dissolved 2.0 g of 2-[(E)-3-[4-(pyridin-3-ylmethyl)phenyl]-2-methylallyloxy]ethyl acetoacetate, and ammonia gas was introduced into the resulting solution for 2 hours with ice-cooling. And, the solution was subjected to reaction at room temperature for 15 hours. Subsequently, the solvent was removed by distillation under reduced pressure, and to the residue thus obtained were added 2 ml of 2-propanol and 8 ml of n-hexane, after which the resulting mixture was stirred. The crystals thus precipitated were collected by filtration to obtain 1.6 g (yield 80.2%) of 2-[(E)-3-[4-(pyridin-3-ylmethyl)phenyl]-2-methylallyloxy]ethyl 3-aminocrotonate.

Melting point: 67°-70° C.

IR (KBr) cm$^{-1}$: 3400, 3150, 1660, 1620, 1550.

NMR (CDCl$_3$) δ values:

1.88 (6H, s), 3.62 (2H, t, J=5 Hz), 3.93 (2H, s), 4.03 (2H, s), 4.22 (2H, t, J=5 Hz), 4.53 (1H, s), 6.44 (1H, s), 6.98-7.50 (6H, m), 8.35-8.46 (2H, m).

Example 27

(1) In 50 ml of tetrahydrofuran was dissolved 5.4 g of 2-[(E)-3-[4-(pyridin-3-ylmethyl)phenyl]allyloxy]ethanol, and one drop of triethylamine was added to the resulting solution. To this solution was dropwise added a mixture of 1.8 g of diketene and 4 ml of tetrahydrofuran under reflux over one hour, and then the resulting mixture was subjected to reaction at the same temperature for a further 30 minutes. Subsequently, the solvent was removed by distillation under reduced pressure, and the residue thus obtained was purified by a column chromatography [Wako Silica Gel C-200, eluant: benzene:ethyl acetate (2:1 by volume)] to obtain 5.1 g (yield 72.2%) of oily 2-[(E)-3-[4-(pyridin-3-ylmethyl)phenyl]allyloxy]ethyl acetoacetate.

IR (film) cm$^{-1}$: 1740, 1715.

NMR (CDCl$_3$) δ values: 2.22 (3H, s), 3.50 (2H, s), 3.58-3.83 (2H, m), 3.95 (2H, s), 4.06-4.45 (4H, m), 6.25 (1H, dt, J=16 Hz, 5 Hz), 6.57 (1H, d, J=16 Hz), 6.98-7.65 (6H, m), 8.30-8.63 (2H, m).

In the same manner as above, the following compounds were obtained:

2-[(E)-3-[4-(pyridin-3-ylmethyl)phenyl]-2-methylallyloxy]ethyl acetoacetate (colorless and oily)

IR (film) cm$^{-1}$: 1740, 1715.

NMR (CDCl$_3$) δ values: 1.95 (3H, s), 2.31 (3H, s), 3.57 (2H, s), 3.63-3.89 (2H, m), 4.04 (2H, s), 4.13 (2H, s), 4.24-4.54 (2H, m), 6.54 (1H, bs), 6.76-7.56 (6H, m), 8.23-8.58 (2H, m).

2-[4-(Imidazol-1-ylmethyl)phenyloxy]ethyl acetoacetate (colorless and oily)

IR (film) cm$^{-1}$: 1745, 1715.

NMR (CDCl$_3$) δ values: 2.27 (3H, s), 3.55 (2H, s), 4.12-4.70 (4H, m), 5.10 (2H, s), 6.85-7.40 (6H, m), 7.65 (1H, bs).

2-[(E)-3-[4-(imidazol-1-ylmethyl)phenyl]allyloxy]ethyl acetoacetate (colorless and oily)

IR (film) cm$^{-1}$: 1735, 1715.

NMR (CDCl$_3$) δ values: 2.30 (3H, s), 3.53 (2H, s), 3.63-3.93 (2H, m), 4.10-4.53 (4H, m), 5.10 (2H, s), 6.28 (1H, dt, J=16 Hz, 5 Hz), 6.60 (1H, d, J=16 Hz), 6.82-7.63 (7H, m).

2-[4-(Pyridin-3-ylmethyl)phenyloxy]ethyl acetoacetate (colorless and oily)

IR (film) cm$^{-1}$: 1745, 1720, 1705.

NMR (CDCl$_3$) δ values: 2.23 (3H, s), 3.45 (2H, s), 3.85 (2H, s), 4.00-4.25 (2H, m), 4.27-4.56 (2H, m), 6.60-7.52 (6H, m), 8.20-8.50 (2H, m).

3-[(E)-3-[4-(pyridin-3-ylmethyl)phenyl]-2-methylallyloxy]-2,2-dimethylpropyl acetoacetate (oily)

IR (film) cm$^{-1}$: 1730, 1710.

NMR (CDCl$_3$) δ values: 0.98 (6H, s), 1.96 (3H, bs), 2.22 (3H, s), 3.19 (2H, s), 3.54 (2H, s), 3.96 (s) / 3.98 (s) } (6H), 4.01 (s)

6.42 (1H, bs), 7.00-7.58 (6H, m), 8.35-8.62 (2H, m).

5-[(E)-3-[4-(pyridin-3-ylmethyl)phenyl]-2-methylallyloxy]pentyl acetoacetate (yellow and oily)

IR (film) cm$^{-1}$: 1730, 1710.

NMR (CDCl$_3$) δ values: 1.40-1.70 (6H, m), 1.85 (1H, bs), 2.24 (3H, s), 3.41 (2H, s), 3.42 (2H, t, J=6 Hz), 3.96 (4H, bs), 4.15 (2H, t, J=6 Hz), 6.40 (1H, bs), 7.05-7.50 (6H, m), 8.32-8.55 (2H, m).

4-[(E)-3-[4-(pyridin-3-ylmethyl)phenyl]-2-methylallyloxy]butyl acetoacetate (oily)

IR (film) cm$^{-1}$: 1735, 1715.

NMR (CDCl$_3$) δ values:

1.40-2.00 (m) / 1.86 (bs) } (7H), 2.25 (3H, s), 3.43 (2H, s), 3.47 (2H, t, J=6 Hz), 3.97 (4H, bs), 4.19 (2H, t, J=6 Hz), 6.46 (1H, bs), 6.96-7.60 (6H, m), 8.36-8.56 (2H, m).

3-[(E)-3-[4-(pyridin-3-ylmethyl)phenyl]-2-methylallyloxy]-1-methylpropyl acetoacetate IR (KBr) cm$^{-1}$: 1730, 1720.

NMR (CDCl$_3$) δ values:

1.29 (3H, d, J=6 Hz), 1.60-2.10 (m) / 1.87 (bs) } (5H), 2.22 (3H, s), 3.20-3.70 (m) / 3.40 (s) } (4H), 3.96 (4H, bs), 4.80-5.34 (1H, m), 6.46 (1H, bs), 6.92-7.70 (6H, m), 8.28-8.60 (2H, m).

3-[(E)-3-[4-(pyridin-3-ylmethyl)phenyl]-2-methylallyloxy]-2-methylpropyl acetoacetate IR (KBr) cm$^{-1}$: 1745, 1720.

NMR (CDCl$_3$) δ values: 0.99 (3H, d, J=7 Hz), 1.87 (3H, bs), 2.00-2.40 (m) / 2.24 (s) } (4H), 3.20-3.60 (m) / 3.43 (s) } (4H), 3.80-4.30 (m) / 3.97 (bs) } (6H), 6.45 (1H, bs), 6.90-7.60 (6H, m), 8.20-8.60 (2H, m).

3-[(E)-3-[4-(pyridin-3-ylmethyl)phenyl]-2-methylallyloxy]-1,3-dimethylpropyl acetoacetate (oily)

IR (film) cm$^{-1}$: 1730, 1715.

NMR (CDCl$_3$) δ values:

1.00-1.48 (6H, m), 1.50-1.98 (m) / 1.87 (bs) } (5H), 2.21 (3H, s), 3.24-3.80 (m) / 3.38 (s) } (3H), 3.97 (4H, bs), 4.80-5.40 (1H, m), 6.47 (1H, bs), 6.94-7.64 (6H, m), 8.24-8.64 (2H, m).

3-[(E)-3-[4-(pyridin-3-ylmethyl)phenyl]allyloxy]-2,2-dimethylpropyl acetoacetate (oily)

IR (film) cm$^{-1}$: 1735, 1715.

NMR (CDCl$_3$) δ values: 0.95 (6H, s), 2.25 (3H, s), 3.22 (2H, s), 3.44 (2H, s), 3.94–4.15 (6H, m), 6.17 (1H, dt, J=16 Hz, 5 Hz), 6.59 (1H, d, J=16 Hz), 7.00–7.58 (6H, m), 8.38–8.56 (2H, m).

6-[(E)-3-[4-(pyridin-3-ylmethyl)phenyl]-2-methylallyloxy]hexyl acetoacetate (yellow and oily)
IR (film) cm$^{-1}$: 1730, 1710.
NMR (CDCl$_3$) δ values:

| 1.10–2.02 (m) 1.85 (bs) | } (11H), 2.25 (3H, s), | |
|---|---|---|
| 3.30–3.70 (4H, m), | 3.90–4.40 (m) 3.97 (bs) | } (6H), |

6.44 (1H, bs), 6.80–7.60 (6H, m), 8.30–8.60 (2H, m).

3-[(E)-3-[4-(pyridin-3-yloxy)phenyl]-2-methylallyloxy]-2,2-dimethylpropyl acetoacetate (colorless and oily)
IR (film) cm$^{-1}$: 1735, 1710.
NMR (CDCl$_3$) δ values: 0.98 (6H, s), 1.85 (3H, bs), 2.24 (3H, s),

| 3.19 (2H, s), 3.43 (2H, s), | 3.97 (s) 4.00 (s) | } (4H), |
|---|---|---|

6.39 (1H, bs), 6.75–7.50 (6H, m), 8.20–8.50 (2H, m).

(2) In 10 ml of ethanol were dissolved 320 mg of 2-[(E)-3-[4-(pyridin-3-ylmethyl)phenyl]allyloxy]ethyl acetoacetate, 140 mg of ethyl 3-aminocrotonate and 160 mg of 3-nitrobenzaldehyde, and the resulting solution was subjected to reaction under reflux for 10 hours. Subsequently, the solvent was removed by distillation under reduced pressure, and the residue thus obtained was purified by a column chromatography [Wako Silica Gel C-200, eluant: benzene:ethyl acetate (3:1 by volume)] to obtain 440 mg (yield 81.5%) of yellow, oily 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate.
IR (KBr) cm$^{-1}$: 3325, 1690, 1525, 1345.
NMR (CDCl$_3$) δ values: 1.20 (3H, t, J=7 Hz), 2.36 (6H, s), 3.51–3.80 (2H, m), 3.87–4.38 (8H, m), 5.13 (1H, s), 6.20 (1H, dt, J=16 Hz, 5 Hz), 6.52 (1H, d, J=16 Hz), 6.97–8.25 (11H, m), 8.35–8.53 (2H, m).

In the same manner as above, the following compounds were obtained:

3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate (yellow and oily)
IR (film) cm$^{-1}$: 3330, 1685, 1620, 1525, 1345.
NMR (CDCl$_3$) δ values: 1.20 (3H, t, J=7 Hz), 1.90 (3H, s), 2.39 (6H, s), 3.32–3.75 (2H, m), 3.79–4.35 (8H, m), 5.08 (1H, s), 6.37 (1H, bs), 6.46 (1H, bs), 6.83–8.13 (10H, m), 8.25–8.53 (2H, m).

3-[2-[4-(Imidazol-1-ylmethyl)phenyloxy]ethyl]5-ethyl 2,6-dimethyl-4-(3-nitrophenyl)-1,4-dihydropyridine-3,5-dicarboxylate (yellow crystals)
Melting point: 177°–179° C.
IR (KBr) cm$^{-1}$: 3300, 1690, 1520, 1345.
NMR (d$_6$-DMSO) δ values: 1.15 (3H, t, J=7 Hz), 2.37 (6H, s), 3.75–4.50 (6H, m), 5.09 (1H, s), 5.18 (2H, s), 6.72–8.20 (11H, m), 9.16 (1H, bs).

3-[2-[(E)-3-[4-(imidazol-1-ylmethyl)phenyl]allyloxy]ethyl]5-ethyl 2,6-dimethyl-4-(3-nitrophenyl)-1,4-dihydropyridine-3,5-dicarboxylate (yellow powders)
IR (KBr) cm$^{-1}$: 1695, 1530, 1350.
NMR (CDCl$_3$) δ values: 1.22 (3H, t, J=7 Hz), 2.37 (6H, s), 3.51–3.82 (2H, m), 3.88–4.44 (6H, m), 5.15 (3H, bs), 6.29–8.32 (14H, m).

3-[2-[4-(Pyridin-3-ylmethyl)phenyloxy]ethyl]5-ethyl 2,6-dimethyl-4-(3-nitrophenyl)-1,4-dihydropyridine-3,5-dicarboxylate (yellow powders)
IR (KBr) cm$^{-1}$: 3320, 1690, 1520, 1345.
NMR (CDCl$_3$) δ values: 1.20 (3H, t, J=7 Hz), 2.36 (6H, s), 3.75–4.65 (8H, m), 5.14 (1H, s), 6.60–8.24 (11H, m), 8.30–8.63 (2H, m).

3-[3-[(E)-3-[4-(pyridin-3-ylmethyl)phenyl]-2-methylallyloxy]-2,2-dimethylpropyl]5-methyl 2,6-dimethyl-4-(3-nitrophenyl)-1,4-dihydropyridine-3,5-dicarboxylate (yellow and oily)
IR (film) cm$^{-1}$: 3330, 1685, 1520, 1345.
NMR (CDCl$_3$) δ values:

| 0.91 (6H, s), 1.80 (3H, bs), | 2.31 (s) 2.37 (s) | } (6H), |
|---|---|---|
| 3.11 (2H, s), 3.66 (3H, s), | 3.89–3.99 (m) 3.92 (s) | } (6H), |

5.14 (1H, s), 6.36 (1H, bs), 6.95–8.13 (11H, m), 8.32–8.55 (2H, m).

3-[4-[(E)-3-[4-(pyridin-3-ylmethyl)phenyl]-2-methylallyloxy]butyl]5-ethyl 2,6-dimethyl-4-(3-nitrophenyl)-1,4-dihydropyridine-3,5-dicarboxylate (yellow and oily)
IR (film) cm$^{-1}$: 3300, 1680, 1520, 1345.
NMR (CDCl$_3$) δ values: 1.21 (3H, t, J=7 Hz), 1.44–1.80 (4H, m), 1.85 (3H, bs), 2.35 (6H, bs), 3.42 (2H, t,

| J=6 Hz), | 3.86–4.28 (m) 3.97 (s) | } (8H), 5.11 (1H, s), |
|---|---|---|

5.98 (1H, bs), 6.42 (1H, bs), 6.98–8.18 (10H, m), 8.34–8.58 (2H, m).

3-[5-[(E)-3-[4-(pyridin-3-ylmethyl)phenyl]-2-methylallyloxy]pentyl]5-ethyl 2,6-dimethyl-4-(3-nitrophenyl)-1,4-dihydropyridine-3,5-dicarboxylate (yellow and oily)
IR (KBr) cm$^{-1}$: 3300, 1680, 1520, 1350.
NMR (CDCl$_3$) δ values:

| 0.85–1.95 (m) 1.21 (t, J=7 Hz) 1.84 (bs) | } (12H), 2.34 (6H, bs), |
|---|---|

3.18–3.55 (2H, m), 3.80–4.26 (8H, m), 5.10 (1H, s), 6.17 (1H, bs), 6.43 (1H, bs), 6.83–8.15 (10H, m), 8.28–8.60 (2H, m).

3-[3-[(E)-3-[4-(pyridin-3-ylmethyl)phenyl]-2-methylallyloxy]-1-methylpropyl]5-ethyl 2,6-dimethyl-4-(3-nitrophenyl)-1,4-dihydropyridine-3,5-dicarboxylate (yellow and oily)
IR (KBr) cm$^{-1}$: 3300, 1680, 1520, 1345.
NMR (CDCl$_3$) δ values: 1.00–1.50 (6H, m), 1.75–2.10 (5H, m), 2.43

| | | |
|---|---|---|
| (6H, bs), 3.21 (t, J=6 Hz) | | |
| 3.61 (t, J=6 Hz) | } (2H), | |
| 3.80–4.40 (m) } (6H), | 4.85–5.45 (m) } (2H), | |
| 3.89 (s) | 5.21 (s) | |
| 6.41 (bs) } (1H), 6.83 (1H, bs), | | |
| 6.51 (bs) | | |

7.01–8.73 (12H, m).

3-[3-[(E)-3-[4-(pyridin-3-ylmethyl)phenyl]-2-methylallyloxy]-2-methylpropyl]5-ethyl 2,6-dimethyl-4-(3-nitrophenyl)-1,4-dihydropyridine-3,5-dicarboxylate (yellow and oily)

IR (KBr) cm$^{-1}$: 3300, 1680, 1520, 1345.

NMR (CDCl$_3$) δ values: 0.91 (3H, d, J=6 Hz), 1.23 (3H, t, J=7 Hz),

| | |
|---|---|
| 1.83 (3H, bs), 2.00–2.60 (m) } (7H), | |
| 2.34 (bs) | |
| 3.27 (2H, d, J=6 Hz), 3.56–4.30 (m) } (8H) | |
| 3.97 (s) | |

5.13 (1H, s), 6.36 (1H, bs), 6.58 (1H, bs), 6.70–8.56 (12H, m).

3-[3-[(E)-3-[4-(pyridin-3-ylmethyl)phenyl]-2-methylallyloxy]-2,2-dimethylpropyl]5-ethyl 2,6-dimethyl-4-(3-nitrophenyl)-1,4-dihydropyridine-3,5-dicarboxylate (yellow powders)

IR (KBr) cm$^{-1}$: 3330, 1680, 1520, 1340.

NMR (CDCl$_3$) δ values: 0.90 (6H, bs), 1.25 (3H, t, J=7 Hz), 1.80 (3H,

| | |
|---|---|
| bs), 2.32 (s) } (6H), 3.13 (2H, s), | |
| 2.37 (s) | |

3.82–4.04 (6H, m), 4.12 (2H, q, J=7 Hz), 5.19 (1H, s), 6.39 (1H, bs), 6.88 (1H, bs), 7.00–8.22 (10H, m), 8.30–8.58 (2H, m).

3-[3-[(E)-3-[4-(pyridin-3-ylmethyl)phenyl]-2-methylallyloxy]-2,2-dimethylpropyl]5-isopropyl-2,6-dimethyl-4-(3-nitrophenyl)-1,4-dihydropyridine-3,5-dicarboxylate (yellow and oily)

IR (KBr) cm$^{-1}$: 3320, 1675, 1520, 1340.

NMR (CDCl$_3$) δ values:

| | |
|---|---|
| 0.92 (6H, bs), 1.18 (d, J=6 Hz) } (6H), | |
| 1.28 (d, J=6 Hz) | |
| 1.81 (3H, bs), 2.32 (s) } (6H), 3.12 (2H, s), | |
| 2.37 (s) | |
| 3.90 (bs) } (6H), 4.62–5.15 (m) } (2H), | |
| 3.95 (s) | 5.15 (s) |

6.34 (1H, bs), 6.90–8.16 (11H, m), 8.32–8.47 (2H, m).

3-[3-[(E)-3-[4-(pyridin-3-ylmethyl)phenyl]-2-methylallyloxy]-1,3-dimethylpropyl]5-ethyl 2,6-dimethyl-4-(3-nitrophenyl)-1,4-dihydropyridine-3,5-dicarboxylate (yellow and oily)

IR (film) cm$^{-1}$: 3320, 1685, 1525, 1350.

NMR (CDCl$_3$) δ values:

| | |
|---|---|
| 0.78–2.10 (m) } (14H), 2.31 (6H, bs), | |
| 1.82 (bs) | |
| 3.32–4.30 (m) } (7H), 4.84–5.24 (m) } (2H), | |
| 3.97 (s) | 5.10 (s) |

6.18 (1H, bs), 6.36 (1H, bs), 6.90–8.18 (10H, m), 8.30–8.54 (2H, m).

3-[3-[(E)-3-[4-(pyridin-3-ylmethyl)phenyl]allyloxy]-2,2-dimethylpropyl]5-ethyl 2,6-dimethyl-4-(3-nitrophenyl)-1,4-dihydropyridine-3,5-dicarboxylate IR (KBr) cm$^{-1}$: 3320, 1680, 1520, 1345.

NMR (CDCl$_3$) δ values: 0.88 (6H, bs), 1.25 (3H, t, J=7 Hz),

| | |
|---|---|
| 2.32 (s) } (6H), 3.15 (2H, s), 3.90–4.29 (8H, m), | |
| 2.36 (s) | |

5.17 (1H, s), 6.10 (1H, dt, J=16 Hz, 5 Hz), 6.53 (1H, d, J=16 Hz), 7.00–8.16 (11H, m), 8.30–8.52 (2H, m).

3-[3-[(E)-3-[4-(pyridin-3-ylmethyl)phenyl]-2-methylallyloxy]-2,2-dimethylpropyl]5-methyl 2,6-dimethyl-4-(3-fluorophenyl)-1,4-dihydropyridine-3,5-dicarboxylate (yellow powders)

IR (KBr) cm$^{-1}$: 3320, 1680.

NMR (CDCl$_3$) δ values:

| | | |
|---|---|---|
| 0.88 (s) } (6H), 1.80 (3H, bs), 2.27 (s) } (6H), | | |
| 0.90 (s) | | 2.33 (s) |

3.10 (2H, s), 3.65 (3H, s), 3.80–4.02 (6H, m),

| | |
|---|---|
| 5.09 (1H, s), 6.39 (1H, bs), 6.60–7.60 (m) } (11H), | |
| 6.89 (bs) | |

8.28–8.52 (2H, m).

3-[3-[(E)-3-[4-(pyridin-3-ylmethyl)phenyl]-2-methylallyloxy]-2,2-dimethylpropyl]5-ethyl 2,6-dimethyl-4-(2,3-dichlorophenyl)-1,4-dihydropyridine-3,5-dicarboxylate (yellow and oily)

IR (KBr) cm$^{-1}$: 3330, 1685.

NMR (CDCl$_3$) δ values: 0.89 (6H, bs), 1.18 (3H, t, J=7 Hz), 1.82 (3H, bs), 2.26 (6H, bs), 3.13 (2H, s), 3.85–4.22 (8H, m), 5.51 (1H, s), 6.25 (1H, bs), 6.41 (1H, bs), 6.95–7.60 (9H, m), 8.34–8.54 (2H, m).

3-[3-[(E)-3-[4-(pyridin-3-ylmethyl)phenyl]-2-methylallyloxy]-2,2-dimethylpropyl]5-ethyl 2,6-dimethyl-4-(2-trifluoromethylphenyl)-1,4-dihydropyridine-3,5-dicarboxylate (yellow and oily)

IR (KBr) cm$^{-1}$: 3330, 1685.

NMR (CDCl$_3$) δ values: 0.89 (6H, bs), 1.15 (3H, t, J=7 Hz), 1.80

| | |
|---|---|
| (3H, bs), 2.20 (s) } (6H), 3.11 (2H, s), | |
| 2.26 (s) | |
| 3.68–4.17 (m) | |
| 3.90 (s) } (8H), 5.57 (1H, s), | |
| 3.97 (s) | |
| 6.20–6.44 (m) } (2H), 6.90–7.60 (10H, m), | |

6.41 (bs)

8.25–8.50 (2H, m).

3-[3-[(E)-3-[4-(pyridin-3-ylmethyl)phenyl]-2-methylallyloxy]-2,2-dimethylpropyl]5-isopropyl-2,6-dimethyl-4-(2-fluorophenyl)-1,4-dihydropyridine-3,5-dicarboxylate (yellow and oily)

IR (film) cm$^{-1}$: 3330, 1685.

NMR (CDCl$_3$) δ values:

| 0.94 (6H, bs), | 1.10 (d, J=6 Hz) | (6H), | | |
| | 1.24 (d, J=6 Hz) | | | |
| 1.81 (3H, bs), | 2.26 (s) | (6H), | 3.17 (2H, s), | |
| 2.30 (s) | | | | |
| 3.85–3.95 (m) | (6H), | 4.75–5.35 (m) | (2H), | |
| 3.90 (s) | | 5.30 (s) | | |

6.39 (1H, bs), 6.80–7.67 (11H, m), 8.30–8.50 (2H, m).

3-[6-[(E)-3-[4-(pyridin-3-ylmethyl)phenyl]-2-methylallyloxy]hexyl]5-ethyl 2,6-dimethyl-4-(3-nitrophenyl)-1,4-dihydropyridine-3,5-dicarboxylate (yellow and oily)

IR (film) cm$^{-1}$: 3330, 1680.

NMR (CDCl$_3$) δ values:

| 1.10–2.10 (m) | (14H), 2.37 (6H, bs), |
| 1.89 (bs) | |

3.28–3.78 (2H, m), 3.80–4.45 (8H, m), 5.12 (1H, s), 6.47 (1H, bs), 6.98–8.25 (11H, m), 8.35–8.60 (2H, m).

3-[3-[(E)-3-[4-(pyridin-3-yloxy)phenyl]-2-methylallyloxy]-2,2-dimethylpropyl]5-ethyl 2,6-dimethyl-4-(3-nitrophenyl)-1,4-dihydropyridine-3,5-dicarboxylate (yellow and oily)

IR (film) cm$^{-1}$: 3320, 1675.

NMR (CDCl$_3$) δ values: 0.94 (6H, s), 1.28 (3H, t, J=7 Hz),

| 1.83 (3H, bs), | 2.34 (s) | (6H), 3.14 (2H, s), |
| | 2.42 (s) | |
| 3.77–4.33 (m) | (6H), 5.19 (1H, bs), | |
| 3.93 (bs) | | |

6.38 (1H, bs), 6.77–8.48 (13H, m).

(3) In 4.4 ml of ethanol was dissolved 440 mg of 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate, and to the resulting solution was added 0.26 ml of 4.23N hydrochloric acid (dioxane solution) with ice-cooling, after which the resulting mixture was stirred at the same temperature for 15 minutes. The solvent was removed by distillation under reduced pressure to obtain 470 mg of yellow powders of 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate hydrochloride.

IR (KBr) cm$^{-1}$: 3420–3200, 1685, 1520, 1345.

Example 28

In 8 ml of tetrahydrofuran was dissolved 400 mg of 2-[3-[4-(pyridin-3-ylmethyl)phenyl]propyloxy]ethanol, and one drop of triethylamine was added to the resulting solution. To the solution was added dropwise a mixture of 150 mg of diketene and 2 ml of tetrahydrofuran under reflux over one hour, and the resulting mixture was subjected to reaction at the same temperature for 30 minutes, after which the solvent was removed by distillation under reduced pressure to obtain 500 mg of an oily product. In 10 ml of ethanol were dissolved this oily product, 220 mg of ethyl 3-aminocrotonate and 260 mg of 3-nitrobenzaldehyde, and the resulting solution was subjected to reaction under reflux for 10 hours. Subsequently, the solvent was removed by distillation under reduced pressure, and the residue thus obtained was purified by a column chromatography [Wako Silica Gel C-200, eluant: benzene:ethyl acetate (3:1 by volume)] to obtain 550 mg (yield 63.0%) of yellow, oily 3-[2-[3-[4-(pyridin-3-ylmethyl)phenyl]propyloxy]ethyl]5-ethyl 2,6-dimethyl-4-(3-nitrophenyl)-1,4-dihydropyridine-3,5-dicarboxylate.

IR (KBr) cm$^{-1}$: 3330, 1690, 1525, 1345.

NMR (CDCl$_3$) δ values: 1.19 (3H, t, J=7 Hz), 1.62–2.10 (2H, m), 2.36 (6H, s), 2.46–2.82 (2H, m), 3.37–3.72 (4H, m), 3.86–4.43 (6H, m), 5.09 (1H, s), 6.93–8.17 (11H, m), 8.27–8.50 (2H, m).

In the same manner as above, the following compounds were obtained:

3-[2-[(E)-3-[5-(pyridin-3-ylmethyl)thiophen-2-yl]-2-methylallyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3325, 1685, 1525, 1350.

NMR (CDCl$_3$) δ values: 1.17 (3H, t, J=7 Hz), 1.89 (3H, s), 2.33 (6H, s), 3.43–3.71 (2H, m), 3.85–4.35 (8H, m), 5.10 (1H, s), 6.34–8.17 (10H, m), 8.28–8.59 (2H, m).

3-[2-[(E)-3-[4-(pyridin-3-yloxy)phenyl]-2-methylallyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3320, 1680, 1640, 1620, 1525, 1345.

NMR (CDCl$_3$) δ values: 1.22 (3H, t, J=7 Hz), 1.90 (3H, s), 2.38 (6H, s), 3.48–3.84 (2H, m), 3.84–4.92 (6H, m), 5.16 (1H, s), 6.24–8.42 (14H, m).

3-[2-[4-(Imidazol-1-ylmethyl)benzyloxy]ethyl]5-ethyl 2,6-dimethyl-4-(3-nitrophenyl)-1,4-dihydropyridine-3,5-dicarboxylate (yellow powders)

IR (KBr) cm$^{-1}$: 1680, 1640, 1520, 1345.

NMR (CDCl$_3$) δ values: 1.20 (3H, t, J=7 Hz), 2.36 (6H, s), 3.50–3.80 (2H, m), 3.89–4.40 (4H, m), 4.53 (2H, s), 5.17 (3H, s), 6.96–8.26 (12H, m).

3-[2-[3-[4-(Imidazol-1-ylmethyl)phenyl]propyloxy]ethyl]5-ethyl 2,6-dimethyl-4-(3-nitrophenyl)-1,4-dihydropyridine-3,5-dicarboxylate (yellow powders)

IR (KBr) cm$^{-1}$: 1685, 1640, 1525, 1350.

NMR (CDCl$_3$) δ values: 1.20 (3H, t, J=7 Hz), 1.71–2.11 (2H, m), 2.38 (6H, s), 2.58–2.84 (2H, m), 3.39–3.78 (4H, m), 3.95–4.37 (4H, m), 5.16 (2H, s), 5.23 (1H, s), 7.03–8.32 (12H, m).

3-[2-[3-[4-(Pyridin-3-yloxy)phenyl]propyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3325, 1690, 1650, 1620, 1525, 1350.

NMR (CDCl$_3$) δ values: 1.22 (3H, t, J=7 Hz), 1.60–2.18 (2H, m), 2.38 (6H, s), 2.30–3.00 (2H, m), 3.30–3.80 (4H, m), 3.80–4.40 (4H, m), 5.15 (1H, s), 6.70–8.95 (13H, m).

3-[2-[4-(Pyridin-3-ylmethyl)benzyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3340, 1690, 1530, 1345.

NMR (CDCl$_3$) δ values: 1.15 (3H, t, J=7 Hz), 2.28 (3H, s), 2.31 (3H, s),

| 3.37–3.70 (2H, m), 3.78–4.28 (m) 3.91 (s) | (6H), |
|---|---|

4.41 (2H, s), 5.05 (1H, s), 6.68 (1H, bs), 6.83–8.06 (10H, m), 8.21–8.53 (2H, m).

3-[2-[2-[4-(Pyridin-3-ylmethyl)phenyl]ethyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3325, 3200, 1690, 1525, 1350.

NMR (CDCl$_3$) δ values: 1.21 (3H, t, J=7 Hz), 2.27 (3H, s), 2.41 (3H, s),

| 2.87 (2H, t, J=6 Hz), 3.25–4.45 (m) 3.95 (s) | (10H), |
|---|---|

5.19 (1H, s), 6.56–8.30 (11H, m), 8.38–8.65 (2H, m).

3-[2-[(E)-3-[4-(pyridin-3-ylmethyl)phenyl]allylthio]ethyl]5-ethyl 2,6-dimethyl-4-(3-nitrophenyl)-1,4-dihydropyridine-3,5-dicarboxylate (yellow and oily)

IR (film) cm$^{-1}$: 3325, 1690, 1525, 1350.

NMR (CDCl$_3$) δ values: 1.20 (3H, t, J=7 Hz), 2.33 (6H, s), 2.66 (2H, t,

| J=7 Hz), 3.29 (2H, d, J=6 Hz), 3.82–4.37 (m) 3.97 (s) | (6H), |
|---|---|

5.09 (1H, s), 6.02 (1H, dt, J=16 Hz, 5 Hz), 6.42 (1H, d, J=16 Hz), 6.73–8.21 (11H, m), 8.39–8.53 (2H, m).

3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate (yellow powders)

IR (KBr) cm$^{-1}$: 3320, 1685, 1520, 1345.

NMR (CDCl$_3$) δ values: 1.18 (3H, t, J=7 Hz), 2.34 (6H, s), 3.35–4.63 (10H, m), 5.10 (1H, s), 6.18 (1H, dt, J=16 Hz, 5 Hz), 6.52 (1H, d, J=16 Hz), 6.88–8.20 (11H, m), 8.28–8.52 (2H, m).

3-[2-[2-[(E)-3-[4-(pyridin-3-ylmethyl)phenyl]allyloxy]ethyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3320, 2950, 1680, 1520, 1345, 1210.

NMR (CDCl$_3$) δ values: 1.19 (3H, t, J=7 Hz), 1.55–2.07 (2H, m), 2.29 (6H, s), 3.10–3.57 (2H, m), 3.82–4.36 (8H, m),

| 5.05 (1H, s), | 6.07 (dt, J=16 Hz, 5 Hz) 6.52 (d, J=16 Hz) 6.64 (bs) | (3H), |
|---|---|---|

6.87–8.19 (10H, m), 8.27–8.47 (2H, m).

3-[2-[2-[(E)-3-[4-(pyridin-3-ylmethyl)phenyl]allyloxy]ethyloxy]ethyl]5-ethyl 2,6-dimethyl-4-(3-nitrophenyl)-1,4-dihydropyridine-3,5-dicarboxylate (yellow and oily)

IR (film) cm$^{-1}$: 3320, 2970, 2920, 1685, 1520, 1345.

NMR (CDCl$_3$) δ values: 1.20 (3H, t, J=7 Hz), 2.34 (6H, s), 3.47–3.77 (6H, m), 3.83–4.34 (8H, m), 5.11 (1H, s),

| 6.17 (dt, J=16 Hz, 5 Hz) 6.56 (bs) 6.60 (d, J=16 Hz) | (3H), |
|---|---|

6.94–8.19 (10H, m), 8.34–8.56 (2H, m).

3-[2-[(E)-3-[4-(pyridin-3-ylmethyl)phenyl]allyloxy]-1-methylethyl]5-ethyl 2,6-dimethyl-4-(3-nitrophenyl)-1,4-dihydropyridine-3,5-dicarboxylate (yellow and oily)

IR (film) cm$^{-1}$: 3320, 2970, 1680, 1520, 1345.

NMR (CDCl$_3$) δ values:

| 1.08 (d, J=6 Hz) 1.19 (t, J=7 Hz) 1.20 (d, J=6 Hz) | (6H), 2.34 (6H, s), |
|---|---|
| 3.37 (d, J=6 Hz) 3.52 (d, J=6 Hz) | (2H), 3.79–4.28 (7H, m), |

5.10 (1H, s), 5.88–8.22 (13H, m), 8.32–8.60 (2H, m).

Example 29

In 10 ml of ethanol were dissolved 1.0 g of 2-[(E)-3-[4-(pyridin-3-ylmethyl)phenyl]allyloxy]ethyl acetoacetate, 330 mg of methyl 3-aminocrotonate and 430 mg of 3-nitrobenzaldehyde, and the resulting solution was subjected to reaction under reflux for 9 hours. Subsequently, the solvent was removed by distillation under reduced pressure, and the residue thus obtained was purified by a column chromatography [Wako Silica Gel C-200, eluant: toluene:ethyl acetate (1:1 by volume)] to obtain 1.0 g (yield 60.6%) of yellow, oily 3-[2-[(E)-3-[4-(pyridin-3-ylmethyl)phenyl]allyloxy]ethyl]5-methyl 2,6-dimethyl-4-(3-nitrophenyl)-1,4-dihydropyridine-3,5-dicarboxylate.

IR (film) cm$^{-1}$: 3325, 1685, 1520, 1345.

NMR (CDCl$_3$) δ values:

| 2.33 (6H, s), | 3.44–3.75 (m) 3.57 (s) | (5H), |
|---|---|---|

3.85–4.34 (6H, m), 5.10 (1H, s), 6.11 (1H, dt, J=16 Hz, 5 Hz), 6.54 (1H, d, J=16 Hz), 6.77–8.13 (11H, m), 8.30–8.56 (2H, m).

In the same manner as above, the following compounds were obtained:

3-[2-[(E)-3-[4-(pyridin-3-ylmethyl)phenyl]allyloxy]ethyl]5-isopropyl 2,6-dimethyl-4-(3-nitrophenyl)-1,4-dihydropyridine-3,5-dicarboxylate (yellow and oily)

IR (film) cm$^{-1}$: 3325, 1685, 1650, 1620, 1520, 1345.

NMR (CDCl$_3$) δ values: 1.10 (3H, d, J=6 Hz), 1.25 (3H, d, J=6 Hz), 2.38 (6H, s), 3.44–3.82 (2H, m),

| 3.90–4.40 (m) 3.95 (s) | (6H), | 4.60–5.22 (m) 5.16 (s) | (2H), |
|---|---|---|---|

5.98–6.85 (3H, m), 6.96–8.60 (12H, m).

3-[2-[(E)-3-[4-(pyridin-3-ylmethyl)phenyl]allyloxy]ethyl]5-(2-methoxy)ethyl 2,6-dimethyl-4-(3-nitrophenyl)-1,4-dihydropyridine-3,5-dicarboxylate (yellow and oily)

IR (film) cm$^{-1}$: 3350, 1690, 1650, 1620, 1525, 1350.
NMR (CDCl$_3$) δ values: 2.35 (6H, s), 3.30 (3H, s), 3.38–3.80 (4H, m),

| 3.80–4.40 (m) | | |
|---|---|---|
| 3.95 (s) | } (8H), 5.15 (1H, s), 5.90–6.80 | |

(3H, m), 6.98–8.60 (12H, m).

3-[2-[(E)-3-[4-(pyridin-3-ylmethyl)phenyl]allyloxy]ethyl]5-[2-(N-benzyl-N-methylamino)ethyl]2,6-dimethyl-4-(3-nitrophenyl)-1,4-dihydropyridine-3,5-dicarboxylate (yellow and oily)

IR (film) cm$^{-1}$: 3300, 1690, 1650, 1620, 1520, 1345.
NMR (CDCl$_3$) δ values: 2.12 (3H, s), 2.31 (6H, s), 2.58 (2H, t, J=6 Hz),

| 3.32–3.74 (m) | | 3.80–4.35 (m) | |
|---|---|---|---|
| 3.42 (s) | } (4H), | 3.90 (s) | } (8H), |

5.10 (1H, s), 6.05 (1H, dt, J=16 Hz, 5 Hz), 6.50 (1H, d, J=16 Hz), 6.75–8.48 (18H, m).

3-[2-[(E)-3-[4-(pyridin-3-ylmethyl)phenyl]-2-methylallyloxy]ethyl]5-methyl 2,6-dimethyl-4-(3-nitrophenyl)-1,4-dihydropyridine-3,5-dicarboxylate (yellow and oily)

IR (CHCl$_3$) cm$^{-1}$: 3325, 1695, 1525, 1350.
NMR (CDCl$_3$) δ values:

| 1.87 (3H, s), 2.36 (6H, s), | 3.44–3.80 (m) | |
|---|---|---|
| | 3.59 (s) | } (5H), |

3.80–4.37 (6H, m), 5.14 (1H, s), 6.32 (1H, bs), 6.48 (1H, bs), 7.03–8.69 (12H, m).

3-[2-[(E)-3-[4-(pyridin-3-ylmethyl)phenyl]-2-methylallyloxy]ethyl]5-isopropyl 2,6-dimethyl-4-(3-nitrophenyl)-1,4-dihydropyridine-3,5-dicarboxylate Melting point: 124°–126° C. (recrystallization solvent: acetonitrile).
IR (KBr) cm$^{-1}$: ν$_{C=O}$ 1695, 1640.
NMR (CDCl$_3$) δ values: 1.08 (3H, d, J=6 Hz), 1.24 (3H, d, J=6 Hz), 1.87 (3H, s), 2.35 (6H, s), 3.44–3.76 (2H, m),

| 3.82–4.35 (6H, m), | 4.68–5.20 (m) | |
|---|---|---|
| | 5.12 (s) | } (2H), |

6.41 (1H, bs), 6.94–8.23 (11H, m), 8.32–8.56 (2H, m).

Example 30

In 5 ml of ethanol were dissolved 500 mg of 2-[(E)-3-[4-(3-pyridylmethyl)phenyl]allyloxy]ethyl acetoacetate, 0.20 g of methyl 3-aminocrotonate and 300 mg of 3-trifluoromethylbenzaldehyde, and the resulting solution was subjected to reaction under reflux for 15 hours. Subsequently, the solvent was removed by distillation under reduced pressure, and the residue thus obtained was purified by a column chromatography [Wako Silica Gel C-200, eluant: chloroform:ethanol (100:1 by volume)] to obtain 660 mg (yield 72.8%) of pale yellow powders of 3-[2-[(E)-3-[4-(pyridin-3-ylmethyl)phenyl]allyloxy]ethyl]5-methyl 2,6-dimethyl-4-(3-trifluoromethylphenyl)-1,4-dihydropyridine-3,5-dicarboxylate.

IR (KBr) cm$^{-1}$: 3320, 1685, 1640, 1615.
NMR (CDCl$_3$) δ values:

| 2.27 (6H, s), | 3.53 (s) | |
|---|---|---|
| | 3.43–3.70 (m) | } (5H), |

3.83–4.28 (6H, m), 5.01 (1H, s), 6.05 (1H, dt, J=16 Hz, 5 Hz), 6.48 (1H, d, J=16 Hz), 6.73 (1H, s), 6.86–7.43 (10H, m), 8.21–8.36 (2H, m).

In the same manner as above, the following compounds were obtained:

3-[2-[(E)-3-[4-(pyridin-3-ylmethyl)phenyl]allyloxy]ethyl]5-methyl 2,6-dimethyl-4-(2-trifluoromethylphenyl)-1,4-dihydropyridine-3,5-dicarboxylate (pale yellow powders)

IR (KBr) cm$^{-1}$: 3320, 1695, 1640, 1615.
NMR (CDCl$_3$) δ values:

| 2.23 (6H, s), | 3.45–3.68 (m) | |
|---|---|---|
| | 3.52 (s) | } (5H), |

3.80–4.24 (6H, m), 5.52 (1H, s), 6.08 (1H, dt, J=16 Hz, 5 Hz), 6.50 (1H, d, J=16 Hz), 6.69 (1H, bs), 6.92–7.53 (10H, m), 8.28–8.40 (2H, m).

3-[2-[(E)-3-[4-(pyridin-3-ylmethyl)phenyl]allyloxy]ethyl]5-methyl 2,6-dimethyl-4-(2,3-dichlorophenyl)-1,4-dihydropyridine-3,5-dicarboxylate (pale yellow powders)

IR (KBr) cm$^{-1}$: 3310, 1685, 1640, 1615.
NMR (CDCl$_3$) δ values:

| 2.25 (6H, s), | 3.45–3.67 (m) | |
|---|---|---|
| | 3.51 (s) | } (5H), |

3.85–4.25 (6H, m), 5.40 (1H, s), 6.04 (1H, dt,

| J=16 Hz, 5 Hz), | 6.33 (s) | |
|---|---|---|
| | 6.47 (d, J=16 Hz) | } (2H), |

6.84–7.44 (9H, m), 8.24–8.36 (2H, m).

Example 31

(1) In 5 ml of ethyl acetate was dissolved 1.26 g of 2-[N-methyl-N-[(E)-3-[4-(pyridin-3-ylmethyl)phenyl]-2-methylallyl]amino]ethanol, and to the resulting solution was dropwise added a mixture of 0.36 ml of diketene and 1 ml of ethyl acetate under reflux over one hour, after which the resulting mixture was subjected to reaction at the same temperature for 30 minutes. Subsequently, the solvent was removed by distillation under reduced pressure, and the residue thus obtained was purified by a column chromatography [Wako Silica Gel C-200, eluant: benzene:ethyl acetate (1:1 by volume)] to obtain 1.06 g (yield 65.8%) of colorless, oily 2-[N-methyl-N-[(E)-3-[4-(pyridine-3-ylmethyl)phenyl]-2-methylallyl]amino]ethyl acetoacetate.

IR (film) cm$^{-1}$: ν$_{C=O}$ 1740, 1720.

NMR (CDCl₃) δ values: 1.99 (3H, bs), 2.22 (3H, s), 2.65 (2H, t, J=6 Hz), 2.66 (3H, s), 3.05 (2H, s), 3.45 (2H, s), 3.95 (2H, s), 4.26 (2H, t, J=6 Hz), 6.39 (1H, bs), 6.92–7.68 (6H, m), 8.25–8.65 (2H, m).

In the same manner as above, the following compounds were obtained:

2-[N-methyl-N-[(E)-3-[4-(pyridin-3-ylmethyl)phenyl]allyl]amino]ethyl acetoacetate (colorless and oily)

IR (film) cm⁻¹: $\nu_{C=O}$ 1740, 1720.

NMR (CDCl₃) δ values: 2.21 (3H, s), 2.30 (3H, s), 2.65 (2H, t, J=6 Hz), 3.16 (2H, d, J=6 Hz), 3.44 (2H, s), 3.90 (2H, s), 4.22 (2H, t, J=6 Hz), 6.10 (1H, dt, J=16 Hz, 6 Hz), 6.50 (1H, d, J=16 Hz), 6.84–7.60 (6H, m), 8.22–8.62 (2H, m).

2-[N-benzyl-N-[(E)-3-[4-(pyridin-3-ylmethyl)phenyl]-2-methylallyl]amino]ethyl acetoacetate (colorless and oily)

IR (film) cm⁻¹: $\nu_{C=O}$ 1740, 1720.

NMR (CDCl₃) δ values: 1.90 (3H, bs), 2.20 (3H, s), 2.74 (2H, t, J=5 Hz), 3.14 (2H, s), 3.38 (2H, s), 3.62 (2H, s), 3.92 (2H, s), 4.21 (2H, t, J=5 Hz), 6.42 (1H, bs), 6.90–7.65 (11H, m), 8.32–8.70 (2H, m).

2-[N-methyl-N-[3-[4-(pyridin-3-ylmethyl)phenyl]propyl]amino]ethyl acetoacetate (colorless and oily)

IR (film) cm⁻¹: $\nu_{C=O}$ 1740, 1710.

2-[N-methyl-N-[(E)-3-[4-(imidazol-1-ylmethyl)phenyl]allyl]amino]ethyl acetoacetate (colorless and oily)

IR (film) cm⁻¹: $\nu_{C=O}$ 1735, 1710.

(2) In 4 ml of 2-propanol were dissolved 1.01 g of 2-[N-methyl-N-[(E)-3-[4-(pyridin-3-ylmethyl)phenyl]-2-methylallyl]amino]ethyl acetoacetate, 0.38 g of isopropyl 3-aminocrotonate and 0.40 g of 3-nitrobenzaldehyde, and the resulting mixture was subjected to reaction under reflux for 3 hours. Subsequently, the solvent was removed by distillation under reduced pressure, and the residue thus obtained was purified by a column chromatography [Wako Silica Gel C-200, eluant: benzene:ethyl acetate (1:1 by volume)] to obtain 1.28 g (yield 71.5%) of yellow, oily 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate.

IR (film) cm⁻¹: $\nu_{NH}$ 3320, $\nu_{C=O}$ 1680.

NMR (CDCl₃) δ values:

| 1.10 (d, J=6 Hz) <br> 1.22 (d, J=6 Hz) } (6H), 1.85 (3H, bs), |
|---|

2.25 (3H, s), 2.36 (6H, s), 2.60 (2H, t, J=6 Hz), 3.00 (2H, s), 3.95 (2H, s), 4.16 (2H, t,

| J=6 Hz), 4.68–5.30 (m) <br> 5.15 (s) } (2H), |
|---|

6.35 (1H, bs), 6.88–8.68 (13H, m).

In the same manner as above, the compounds shown in Tables 6 and 7 were obtained.

TABLE 6

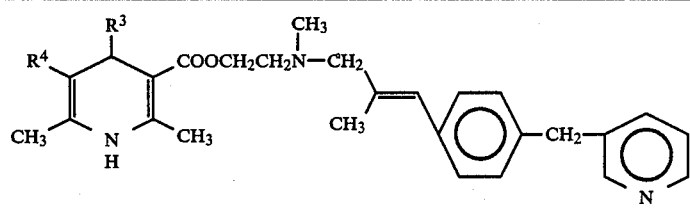

| Compound | | IR (film) | |
|---|---|---|---|
| R⁴ | R³ | cm⁻¹ | NMR (CDCl₃) δ values: |
| —COOCH₃ | ⟨phenyl⟩-NO₂ | $\nu_{NH}$ 3330 <br> $\nu_{C=O}$ 1690 <br> Yellow and oily | 1.84 (3H, bs), 2.20 (3H, s), 2.34 (6H, s), 2.60 (2H, t, J=6Hz), 2.99 (2H, s), 3.60 (3H, s), <br> 3.96 (s) <br> 4.15 (t, J=6Hz) } (4H), 5.12 (1H, s), <br> 6.36 (1H, bs), 6.48 (1H, bs), 6.98–8.23 (10H, m), 8.33–8.57 (2H, m) |
| —COOCH₂CH₃ | ⟨phenyl⟩-NO₂ | $\nu_{NH}$ 3320 <br> $\nu_{C=O}$ 1690 <br> Yellow and oily | 1.20 (3H, t, J=8Hz), 1.86 (3H, bs), 2.25 (3H, s), 2.38 (6H, s), 2.30–2.82 (2H, m), 3.00 (2H, s), <br> 3.52–4.62 (m) <br> 3.96 (s) } (6H), 5.16 (1H, s), 6.35 (1H, bs), 6.70–8.75 (13H, m) |
| —COOCH₂CH₂OCH₃ | ⟨phenyl⟩-NO₂ | $\nu_{NH}$ 3320 <br> $\nu_{C=O}$ 1690 <br> Yellow and oily | 1.82 (3H, bs), 2.20 (3H, s), 2.32 (6H, s), 2.56 (2H, t, J=6Hz), 2.96 (2H, s), 3.29 (3H, s), 3.48 (2H, t, J=6Hz), <br> 3.85–4.05 (m) <br> 3.95 (2) } (6H), 5.10 (1H, s), 6.30 (1H, bs), 6.68 (1H, bs), 6.90–8.20 (10H, m), 8.28–8.60 (2H, m) |

TABLE 6-continued

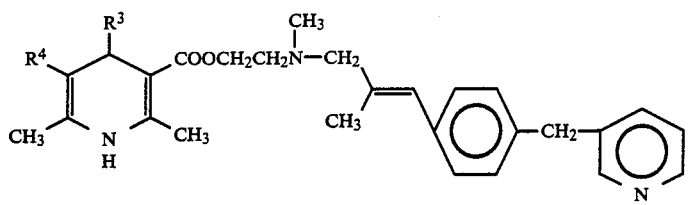

| Compound | | IR (film) | |
|---|---|---|---|
| R⁴ | R³ | cm⁻¹ | NMR (CDCl₃) δ values: |
| —COOCH(CH₃)₂ | 2-CF₃-C₆H₄ | $\nu_{NH}$ 3350<br>$\nu_{C=O}$ 1690<br>Pale yellow and oily | 1.00 (d, J=6Hz)<br>1.18 (d, J=6Hz) } (6H), 1.82 (3H, bs),<br>2.15 (s)<br>2.20 (s) } (9H), 2.60 (2H, t, J=6Hz), 3.00<br>(2H, s), 3.88–4.45 (m)<br>3.95 (s) } (4H), 4.60–5.32<br>(1H, m), 5.58 (1H, bs), 6.35 (1H, bs),<br>6.52 (1H, bs), 6.90–7.72 (10H, m),<br>8.30–8.70 (2H, m) |
| —COOCH(CH₃)₂ | 2,3-Cl₂-C₆H₃ | $\nu_{NH}$ 3320<br>$\nu_{C=O}$ 1690<br>Pale yellow and oily | 1.02 (d, J=6Hz)<br>1.20 (d, J=6Hz) } (6H), 1.82 (3H, bs),<br>2.25 (9H, bs), 2.30–2.80 (2H, m), 2.98<br>(2H, s), 3.78–4.50 (m)<br>3.94 (s) } (4H), 4.64–5.30<br>(1H, m), 5.45 (1H, s), 6.34 (1H, bs),<br>6.65–7.75 (10H, m), 8.24–8.70 (2H, m) |

TABLE 7

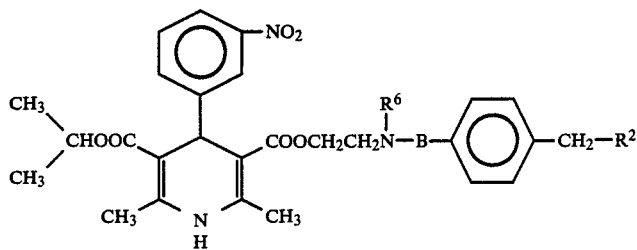

| Compound | | | IR (film) | |
|---|---|---|---|---|
| R² | R⁶ | B | cm⁻¹ | NMR (CDCl₃) δ values: |
| 4-pyridyl | —CH₃ | —CH₂—CH=CH— | $\nu_{NH}$ 3350<br>$\nu_{C=O}$ 1690<br>Yellow and oily | 1.12 (d, J=6Hz)<br>1.25 (d, J=6Hz) } (6H),<br>2.31 (s), 2.38 (s)<br>2.68 (t, J=6Hz) } (11H),<br>3.18 (2H, d, J=6Hz),<br>3.98 (s)<br>4.20 (t, J=6Hz) } (4H),<br>4.68–5.35 (m)<br>5.15 (s) } (2H), 6.12 (1H, dt,<br>J=16Hz, 6Hz), 6.54 (1H, d, J=16Hz),<br>6.92–8.72 (13H, m) |

TABLE 7-continued

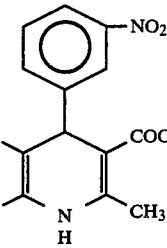

| Compound | | | IR (film) | |
|---|---|---|---|---|
| R² | R⁶ | B | cm⁻¹ | NMR (CDCl₃) δ values: |
| [pyridine ring] | —CH₂—[phenyl]— | —CH₂—C(CH₃)=CH₂ | $\nu_{NH}$ 3320 $\nu_{C=O}$ 1690 Yellow and oily | 1.10 (d, J=6Hz) } (6H), 1.84 (3H, bs), 1.22 (d, J=6Hz) 2.28 (s) } (6H), 2.70 (2H, t, J=6Hz), 2.32 (s) 3.06 (2H, s), 3.60 (2H, s), 3.80–4.30 (m) } (4H), 3.95 (s) 4.70–5.25 (m) } (2H), 6.38 (1H, bs), 5.08 (s) 6.70 (1H, bs), 6.90–8.60 (17H, m) |
| [pyridine ring] | —CH₃ | —(CH₂)₃— | $\nu_{NH}$ 3320 $\nu_{C=O}$ 1685 Yellow and oily | 1.07 (d, J=6Hz) } (6H), 1.22 (d, J=6Hz) 2.22 (s) 2.33 (s) } (17H), 1.47–2.77 (m) 3.95 (s) } (4H), 4.11 (t, J=6Hz) 4.66–5.26 (m) } (2H), 6.88 (1H, bs), 5.10 (s) 6.99–8.59 (12H, m) |
| [imidazole ring] | —CH₃ | —CH₂—CH=CH— | $\nu_{NH}$ 3320 $\nu_{C=O}$ 1690 Yellow and oily | 1.09 (d, J=6Hz) } (6H), 1.23 (d, J=6Hz) 2.28 (s) } (9H), 2.64 (2H, t, J=6Hz), 2.36 (s) 3.15 (2H, d, J=6Hz), 4.14 (2H, t, J=6Hz), 4.68–5.29 (m) } (4H), 5.09 (s) 6.12 (1H, t, J=16Hz, 6Hz), 6.50 (1H, d, J=16Hz), 6.82–8.25 (12H, m) |

Example 32

(1) In 5 ml of methylene chloride was suspended 350 mg of (E)-3-[4-(pyridin-3-yloxy)phenyl]-2-methylallyl alcohol hydrochloride and to the suspension was added 0.18 ml of thionyl chloride with ice-cooling, after which the resulting mixture was subjected to reaction under reflux for 30 minutes. The solvent and the excessive thionyl chloride were removed by distillation under reduced pressure to obtain oily (E)-3-[4-(pyridin-3-yloxy)phenyl]-2-methylallyl chloride hydrochloride. This was dissolved in 2 ml of methylene chloride.

(2) In 3 ml of methylene chloride was dissolved 760 mg of 3-(2-methylaminoethyl)5-ethyl 2,6-dimethyl-4-(3-nitrophenyl)-1,4-dihydropyridine-3,5-dicarboxylate, and to the resulting solution were added 0.35 ml of triethylamine and the methylene chloride solution obtained in (1) above with ice-cooling, after which the resulting mixture was subjected to reaction under reflux for 10 hours. The reaction mixture was washed with two 2-ml portions of water, and thereafter dried over anhydrous magnesium sulfate. The solvent was removed by distillation under reduced pressure, and the residue thus obtained was purified by a column chromatography [Wako Silica Gel C-200, eluant: benzene:ethyl acetate (2:1 by volume)] to obtain 480 mg (yield 60.8%) of yellow powders of 3-[2-[N-methyl-N-[(E)-3-[4-(pyridin-3-yloxy)phenyl]-2-methylallyl]amino]ethyl]5-ethyl 2,6-dimethyl-4-(3-nitrophenyl)-1,4-dihydropyridine-3,5-dicarboxylate. IR (KBr) cm⁻¹: $\nu_{NH}$ 3330, $\nu_{C=O}$ 1690.

NMR (CDCl₃) δ values: 1.17 (3H, t, J=8 Hz), 1.84 (3H, bs), 2.22 (3H, s), 2.34 (6H, s), 2.60 (2H, t, J=6 Hz), 2.98 (2H, s), 3.87–4.25 (4H, m), 5.10 (1H, s), 6.36 (2H, bs), 6.84–8.41 (12H, m).

(3) In 4 ml of chloroform was dissolved 400 mg of the yellow powder obtained in (2) above, and to the resulting solution was added 0.2 ml of 7N hydrochloric acid (ethanol solution) with ice-cooling, after which the resulting mixture was stirred at the same temperature for 5 minutes. The solvent was then removed by distillation under reduced pressure to obtain 440 mg of yellow powders of 3-[2-[N-methyl-N-[(E)-3-[4-(pyridin-3-yloxy)phenyl]-2-methylallyl]amino]ethyl]5-ethyl 2,6-dimethyl-4-(3-nitrophenyl)-1,4-dihydropyridine-3,5-dicarboxylate hydrochloride.

IR(KBr) cm$^{-1}$: $\nu_{C=O}$ 1680.

Example 33

(1) In 10 ml of methylene chloride was dissolved 1.0 g of 3-(2-aminoethyl)-5-isopropyl 2,6-dimethyl-4-(3-nitrophenyl)-1,4-dihydropyridine-3,5-dicarboxylate, and to the resulting solution were added 590 mg of (E)-3-[4-(pyridin-3-ylmethyl)phenyl]-2-methylacrylic aldehyde and 1.0 g of Molecular Sieves 4A, after which the resulting mixture was subjected to reaction under reflux for 3 hours. The Molecular Sieves was removed by filtration, and then the solvent was removed by distillation under reduced pressure to obtain pale yellow, oily 3-[2-[N-[(E)-3-[4-(pyridin-3-ylmethyl)phenyl]-2-methylallylidene]amino]ethyl]5-isopropyl 2,6-dimethyl-4-(3-nitrophenyl)-1,4-dihydropyridine-3,5-dicarboxylate. This was dissolved in 8 ml of ethanol.

(2) To the ethanol solution obtained in (1) above was added 0.10 g of sodium boron hydride in portions with ice-cooling, after which the resulting mixture was subjected to reaction with ice-cooling for 30 minutes. Subsequently, 0.15 ml of acetic acid was added to the reaction mixture, and the solvent was removed by distillation under reduced pressure, after which to the residue thus obtained were added 20 ml of methylene chloride and 20 ml of water to form a solution. The organic layer was separated, washed successively with 20 ml of water and 10 ml of a saturated aqueous sodium chloride solution, and thereafter dried over anhydrous magnesium sulfate. The solvent was removed by distillation under reduced pressure, and the residue thus obtained was purified by a column chromatography [Wako Silica Gel C-200, eluant: chloroform:ethanol (20:1 by volume)] to obtain 1.33 g (yield 85.8%) of yellow, oily 3-[2-[N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate.

IR (film) cm$^{-1}$: $\nu_{NH}$ 3300, $\nu_{C=O}$ 1685.

NMR (CDCl$_3$) δ values:

1.09 (d, J=6 Hz)  
1.22 (d, J=6 Hz) } (6H), 1.53 (1H, bs), 1.84 (3H, bs), 2.35 (6H, s), 2.80 (2H, t, J=6 Hz), 3.25 (2H, s), 3.95 (s)  
4.15 (t, J=6 Hz) } (4H), 4.70–5.25 (m) 5.07 (s) } (2H), 6.31 (1H, bs), 6.68 (1H, bs), 6.94–8.59 (12H, m).

Example 34

In the same manner as in Example 32-(3), reaction was effected to obtain the following compound: 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate hydrochloride (yellow powders)

IR (KBr) cm$^{-1}$: $\nu_{C=O}$ 1690.

Example 35

(1) In 1.36 ml of isopropanol were dissolved 340 mg of 2-[(E)-3-[4-(pyridin-3-ylmethyl)phenyl]-2-methylallyloxy]ethyl 3-aminocrotonate and 257 mg of isopropyl 2-(3-nitrobenzylidene)acetoacetate, and the resulting solution was subjected to reaction under reflux for 2 hours. The reaction mixture was thereafter stirred with ice-cooling, and the crystals thus precipitated were collected by filtration to obtain 440 mg (yield 75.8%) of 3-[2-[(E)-3-[4-(pyridin-3-ylmethyl)phenyl]-2-methylallyloxy]ethyl]5-isopropyl 2,6-dimethyl-4-(3-nitrophenyl)-1,4-dihydropyridine-3,5-dicarboxylate having a melting point of 124°–126° C.

The physical properties of this product were identical with those of the compound obtained in Example 29.

In the same manner as above, the following compounds were obtained:

3-[2-[(E)-3-[4-(pyridin-3-ylmethyl)phenyl]-2-methylallyloxy]ethyl]5-ethyl 2,6-dimethyl-4-(3-nitrophenyl)-1,4-dihydropyridine-3,5-dicarboxylate 3-[2-[4-(Imidazol-1-ylmethyl)phenyloxy]ethyl]5-ethyl 2,6-dimethyl-4-(3-nitrophenyl)-1,4-dihydropyridine-3,5-dicarboxylate 3-[2-[(E)-3-[4-(imidazol-1-ylmethyl)phenyl]allyloxy]ethyl]5-ethyl 2,6-dimethyl-4-(3-nitrophenyl)-1,4-dihydropyridine-3,5-dicarboxylate 3-[2-[4-(Pyridin-3-ylmethyl)phenyloxy]ethyl]5-ethyl 2,6-dimethyl-4-(3-nitrophenyl)-1,4-dihydropyridine-3,5-dicarboxylate 3-[2-[3-[4-(Pyridin-3-ylmethyl)phenyl]propyloxy]ethyl]5-ethyl 2,6-dimethyl-4-(3-nitrophenyl)-1,4-dihydropyridine-3,5-dicarboxylate 3-[2-[(E)-3-[5-(pyridin-3-ylmethyl)thiophen-2-yl]-2-methylallyloxy]ethyl]5-ethyl 2,6-dimethyl-4-(3-nitrophenyl)-1,4-dihydropyridine-3,5-dicarboxylate 3-[2-[(E)-3-[4-(pyridin-3-yloxy)phenyl]-2-methylallyloxy]ethyl]5-ethyl 2,6-dimethyl-4-(3-nitrophenyl)-1,4-dihydropyridine-3,5-dicarboxylate 3-[2-[4-(Imidazol-1-ylmethyl)benzyloxy]ethyl]5-ethyl 2,6-dimethyl-4-(3-nitrophenyl)-1,4-dihydropyridine-3,5-dicarboxylate 3-[2-[3-[4-(Imidazol-1-ylmethyl)phenyl]propyloxy]ethyl]5-ethyl 2,6-dimethyl-4-(3-nitrophenyl)-1,4-dihydropyridine-3,5-dicarboxylate 3-[2-[3-[4-(Pyridin-3-yloxy)phenyl]propyloxy]ethyl]5-ethyl 2,6-dimethyl-4-(3-nitrophenyl)-1,4-dihydropyridine-3,5-dicarboxylate 3-[2-[4-(Pyridin-3-ylmethyl)benzyloxy]ethyl]5-ethyl 2,6-dimethyl-4-(3-nitrophenyl)-1,4-dihydropyridine-3,5-dicarboxylate 3-[2-[2-[4-(Pyridin-3-ylmethyl)phenyl]ethyloxy]ethyl]5-ethyl 2,6-dimethyl-4-(3-nitrophenyl)-1,4-dihydropyridine-3,5-dicarboxylate 3-[2-[(E)-3-[4-(pyridin-3-ylmethyl)phenyl]allylthio]ethyl]5-ethyl 2,6-dimethyl-4-(3-nitrophenyl)-1,4-dihydropyridine-3,5-dicarboxylate 3-[2-[(E)-3-[4-(pyridin-4-ylmethyl)phenyl]allyloxy]ethyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]allyloxy]propyl]5-ethyl 2,6-dimethyl-4-(3-nitrophenyl)-1,4-dihydropyridine-3,5-dicarboxylate 3-[2-[2-[(E)-3-[4-(pyridin-3-ylmethyl)phenyl]allyloxy]ethyloxy]ethyl]5-ethyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]-1-methylethyl]5-ethyl 2,6-dimethyl-4-(3-nitropheny)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-isopropyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-(2-methoxy)ethyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-[2-(N-benzyl-N-methylamino)ethyl]2,6-dimethyl-4-(3-nitrophenyl)-1,4-dihydropyridine-3,5-dicarboxylate 3-[2-[(E)-3-[4-(pyridin-3-ylmethyl)phenyl]-2-methylallyloxy]ethyl]5-methyl 2,6-dimethyl-4-(3-nitrophenyl)-1,4-dihydropyridine-3,5-dicarboxylate 3-[2-[(E)-3-[4-(pyridin-3-ylmethyl)phenyl]-2-methylallyloxy]ethyl]5-isopropyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(3-trifluoromethylphenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(2-trifluoromethylphenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(2,3-dichlorophenyl)-1,4-dihydropyridine-3,5-dicarboxylate The physical properties of the compounds mentioned above were identical with those of the compounds obtained in Examples 27 to 30.

(2) In 9.5 ml of 2-propanol was dissolved 1.9 g of 3-[(E)-3-[4-(pyridin-3-ylmethyl)phenyl]-2-methylallyloxy]-2,2-dimethylpropyl acetoacetate, and an ammonia gas was blown thereinto with ice-cooling for 30 minutes, after which the resulting mixture was subjected to reaction at room temperature for one day. Subsequently, the solvent was removed by distillation under reduced pressure to obtain oily 3-[(E)-3-[4-(pyridin-3-ylmethyl)phenyl]-2-methylallyloxy]-2,2-dimethylpropyl 3-aminocrotonate. This oily product and 1.15 g of methyl 2-(3-nitrobenzylidene)acetoacetate were dissolved in 9.5 ml of 2-propanol, and the resulting solution was subjected to reaction under reflux for 3 hours. Subsequently, the solvent was removed by distillation under reduced pressure, and the residue thus obtained was purified by a column chromatography [Merck Silica Gel, 70–230 mesh, eluant: n-hexane:acetone (2:1 by volume)] to obtain 2.34 g (yield 79.0%) of yellow and oily 3-[3-[(E)-3-[4-(pyridin-3-ylmethyl)phenyl]-2-methylallyloxy]-2,2-dimethylpropyl]5-methyl 2,6-dimethyl-4-(3-nitrophenyl)-1,4-dihydropyridine-3,5-dicarboxylate.

The physical properties of this product were identical with those of the compound obtained in Example 27.

In the same manner as above, the following compounds were obtained:

3-[4-[(E)-3-[4-(pyridin-3-ylmethyl)phenyl]-2-methylallyloxy]butyl]5-ethyl 2,6-dimethyl-4-(3-nitrophenyl)-1,4-dihydropyridine-3,5-dicarboxylate 3-[5-[(E)-3-[4-(pyridin-3-ylmethyl)phenyl]-2-methylallyloxy]pentyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-1-methylpropyl]5-methyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2-methylpropyl]5-ethyl 2,6-dimethyl-4-(3-nitrophenyl)-1,4-dihydropyridine-3,5-dicarboxylate 3-[3-[(E)-3-[4-pyridin-3-ylmethyl)phenyl]-2-methylallyloxy]-2,2-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-isopropyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-1,3-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]allyloxy]-2,2-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-methyl 2,6-dimethyl-4-(3-fluorophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-ethyl 2,6-dimethyl-4-(2,3-dichlorophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-ethyl 2,6-dimethyl-4-(2-trifluoromethylphenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-isopropyl 2,6-dimethyl-4-(2-fluorophenyl)-1,4-dihydropyridine-3,5-dicarboxylate 3-[6-[(E)-3-[4-(pyridin-3-ylmethyl)phenyl]-2-methylallyloxy]hexyl]5-ethyl 2,6-dimethyl-4-(3-nitrophenyl)-1,4-dihydropyridine-3,5-dicarboxylate 3-[3-[(E)-3-[4-(pyridin-3-yloxy)phenyl]-2-methylallyloxy]-2,2-dimethylpropyl]5-ethyl 2,6-dimethyl-4-(3-nitrophenyl)-1,4-dihydropyridine-3,5-dicarboxylate The physical properties of the compounds mentioned above were identical with those of the compounds obtained in Example 27.

EXAMPLE 36

(1) In 5 ml of methylene chloride was suspended 260 mg of 5-ethoxycarbonyl-2,6-dimethyl-4-(3-nitrophenyl)-1,4-dihydropyridine-3-carboxylic acid, and to the resulting suspension was added 190 mg of oxalyl chloride with ice-cooling, after which the resulting mixture was subjected to reaction at room temperature for one hour. Subsequently, the excessive oxalyl chloride and methylene chloride was removed by distillation under reduced pressure. The residue thus obtained was dissolved in 5 ml of methylene chloride.

(2) In 10 ml of methylene chloride was dissolved 1.0 g of 2-[(E)-3-[4-(pyridin-3-ylmethyl)phenyl]allyloxy]ethanol, and then 0.11 ml of triethylamine was added thereto. To the resulting solution was dropwise added the methylene chloride solution obtained in (1) above with ice-cooling, and the resulting mixture was subjected to reaction at room temperature for one hour. To the reaction mixture were added 20 ml of methylene chloride and 20 ml of water, and the pH thereof was adjusted to 10 with a 10% by weight aqueous sodium carbonate solution. Subsequently, the organic layer was separated, washed successively with 20 ml of water and 20 ml of a saturated aqueous sodium chloride solution, and then dried over anhydrous magnesium sulfate. The solvent was removed by distillation under reduced pressure, and the residue thus obtained was purified by a column chromatography [Wako Silica Gel C-200, eluant: toluene:ethyl acetate (1:1 by volume)] to obtain 170 mg (yield 37.8%) of yellow, oily 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate. The physical properties of this product were identical with those of the product obtained in Example 27.

In the same manner as above, the following compounds were obtained:

3-[2-(E)-3-[4-(pyridin-3-ylmethyl)phenyl]-2-methylallyloxy]ethyl]5-ethyl, 2,6-dimethyl-4-(3-nitrophenyl)-1,4-dihydropyridine-3,5-dicarboxylate 3-[2-[4-(Imidazol-1-ylmethyl)phenyloxy]ethyl]5-ethyl 2,6-dimethyl-4-(3-nitrophenyl)-1,4-dihydropyridine-3,5-dicarboxylate 3-[2-[(E)-3-[4-(imidazol-1-ylmethyl)phenyl]allyloxy]ethyl]5-ethyl 2,6-dimethyl-4-(3-nitrophenyl)-1,4-dihydropyridine-3,5-dicarboxylate 3-[2-[4-(Pyridin-3-ylmethyl)phenyloxy]ethyl]5-ethyl 2,6-dimethyl-4-(3-nitrophenyl)-1,4-dihydropyridine-3,5-dicarboxylate 3-[2-[3-[4-(Pyridin-3-ylmethyl)phenyl]propyloxy]ethyl]5-ethyl 2,6-dimethyl-4-(3-nitrophenyl)-1,4-dihydropyridine-3,5-dicarboxylate 3-[2-[(E)-3-[5-(pyridin-3-ylmethyl)thiophen-2-yl]-2-methylallyloxy]ethyl]5-ethyl 2,6-dimethyl-4-(3-nitrophenyl)-1,4-dihydropyridine-3,5-dicarboxylate 3-[2-[(E)-3-[4-(pyridin-3-yloxy)phenyl]-2-methylallyloxy]ethyl]5-ethyl 2,6-dimethyl-4-(3-nitrophenyl)-1,4-dihydropyridine-3,5-dicarboxylate 3-[2-[4-(Imidazol-1-ylmethyl)benzyloxy]ethyl]5-ethyl 2,6-dimethyl-4-(3-nitrophenyl)-1,4-dihydropyridine-3,5-dicarboxylate 3-[2-[3-[4-(Imidazol-1-ylmethyl)phenyl]propyloxy]ethyl]5-ethyl 2,6-dimethyl-4-(3-nitrophenyl)-1,4-dihydropyridine-3,5-dicarboxylate 3-[2-[3-[4-(Pyridin-3-yloxy)phenyl]propyloxy]ethyl]5-ethyl 2,6-dimethyl-4-(3-nitrophenyl)-1,4-dihydropyridine-3,5-dicarboxylate 3-[2-[4-(Pyridin-3-ylmethyl)benzyloxy]ethyl]5-ethyl 2,6-dimethyl-4-(3-nitrophenyl)-1,4-dihydropyridine-3,5-dicarboxylate 3-[2-[2-[4-Pyridin-3-ylmethyl)phenyl]ethyloxy]ethyl]5-ethyl 2,6-dimethyl-4-(3-nitrophenyl)-1,4-dihydropyridine-3,5-dicarboxylate 3-[2-[(E)-3-[4-(pyridin-3-ylmethyl)phenyl]allylthio]ethyl]5-ethyl 2,6-dimethyl-4-(3-nitrophenyl)-1,4-dihydropyridine-3,5-dicarboxylate 3-[2-[(E)-3-[4-(pyridin-4-ylmethyl)phenyl]allyloxy]ethyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]allyloxy]propyl]5-ethyl 2,6-dimethyl-4-(3-nitrophenyl)-1,4-dihydropyridine-3,5-dicarboxylate 3-[2-[2-[(E)-3-[4-(pyridin-3-ylmethyl)phenyl]allyloxy]ethyloxy]ethyl]5-ethyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]1-methylethyl]5-ethyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-isopropyl 2,6-dimethyl-4-(3-nitrophenyl)-1,4-dihydropyridine-3,5-dicarboxylate 3-[2-[(E)-3-[4-pyridin-3-ylmethyl)phenyl]allyloxy]ethyl]5-(2-methoxy)ethyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5-[2-(N-benzyl-N-methylamino)ethyl]2,6-dimethyl-4-(3-nitrophenyl)-1,4-dihydropyridine-3,5-dicarboxylate 3-[2-[(E)-3-[4-(pyridin-3-ylmethyl)phenyl]-2-methylallyloxy]ethyl]5-methyl 2,6-dimethyl-4-(3-nitrophenyl)-1,4-dihydropyridine-3,5-dicarboxylate 3-[2-[(E)-3-[4-(pyridin-3-ylmethyl)phenyl]-2-methylallyloxy]ethyl]5-isopropyl 2,6-dimethyl-4-(3-nitrophenyl)-1,4-dihydropyridine-3,5-dicarboxylate 3-[2-[(E)-3-[4-(pyridin-3-ylmethyl)phenyl]allyloxy]ethyl]5methyl 2,6-dimethyl-4-(3-trifluoromethylphenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(2-trifluoromethylphenyl)-1,4-dihydropyridine-3,5-dicarboxylate 3-[2-[(E)-3-[4-(pyridin-3-ylmethyl)phenyl]allyloxy]ethyl]5-methyl 2,6-dimethyl-4-(2,3-dichlorophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-methyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-ethyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-(2-methoxyethyl) 2,6-dimethyl-4-(3-nitrophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-isopropyl 2,6-dimethyl-4-(2-trifluoromethylphenyl)-1,4-dihydropyridine-3,5-dicarboxylate.

3-[2-[N-methyl-N-[(E)-3-[4-(pyridin-3-ylmethyl)phenyl]-2-methylallyl]amino]ethyl]5-isopropyl 2,6-dimethyl-4-(2,3-dichlorophenyl)-1,4-dihydropyridine-3,5-dicarboxylate 3-[2-[N-methyl-N-[(E)-3-[4-(pyridin-3-ylmethyl)phenyl]allyl]amino]ethyl]5-isopropyl 2,6-dimethyl-4-(3-nitrophenyl)-1,4-dihydropyridine-3,5-dicarboxylate 3-[2-[N-benzyl-N-[(E)-3-[4-(pyridin-3-ylmethyl)phenyl]-2-methylallyl]amino]ethyl]5-isopropyl 2,6- dimethyl-4-(3-nitrophenyl)-1,4-dihydropyridine-3,5-dicarboxylate

3-[2-[N-methyl-N-[3-[4-(pyridin-3-ylmethyl)phenyl]-proyl]amino]ethyl]5-isopropyl 2,6-dimethyl-4-(3-nitrophenyl)-1,4-dihydropyridine-3,5-dicarboxylate 3-[2-[N-methyl-N-[(E)-3-[4-(imidazol-1-ylmethyl)-phenyl]allyl]amino]ethyl]5-isopropyl 2,6-dimethyl-4-(3-nitrophenyl)-1,4-dihydropyridine-3,5-dicarboxylate The physical properties of the compounds mentioned above were identical with those of the compounds obtained in Examples 27 to 34.

Example 37

In 10 ml of methylene chloride was dissolved 2.07 g of 3-[p-[3-(2-acetoxyethyl)oxy-1-hydroxy-2-methylpropyl]benzyl]pyridine, and to the resulting solution was added 0.88 ml of thionyl chloride with ice-cooling, after which the resulting mixture was subjected to reaction at the same temperature for one hour. The solvent and the excessive thionyl chloride were removed by distillation under reduced pressure. The residue thus obtained was dissolved in 10 ml of N,N-dimethylformamide, and to the resulting solution was dropwise added 4.5 ml of DBU, after which the resulting mixture was subjected to stirring at 100° to 110° C. for 2 hours. Subsequently, 5 ml of water was dropped into the mixture, and the mixture was subjected to reaction at 100° C. for 2 hours. The reaction mixture was poured into 80 ml of a saturated aqueous sodium chloride solution, and the resulting mixture was subjected to extraction with two 40-ml portions of ethyl acetate. The extracts were combined, washed with 20 ml of water and then dried over anhydrous magnesium sulfate. The solvent was removed by distillation under reduced pressure, and the residue thus obtained was purified by a column chromatography [Wako Silica Gel C-200, eluant: chloroform] to obtain 850 mg (yield 50.0%) of colorless, oily 3-[p-[3-(2-hydroxyethyl)oxy-2-methyl-1-propenyl]benzyl]pyridine.

IR (film) cm$^{-1}$: $\nu_{OH}$ 3350.

NMR (CDCl$_3$) δ values:

| 1.88 (3H, bs), | 3.33–4.14 (m) | } (9H), 6.42 (1H, bs), |
|---|---|---|
| | 3.90 (s) | |
| | 4.02 (s) | |

6.90–7.54 (6H, m), 8.30–8.55 (2H, m).

Example 38

(1) In 13.7 ml of ethanol was dissolved 2.74 g of 3-[p-[1-hydroxy-3-(2-hydroxyethyl)oxy-2-methylpropyl]-benzyl]pyridine, and the resulting solution was saturated with hydrogen chloride with ice-cooling, after which the solution was subjected to reaction at room temperature for 2 hours. The solvent was removed by distillation under reduced pressure, and to the residue thus obtained were added 10 ml of water and 20 ml of ethyl acetate, after which the pH of the resulting mixture was adjusted to 7.0 with sodium hydrogencarbonate. The organic layer was separated, washed with 10 ml of water, and then dried over anhydrous magnesium sulfate. The solvent was removed by distillation under reduced pressure to obtain 2.85 g (yield 98%) of colorless, oily 3-[p-[1-chloro-3-(2-hydroxyethyl)oxy-2-methylpropyl]benzyl]pyridine.

IR (film) cm$^{-1}$: $\nu_{OH}$ 3300.

NMR (CDCl$_3$) δ values:

| 0.82 (d, J=6 Hz) | } (3H), 1.92–2.62 (1H, m), |
|---|---|
| 0.98 (d, J=6 Hz) | |

| 3.12–4.30 (m) | } (9H), | 4.98 (d, J=8 Hz) | } (1H), |
|---|---|---|---|
| 3.92 (s) | | 5.18 (d, J=4 Hz) | |
| 4.12 (s) | | | |

6.82–7.58 (6H, m), 8.22–8.60 (2H, m).

(2) In 29.1 ml of dimethylsulfoxide was dissolved 5.82 g of 3-[p-[1-chloro-3-(2-hydroxyethyl)oxy-2-methylpropyl]benzyl]pyridine, and 5.44 ml of DBU was added to the resulting solution, after which the resulting mixture was subjected to reaction at a temperature of 100° to 110° C. for 2 hours. The reaction mixture was poured into 200 ml of water, and the resulting mixture was subjected to extraction with two 50-ml portions of ethyl acetate. The extracts were combined, washed with 20 ml of water, and then dried over anhydrous magnesium sulfate. The solvent was removed by distillation under reduced pressure, and the residue thus obtained was purified by a column chromatography [Wako Silica Gel C-200, eluant: chloroform] to obtain 3.20 g (yield 62.0%) of colorless, oily 3-[p-[3-(2-hydroxyethyl)oxy-2-methyl-1-propenyl]benzyl]pyridine.

IR and NMR spectra of this product were identical with those of the product obtained in Example 37.

Moreover, when the above product was reacted with hydrogen chloride in equimolar amounts in acetonitrile, and the crystals thus precipitated were collected by filtration to obtain colorless, needle-like crystals of 3-[p-[(E)-3-(2-hydroxyethyl)oxy-2-methyl-1-propenyl]benzyl]pyridine hydrochloride.

Melting point: 110°–112° C.

NMR (d$_6$-DMSO) δ values: 1.85 (3H, s), 3.30–3.80 (4H, m), 4.02 (2H, s), 4.22 (2H, s), 6.48 (1H, bs), 7.05–7.62 (4H, m), 7.00–9.20 (4H, m), 9.85 (2H, bs).

Example 39

From 3-[p-[3-(2-acetoxyethyl)oxy-1-hydroxypropyl]-benzyl]pyridine, there was obtained colorless, oily 3-[p-[3-(2-hydroxyethyl)oxy-1-propenyl]benzyl]pyridine (yield 73.3%) in the same manner as in Example 37.

IR (film) cm$^{-1}$: $\nu_{OH}$ 3350.

NMR (CDCl$_3$) δ values:

| 3.45–4.00 (m) | } (7H), 4.15 (2H, d, J=5 Hz), |
|---|---|
| 3.86 (s) | |

6.16 (1H, dt, J=16 Hz, 5 Hz), 6.56 (1H, d, J=16 Hz), 6.85–7.50 (6H, m), 8.30–8.55 (2H, m).

Example 40

In 3 ml of methylene chloride was dissolved 630 mg of 3-[p-[3-(2-tert-butoxyethyl)oxy-1-hydroxypropyl]-benzyl]pyridine, and to the resulting solution was added 0.27 ml of thionyl chloride with ice-cooling, after which the resulting mixture was subjected to reaction at room temperature for 30 minutes. The solvent and the excessive thionyl chloride were removed by distillation under reduced pressure, and the residue thus obtained was dissolved in 3 ml of N,N-dimethylformamide, and 1.38 ml of DBU was added to the resulting solution, after which the resulting mixture was subjected to reaction at a temperature of 110° to 115° C. for 2 hours. To the reaction mixture were added 10 ml of water and 10 ml of toluene, and the pH of the mixture was adjusted to 7.5 with 2N hydrochloric acid. The organic layer was separated, washed with 5 ml of water, and then dried over anhydrous magnesium sulfate. The solvent was removed by distillation under reduced pressure, and the residue thus obtained was purified by a column chromatography [Wako Silica Gel C-200, eluant: toluene:ethyl acetate (10:1 by volume)] to obtain 450 mg (yield 75.0%) of colorless, oily 3-[p-[3-(2-tert-butoxyethyl-)oxy-1-propenyl]benzyl]pyridine.

NMR (CDCl$_3$) δ values: 1.20 (9H, s), 3.55 (4H, s), 3.91 (2H, s), 4.15 (2H, d, J=5 Hz), 6.17 (1H, dt, J=16 Hz, 5 Hz), 6.58 (1H, d, J=16 Hz), 6.92–7.51 (6H, m), 8.32–8.52 (2H, m).

Example 41

(1) In 4.6 ml of methylene chloride was dissolved 910 mg of 3-[p-(3-acetoxy-1-hydroxy-2-methylpropyl)benzyl]pyridine, and to the resulting solution was added 0.48 ml of thionyl chloride with ice-cooling, after which the resulting mixture was subjected to reaction at the same temperature for one hour. The solvent and the excessive thionyl chloride were removed by distillation under reduced pressure, and to the residue thus obtained were added 10 ml of methyl acetate and 10 ml of water, after which the resulting mixture was neutralized with sodium hydrogencarbonate. The organic layer was separated, washed with 5 ml of water, and then dried over anhydrous magnesium sulfate. The solvent was removed by distillation under reduced pressure, and the residue thus obtained was purified by a column chromatography [Wako Silica Gel C-200, eluant: benzene:ethyl acetate (5:1 by volume)] to obtain 740 mg (yield 86.0%) of colorless, oily 3-[p-(3-acetoxy-1-chloro-2-methylpropyl)benzyl]pyridine.

IR (film) cm$^{-1}$: $\nu_{C=O}$ 1740.

NMR (CDCl$_3$) δ values:

| 0.85 (d, J=6 Hz) | (3H), | 1.80–2.70 (m) | (4H), |
| 1.02 (d, J=6 Hz) | | 1.98 (s), 2.00 (s) | |
| 3.25–4.30 (m) | (4H), | 4.80 (d, J=8 Hz) | (1H), |
| 3.90 (s) | | 4.95 (d, J=6 Hz) | |

6.90–7.55 (6H, m), 8.22–8.55 (2H, m).

(2) In 10 ml of methanol was dissolved 740 mg of 3-[p-(3-acetoxy-1-chloro-2-methylpropyl)benzyl]pyridine, and to the resulting solution was added 40 mg of sodium methoxide with ice-cooling, after which the resulting mixture was subjected to reaction at room temperature for 30 minutes. To the reaction mixture was added 0.1 ml of acetic acid, and the solvent was removed by distillation under reduced pressure, after which the residue thus obtained was dissolved in 10 ml of ethyl acetate. The resulting solution was washed with 5 ml of water and then dried over anhydrous magnesium sulfate. The residue thus obtained was purified by a column chromatography [Wako Silica Gel C-200, eluant: benzene:ethyl acetate (1:1 by volume)] to obtain 400 mg (yield 62.3%) of colorless, oily 3-[p-(1-chloro-3-hydroxy-2-methylpropyl)benzyl]pyridine.

IR (film) cm$^{-1}$: $\nu_{OH}$ 3300.

NMR (CDCl$_3$) δ values: 0.98 (3H, d, J=6 Hz), 1.80–2.42 (1H, m),

| 3.30–4.00 (m) | (5H), 5.18 (1H, d, J=5 Hz), |
| 3.92 (s) | |

6.85–7.58 (6H, m), 8.20–8.50 (2H, m).

(3) In 1.3 ml of N,N-dimethylformamide was dissolved 260 mg of 3-[p-(1-chloro-3-hydroxy-2-methylpropyl)benzyl]pyridine, and 0.28 ml of DBU was added to the resulting solution after which the resulting mixture was subjected to reaction at a temperature of 110° to 120° C. for one hour. To the reaction mixture was added 5 ml of water, and the mixture was subjected to extraction with two 5-ml portions of ethyl acetate. The extracts were combined, washed with 3 ml of water, and then dried over anhydrous magnesium sulfate. The solvent was removed by distillation under reduced pressure, and the residue thus obtained was purified by a colomn chromatography [Wako Silica Gel C-200, eluant: benzene:ethyl acetate (3:1 by volume)] to obtain 150 mg (yield 62.7%) of colorless, oily 3-[p-(3-hydroxy-2-methyl-1-propenyl)benzyl]pyridine.

IR (film) cm$^{-1}$: $\nu_{OH}$ 3300.

NMR (CDCl$_3$) δ values: 1.88 (3H, s), 3.88 (2H, s), 4.16 (2H, s), 4.55 (1H, s), 6.46 (1H, s), 6.82–7.56 (6H, m), 8.20–8.50 (2H, m).

Example 42

(1) In 3 ml of 2-propanol was dissolved 760 mg of 2-[N-methyl-N-[(E)-3-[4-(pyridin-3-ylmethyl)phenyl]-2-methylallyl]amino]ethyl acetoacetate, and into the resulting solution was introduced ammonia with ice-cooling for one hour. The resulting mixture was allowed to stand at room temperature for 15 hours, and then, the solvent was removed by distillation under reduced pressure to obtain pale yellow, oily 2-[N-methyl-N-[(E)-3-[4-(pyridin-3-ylmethyl)phenyl]-2-methylallyl]amino]ethyl 3-aminocrotonate. Subsequently, this product was dissolved in 3.36 ml of 2-propanol.

(2) To the 2-propanol solution obtained in (1) above was added 584 mg of isopropyl 2-(3-nitrobenzylidene)acetoacetate, and the resulting mixture was subjected to reaction under reflux for 2 hours. The solvent was removed by distillation under reduced pressure, and the residue thus obtained was purified by a column chromatography [Wako Silica Gel C-200, eluant: acetone:hexane (1:2 by volume)] to obtain 1.20 g (yield 98.7%) of yellow, oily 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate.

In the same manner as above, the following compounds were obtained:

3-[2-[N-methyl-N-[(E)-3-[4-pyridin-3-ylmethyl)-phenyl]-2-methylallyl]amino]ethyl]5-isopropyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)-phenyl]-2-methylallyl]amino]ethyl]5-methyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)-phenyl]-2-methylallyl]amino]ethyl]5-ethyl 2,6-dimethyl-4-(3-nitrophenyl)-1,4-dihydropyridine-3,5-dicarboxylate 3-[2-[N-methyl-N-[(E)-3-[4-(pyridin-3-ylmethyl)-phenyl]-2-methylallyl]amino]ethyl]5-(2-methoxyethyl) 2,6-dimethyl-4-(3-nitrophenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-isopropyl 2,6-dimethyl-4-(2-trifluoromethylphenyl)-1,4-dihydropyridine-3,5-dicarboxylate 3-[2-[N-methyl-N-[(E)-3-[4-(pyridin-3-ylmethyl)phenyl]-2-methylallyl]amino]ethyl]5-isopropyl 2,6-dimethyl-4-(2,3-dichlorophenyl)-1,4-dihydropyridine-3,5-dicarboxylate 3-[2-[N-methyl-N-[(E)-3-[4-(pyridin-3-ylmethyl)phenyl]allyl]amino]ethyl]5-isopropyl 2,6-dimethyl-4-(3-nitrophenyl)-1,4-dihydropyridine-3,5-dicarboxylate 3-[2-[N-benzyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate 3-[2-[N-methyl-N-[3-[4-(pyridin-3-ylmethyl)phenyl]propyl]amino]ethyl]5-isopropyl 2,6-dimethyl-4-(3-nitrophenyl)-1,4-dihydropridine-3,5-dicarboxylate 3-[2-[N-methyl-N-[(E)-3-[4-(imidazol-1-ylmethyl)phenyl]allyl]amino]ethyl]5-isopropyl 2,6-dimethyl-4-(3-nitrophenyl)-1,4-dihydropyridine-3,5-dicarboxylate The physical properties of the compounds mentioned above were identical with those of the compounds obtained in Example 31.

Example 43

In 33 ml of anhydrous tetrahydrofuran was dissolved 6.5 g of ethyl (E)-3-[4-(pyridin-3-ylmethyl)phenyl]-2-methylacrylate, and to the resulting solution was added 0.66 g of lithium aluminum hydride in small portions at room temperature. Further, the resulting mixture was subjected to reaction at the same temperature for one hour, and thereafter, 30 ml of ethyl acetate and then 2.5 ml of water were added in small portions with water-cooling. The insolubles were removed by filtration, and thereafter, the organic layer was dried over anhydrous magnesium sulfate. Subsequently, the solvent was removed by distillation under reduced pressure, and the residue thus obtained was purified by a column chromatography [Wako Silica Gel C-200, eluant: benzene:ethyl acetate (3:1 by volume)], to obtain 4.0 g (yield 72.3%) of colorless, oily (E)-3-[4-(pyridin-3-ylmethyl)phenyl]-2-methylallyl alcohol.

IR (film) cm$^{-1}$: 3350–3230.

NMR (CDCl$_3$) δ values: 1.92 (3H, bs), 3.98 (2H, s), 4.25 (3H, bs), 6.63 (1H, bs), 6.90–7.68 (6H, m), 8.40–8.70 (2H, m).

In the same manner as above, the following compounds were obtained:

(E)-3-[4-(pyridin-3-yloxy)phenyl]-2-methylallyl alcohol (colorless and oily)

IR (film) cm$^{-1}$: 3500–3100, 1600.

NMR (CDCl$_3$) δ values: 1.89 (3H, s), 3.50 (1H, bs), 4.16 (2H, s), 6.46 (1H, s), 6.82–7.36 (6H, m), 8.20–8.42 (2H, m).

(E)-3-[4-(pyridin-3-ylmethyl)phenyl]allyl alcohol

Melting point: 81°–82° C.

IR (KBr) cm$^{-1}$: 3240.

NMR (CDCl$_3$) δ values: 3.85 (2H, s), 4.23 (1H, s), 4.27 (2H, d, J=4.5 Hz), 6.28 (1H, dt, J=16 Hz, 4.5 Hz), 6.50 (1H, d, J=16 Hz), 6.85–7.55 (6H, m), 8.20–8.51 (2H, m).

Example 44

(1) In 24 ml of methylene chloride was dissolved 1.2 g of (E)-3-[4-(pyridin-3-ylmethyl)phenyl]-2-methylallyl alcohol, and 1.8 ml of thionyl chloride was dropped into the resulting solution with ice-cooling, after which the resulting mixture was subjected to reaction under reflux for 30 minutes. The solvent and the excessive thionyl chloride were removed by distillation under reduced pressure, to obtain as the residue (E)-3-[4-(pyridin-3-ylmethyl)phenyl]-2-methylallyl chloride hydrochloride. This was crystallized from a mixed solvent of 2-propanol and ethyl acetate to obtain colorless, needle-like crystals having a melting point of 118°–120° C.

IR (KBr) cm$^{-1}$: 2550, 1600.

NMR (CDCl$_3$) δ values: 1.98 (3H, bs), 4.18 (2H, s), 4.28 (2H, s), 6.54 (1H, bs), 7.22 (4H, bs), 7.84–8.60 (2H, m), 8.65–9.00 (2H, m), 15.60 (1H, bs).

Elementary analysis value (%): Calcd. C: 65.31, H: 5.82, N: 4.76. Found: C: 65.42, H: 5.76, N: 4.85.

(2) In 10.4 ml of dimethyl sulfoxide was dissolved 10.4 g of 2,2-dimethyl-1,3-propandiol, and to the resulting solution was added 0.8 g of sodium hydride (purity 60%) in small portions at room temperature. The resulting mixture was stirred at 50° C. for 30 minutes, and thereafter, to the resulting solution was added dropwise a solution in 5 ml of dimethylsulfoxide of the residue (E)-3-[4-(pyridin-3-ylmethyl)phenyl]-2-methylallyl chloride hydrochloride obtained in (1) above at room temperature, and the resulting mixture was subjected to reaction at 50° C. for a further one hour. Subsequently, 40 ml of water was added to the reaction mixture with ice-cooling, and the pH thereof was adjusted to 7 with 2N hydrochloric acid, after which the mixture was extracted with two 30-ml portions of ethyl acetate. The thus obtained organic layer was washed with two 20-ml portions of water, and the pH thereof was adjusted to 1.0 with 2N hydrochloric acid with ice-cooling. Subsequently, the water layer was separated, and 50 ml of ethyl acetate was added thereto, after which the resulting mixture was neutralized with sodium hydrogencarbonate. The organic layer was separated, and thereafter, washed with 20 ml of saturated aqueous sodium chloride solution, and then dried over anhydrous magnesium sulfate. The solvent was removed by distillation under reduced pressure, and the residue thus obtained was purified by a column chromatography [Merck Silica Gel, 70–230 mesh, eluant: n-hexane:acetone (3:1 by volume)] to obtain 1.05 g (yield 64.5%) of colorless, oily 3-[(E)-3-[4-(pyridin-3-ylmethyl)phenyl]-2-methylallyloxy]-2,2-dimethylpropanol.

IR (film) cm$^{-1}$: 3350.

NMR (CDCl$_3$) δ values: 0.95 (6H, s), (3H, bs), 3.26 (2H, s), 3.45 (2H, s), 3.71 (1H, bs), 3.92 (2H, s), 3.96 (2H, s), 6.40 (1H, bs), 6.95–7.55 (6H, m), 8.26–8.50 (2H, m).

(3) In the same manner as in (1) and (2) above, the following compounds were obtained:

5-[(E)-3-[4-(pyridin-3-ylmethyl)phenyl]-2-methylallyloxy]pentanol

3-[(E)-3-[4-(pyridin-3-ylmethyl)phenyl]-2-methylallyloxy]-1-methylpropanol

3-[(E)-3-[4-(pyridin-3-ylmethyl)phenyl]-2-methylallyloxy]-2-methylpropanol

3-[(E)-3-[4-(pyridin-3-ylmethyl)phenyl]-2-methylallyloxy]butanol

3-[(E)-3-[4-(pyridin-3-ylmethyl)phenyl]allyloxy]-2,2-dimethylpropanol

3-[(E)-3-[4-(pyridin-3-ylmethyl)phenyl]-2-methylallyloxy]-1,3-dimethylpropanol

6-[(E)-3-[4-(pyridin-3-ylmethyl)phenyl]-2-methylallyloxy]hexanol

3-[(E)-3-[4-(pyridin-3-yloxy)phenyl]-2-methylallyloxy]-2,2-dimethylpropanol

The physical properties of the compounds mentioned above were identical with those of the compounds obtained in Example 4.

Example 45

In 50 ml of ethyl acetate was dissolved 9.2 g of 3-[(E)-3-[4-(pyridin-3-ylmethyl)phenyl]-2-methylallyloxy]-2,2-dimethylpropanol, and one drop of triethylamine was added to the resulting solution. To the solution was added dropwise a mixture of 3.1 g of diketene and 9.2 ml of ethyl acetate under reflux over one hour, and the resulting mixture was then subjected to reaction at the same temperature for 30 minutes. Subsequently, the solvent was removed by distillation under reduced pressure, and the residue thus obtained was purified by a column chromatography [Merck Silica Gel, 70–230 mesh, eluant: toluene:ethyl acetate (4:1 by volume)] to obtain 7.05 g (yield 60.8%) of oily 3-[(E)-3-[4-(pyridin-3-ylmethyl)phenyl]-2-methylallyloxy]-2,2-dimethylpropyl acetoacetate.

IR (film) cm$^{-1}$: 1730, 1710.

NMR (CDCl$_3$) δ values: 0.98 (6H, s), 1.96 (3H, bs), 2.22 (3H, s),

| 3.19 (2H, s), 3.54 (2H, s), | 3.96 (s)<br>3.98 (s)<br>4.01 (s) | (6H), |
|---|---|---|

6.42 (1H, bs), 7.00–7.58 (6H, m), 8.35–8.62 (2H, m).

In the same manner as above, the following compounds were obtained:

5-[(E)-3-[4-(pyridin-3-ylmethyl)phenyl]-2-methylallyloxy]pentyl acetoacetate

4-[(E)-3-[4-(pyridin-3-ylmethyl)phenyl]-2-methylallyloxy]butyl acetoacetate

3-[(E)-3-[4-(pyridin-3-ylmethyl)phenyl]-2-methylallyloxy]-1-methylpropyl acetoacetate 3-[(E)-3-[4-(pyridin-3-ylmethyl)phenyl]-2-methylallyloxy]-2-methylpropyl acetoacetate 3-[(E)-3-[4-(pyridin-3-ylmethyl)phenyl]-2-methylallyloxy]-1,3-dimethylpropyl acetoacetate 3-[(E)-3-[4-(pyridin-3-ylmethyl)phenyl]allyloxy]-2,2-dimethylpropyl acetoacetate 6-[(E)-3-[4-(pyridin-3-ylmethyl)phenyl]-2-methylallyloxy]hexyl acetoacetate 3-[(E)-3-[4-(pyridin-3-yloxy)phenyl]-2-methylallyloxy]-2,2-dimethylpropyl acetoacetate The physical properties of the compounds mentioned above were identical with those of the compounds obtained in Example 27.

Example 46

In 8 ml of 2-propanol were dissolved 1 g of 3-[(E)-3-[4-(pyridin-3-ylmethyl)phenyl]-2-methylallyloxy]-2,2-dimethylpropyl acetoacetate, 0.28 g of methyl 3-aminocrotonate and 0.37 g of 3-nitrobenzaldehyde, and the resulting solution was subjected to reaction under reflux for 8 hours. Subsequently, the solvent was removed by distillation under reduced pressure, and the residue thus obtained was purified by a column chromatography [Merck Silica Gel, 70–230 mesh, eluant: n-hexane:acetone (2:1 by volume)] to obtain 0.86 g (yield 55.0%) of yellow, oily 3-[3-[(E)-3-[4-(pyridin-3-ylmethyl)phenyl]-2-methylallyloxy]-2,2-dimethylpropyl]5-methyl 2,6-dimethyl-4-(3-nitrophenyl)-1,4-dihydropyridine-3,5-dicarboxylate.

IR (film) cm$^{-1}$: 3330, 1685, 1520, 1345.

NMR (CDCl$_3$) δ values:

| 0.91 (6H, s), 1.80 (3H, bs), | 2.31 (s)<br>2.37 (s) | (6H), |
|---|---|---|
| 3.11 (2H, s), 3.66 (3H, s), | 3.89–3.99 (m)<br>3.92 (s) | (6H), |

5.14 (1H, s), 6.36 (1H, bs), 6.95–8.13 (11H, m), 8.32–8.55 (2H, m).

In the same manner as above, the following compounds are obtained:

3-[4-[(E)-3-[4-(pyridin-3-ylmethyl)phenyl]-2-methylallyloxy]butyl]5-ethyl 2,6-dimethyl-4-(3-nitrophenyl)-1,4-dihydropyridine-3,5-dicarboxylate 3-[5-[(E)-3-[4-(pyridin-3-ylmethyl)phenyl]-2-methylallyloxy]pentyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-1-methylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2-methylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-isopropyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-1,3-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]allyloxy]-2,2-dimethylpropyl]5-ethyl 2,6-dimethyl-4-(3-nitrophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-methyl 2,6-dimethyl-4-(3-fluorophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-ethyl 2,6-dimethyl-4-(2,3-dichlorophenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-ethyl 2,6-dimethyl-4-(2-trifluoromethylphenyl)-1,4-dihydropyridine-3,5-dicarboxylate 3-[3-[(E)-3-[4-(pyridin-3-ylmethyl)phenyl]-2-methylallyloxy]-2,2-dimethylpropyl]5-isopropyl 2,6-dimethyl-4-(2-fluorophenyl)-1,4-dihydropyridine-3,5-dicarboxylate 3-[6-[(E)-3-[4-(pyridin-3-ylmethyl)phenyl]-2-methylallyloxy]hexyl]5-ethyl 2,6-dimethyl-4-(3-nitrophenyl)-1,4-dihydropyridine-3,5-dicarboxylate 3-[3-[(E)-3-[4-(pyridin-3-yloxy)phenyl]-2-methylallyloxy]-2,2-dimethylpropyl]5-ethyl 2,6-dimethyl-4-

(3-nitrophenyl)-1,4-dihydropyridine-3,5-dicarboxylate

The physical properties of the compounds mentioned above were identical with those of the compounds obtained in Example 27.

Preparation Example 1

Tablets containing 25 mg per tablet of 3-[2-[(E)-3-[4-(pyridin-3-ylmethyl)phenyl]allyloxy]ethyl]5-ethyl 2,6-dimethyl-4-(3-nitrophenyl)-1,4-dihydropyridine-3,5-dicarboxylate hydrochloride were produced in a manner known per se using the following additives:

Per 10,000 tablets:
    The above compound: 250 g
    Cellulose: 700 g
    Lactose: 780 g
    Corn starch: 700 g
    Magnesium stearate: 20 g
    Water: Appropriate amount Preparation Example 2

Tablets containing 25 mg per tablet of 3-[2-[N-methyl-N-[(E)-3-[4-(pyridin-3-ylmethyl)phenyl]-2-methylallyl]amino]ethyl]5-isopropyl 2,6-dimethyl-4-(3-nitrophenyl)-1,4-dihydropyridine-3,5-dicarboxylate hydrochloride were prepared in a manner known per se using the following additives:

Per 10,000 tablets:
    The above compound: 250 g
    Cellulose: 700 g
    Lactose: 780 g
    Corn starch: 700 g
    Magnesium stearate: 20 g
    Water: Appropriate amount

What is claimed is:

1. A 1,4-dihydropyridine represented by the formula (I) or a pharmaceutically acceptable salt thereof:

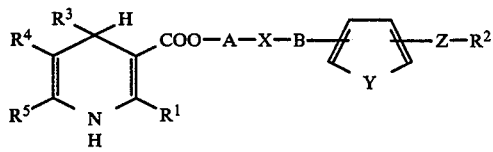

wherein $R^1$ and $R^5$, which may be the same or different, represent lower alkyl groups, $R^2$ represents a pyridyl group; $R^3$ represents a phenyl group or a phenyl group substituted by at least one substituent selected from the group consisting of halogen atoms and nitro, cyano, azido, lower alkyl, lower alkoxy, trihalo-lower alkyl, lower alkanesulfonyl, benzyl, phenethyl, methylbenzyl, chlorobenzyl, methoxybenzyl, phenyl, naphthyl, benzyloxy, phenethyloxy, p-chlorobenzyloxy, p-methoxybenzyloxy, phenoxy, naphthoxy, p-methylphenoxy, lower alkythio, phenylthio, naphthylthio, p-methylphenylthio, benzylthio, phenethylthio, p-chlorobenzylthio, p-methoxybenzylthio and lower alkoxycarbonyl groups; $R^4$ represents a carboxyl group esterified with a group selected from the group consisting of lower alkyl, lower alkoxy-lower alkyl, lower alkylthio-lower alkyl, N,N-di(lower alkyl)amino-lower alkyl, N-benzyl-N-lower alkylamino-lower alkyl, N-(4-chlorobenzyl)-N-lower alkylamino-lower alkyl, N-phenyl-N-lower alkylamino-lower alkyl and N,N-dibenzylamino-lower alkyl; A represents an alkylene group; B represents an alkenylene group; X represents an oxygen atom; Y represents a vinylene group; and Z represents an alkylene group.

2. The compound according to claim 1 which is 3-[4-[(E)-3-[4-(pyridin-3-ylmethyl)phenyl]-2-methylallyloxy]butyl]5-ethyl 2,6-dimethyl-4-(3-nitrophenyl)-1,4-dihydropyridine-3,5-dicarboxylate or a pharmaceutically acceptable salt thereof.

3. The compound according to claim 1 which is 3-[3-[(E)-3-[4-(pyridin-3-ylmethyl)phenyl]-2-methylallyloxy]-2-methylpropyl]5-ethyl 2,6-dimethyl-4-(3-nitrophenyl)-1,4-dihydropyridine-3,5-dicarboxylate or a pharmaceutically acceptable salt thereof.

4. The compound according to claim 1 which is 3-[3-[(E)-[4-(pyridin-3-ylmethyl)phenyl]-2-methylallyloxy]-2,2-dimethylpropyl]5-methyl 2,6-dimethyl-4-(3-nitrophenyl)-1,4-dihydropyridine-3,5-dicarboxylate or a pharmaceutically acceptable salt thereof.

5. The compound according to claim 1 which is 3-[3-[(E)-3-[4-(pyridin-3-ylmethyl)phenyl]-2-methylallyloxy]-2,2-dimethylpropyl]5-ethyl 2,6-dimethyl-4-(3-nitrophenyl)-1,4-dihydropyridine-3,5-dicarboxylate or a pharmaceutically acceptable salt thereof.

6. A vasodilator or platelet aggregation inhibitor which comprises an effective amount of a compound or its pharmaceutically acceptable salt as claimed in claim 1, in combination with a pharmaceutically acceptable excipient, carrier or diluent.

* * * * *